(12) United States Patent
Brar et al.

(10) Patent No.: US 10,194,980 B1
(45) Date of Patent: Feb. 5, 2019

(54) METHODS FOR CATHETER-BASED RENAL NEUROMODULATION

(71) Applicant: Medtronic Ardian Luxembourg S.a.r.l., Luxembourg (LU)

(72) Inventors: Sandeep S. Brar, Dublin, CA (US); Minglei Liu, Windsor, CA (US); Manuela Negoita, Santa Rosa, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 530 days.

(21) Appl. No.: 14/656,892

(22) Filed: Mar. 13, 2015

Related U.S. Application Data

(60) Provisional application No. 61/967,873, filed on Mar. 28, 2014, provisional application No. 61/967,874, (Continued)

(51) Int. Cl.
*A61B 18/12* (2006.01)
*A61B 18/14* (2006.01)
(Continued)

(52) U.S. Cl.
CPC .......... *A61B 18/1492* (2013.01); *A61B 18/02* (2013.01); *A61N 7/022* (2013.01);
(Continued)

(58) Field of Classification Search
None
See application file for complete search history.

(56) References Cited

U.S. PATENT DOCUMENTS 2,130,758 A 9/1938 Rose
2,276,995 A 3/1942 Milinowski
(Continued)

FOREIGN PATENT DOCUMENTS

DE 3151180 8/1982
EP 0811395 12/1997
(Continued)

OTHER PUBLICATIONS

Mahfoud et al., "Ambulatory Blood Pressure Changes after Renal Sympathetic Denervation in Patients with Resistant Hypertension", Jun. 2013, Circulation, 25 Pages.*
(Continued)

*Primary Examiner* — Ronald Hupczey, Jr.

(57) ABSTRACT

Methods for treating preventing or decreasing the likelihood of a human patient developing hypertension and associated systems and methods are disclosed herein. One aspect of the present technology, for example, is directed to methods for therapeutic renal neuromodulation that partially inhibit sympathetic neural activity in renal nerves proximate a renal blood vessel of a human patient. This reduction in sympathetic neural activity is expected to therapeutically treat one or more conditions associated with hypertension or prehypertension of the patient. Renal sympathetic nerve activity can be modulated, for example, using an intravascularly positioned catheter carrying a neuromodulation assembly, e.g., a neuromodulation assembly configured to use electrically-induced, thermally-induced, and/or chemically-induced approaches to modulate the renal nerves.

15 Claims, 38 Drawing Sheets

Related U.S. Application Data filed on Mar. 28, 2014, provisional application No. 61/967,875, filed on Mar. 28, 2014, provisional application No. 61/967,876, filed on Mar. 28, 2014, provisional application No. 61/967,877, filed on Mar. 28, 2014, provisional application No. 61/967,880, filed on Mar. 28, 2014, provisional application No. 61/967,888, filed on Mar. 28, 2014, provisional application No. 61/967,891, filed on Mar. 28, 2014, provisional application No. 62/018,919, filed on Jun. 30, 2014, provisional application No. 62/049,770, filed on Sep. 12, 2014, provisional application No. 62/050,083, filed on Sep. 13, 2014, provisional application No. 62/056,658, filed on Sep. 29, 2014, provisional application No. 62/056,659, filed on Sep. 29, 2014, provisional application No. 62/060,627, filed on Oct. 7, 2014, provisional application No. 62/068,262, filed on Oct. 24, 2014, provisional application No. 62/101,939, filed on Jan. 9, 2015, provisional application No. 62/101,936, filed on Jan. 9, 2015, provisional application No. 62/102,128, filed on Jan. 12, 2015.

(51) Int. Cl.
*A61B 18/02* (2006.01)
*A61N 7/02* (2006.01)
*A61B 18/00* (2006.01)
*A61N 7/00* (2006.01)

(52) U.S. Cl.
CPC .......... *A61B 2018/00404* (2013.01); *A61B 2018/00434* (2013.01); *A61B 2018/00505* (2013.01); *A61B 2018/00577* (2013.01); *A61B 2018/0212* (2013.01); *A61B 2018/1467* (2013.01); *A61N 2007/003* (2013.01)

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler et al. |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker, Jr. et al. |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |

(56) References Cited

U.S. PATENT DOCUMENTS

| | | |
|---|---|---|
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,700 A | 4/1996 | Leone et al. |
| 5,507,724 A | 4/1996 | Hofmann et al. |
| 5,507,791 A | 4/1996 | Sit'ko et al. |
| 5,531,778 A | 7/1996 | Maschino et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens et al. |
| 5,584,863 A | 12/1996 | Rauch et al. |
| 5,588,964 A | 12/1996 | Imran et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu et al. |
| 5,893,885 A | 4/1999 | Webster et al. |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 6,006,134 A | 12/1999 | Hill et al. |
| 6,009,877 A | 1/2000 | Edwards |
| 6,010,613 A | 1/2000 | Walters et al. |
| 6,026,326 A | 2/2000 | Bardy |
| 6,041,252 A | 3/2000 | Walker et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,146,380 A | 11/2000 | Racz et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,238,702 B1 | 5/2001 | Berde et al. |
| 6,245,026 B1 | 6/2001 | Campbell et al. |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |

(56) References Cited

U.S. PATENT DOCUMENTS

| | | |
|---|---|---|
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,711,444 B2 | 3/2004 | Koblish |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,749,598 B1 | 6/2004 | Keren et al. |
| 6,786,904 B2 | 9/2004 | Doscher et al. |
| 6,795,728 B2 | 9/2004 | Chornenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,885,888 B2 | 4/2005 | Rezai |
| 6,916,656 B2 | 7/2005 | Walters et al. |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,373,204 B2 | 5/2008 | Gelfand et al. |
| 7,444,183 B2 | 10/2008 | Knudson et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,756,583 B2 | 7/2010 | Demarais et al. |
| 8,131,371 B2 | 3/2012 | Demarais et al. |
| 8,145,317 B2 | 3/2012 | Demarais et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050681 A1 | 3/2003 | Pianca et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |

(56) References Cited

U.S. PATENT DOCUMENTS

| | | |
|---|---|---|
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0095029 A1 | 5/2006 | Young et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0190044 A1 | 8/2006 | Libbus et al. |
| 2006/0206149 A1 | 9/2006 | Yun |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0213331 A1 | 9/2008 | Gelfand et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062873 A1 | 3/2009 | Wu et al. |
| 2009/0076409 A1 | 3/2009 | Wu et al. |
| 2010/0010567 A1 | 1/2010 | Deem et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1* | 7/2010 | Wu ................ A61B 18/1206 606/33 |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0249773 A1 | 9/2010 | Clark et al. |
| 2010/0268307 A1 | 10/2010 | Demarais et al. |
| 2011/0060324 A1 | 3/2011 | Wu et al. |
| 2011/0112400 A1 | 5/2011 | Emery et al. |
| 2011/0137298 A1 | 6/2011 | Nguyen et al. |
| 2011/0178570 A1 | 7/2011 | Demarais |
| 2011/0200171 A1 | 8/2011 | Beetel et al. |
| 2011/0202098 A1 | 8/2011 | Demarais et al. |
| 2011/0207758 A1* | 8/2011 | Sobotka ............ A61B 18/1492 514/272 |
| 2011/0257564 A1 | 10/2011 | Demarais et al. |
| 2011/0264011 A1 | 10/2011 | Wu et al. |
| 2011/0264075 A1 | 10/2011 | Leung et al. |

FOREIGN PATENT DOCUMENTS

| | | |
|---|---|---|
| EP | 2092957 | 8/2009 |
| WO | WO-85/01213 | 3/1985 |
| WO | WO-91/04725 | 4/1991 |
| WO | WO-9220291 | 11/1992 |
| WO | WO-93/02740 | 2/1993 |
| WO | WO-93/07803 | 4/1993 |
| WO | WO-94/00188 | 1/1994 |
| WO | WO-94/11057 | 5/1994 |
| WO | WO-95/25472 | 9/1995 |
| WO | WO-95/33514 | 12/1995 |
| WO | WO-96/00039 | 1/1996 |
| WO | WO-96/04957 | 2/1996 |
| WO | WO-96/11723 | 4/1996 |
| WO | WO-97/13463 | 4/1997 |
| WO | WO-97/13550 | 4/1997 |
| WO | WO-1997036548 | 10/1997 |
| WO | WO-97/49453 | 12/1997 |
| WO | WO-98/37926 | 9/1998 |
| WO | WO-98/42403 | 10/1998 |
| WO | WO-98/43700 | 10/1998 |
| WO | WO-98/43701 | 10/1998 |
| WO | WO-98/48888 | 11/1998 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-2001022897 | 4/2001 |
| WO | WO-0170114 | 9/2001 |
| WO | WO-02/09808 | 2/2002 |
| WO | WO-02/26314 | 4/2002 |
| WO | WO-02/053207 | 7/2002 |

(56) References Cited

FOREIGN PATENT DOCUMENTS

| WO | WO-02/070039 | 9/2002 |
|---|---|---|
| WO | WO-02/070047 | 9/2002 |
| WO | WO-02/085448 | 10/2002 |
| WO | WO-2002085192 | 10/2002 |
| WO | WO-03/018108 | 3/2003 |
| WO | WO-03/028802 | 4/2003 |
| WO | WO-03/063692 | 8/2003 |
| WO | WO-03/071140 | 8/2003 |
| WO | WO-03/076008 | 9/2003 |
| WO | WO-03/082403 | 10/2003 |
| WO | WO-2003/082080 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005/014100 | 2/2005 |
| WO | WO-2005/016165 | 2/2005 |
| WO | WO-05/032646 | 4/2005 |
| WO | WO-2005/032646 | 4/2005 |
| WO | WO-2005030072 | 4/2005 |
| WO | WO-2005041748 | 5/2005 |
| WO | WO-2005/065284 | 7/2005 |
| WO | WO-2005/084389 | 9/2005 |
| WO | WO-2005/097256 | 10/2005 |
| WO | WO-2005/110528 | 11/2005 |
| WO | WO-2005/123183 | 12/2005 |
| WO | WO-2006/007048 | 1/2006 |
| WO | WO-2006/018528 | 2/2006 |
| WO | WO-2006/022790 | 3/2006 |
| WO | WO-2006/031899 | 3/2006 |
| WO | WO-2006041847 | 4/2006 |
| WO | WO-2006041881 | 4/2006 |
| WO | WO-2007008954 | 1/2007 |
| WO | WO-2007035537 | 3/2007 |
| WO | WO-2007078997 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008061150 | 5/2008 |
| WO | WO-2008061152 | 5/2008 |
| WO | WO-2008070413 | 6/2008 |
| WO | WO-2010078175 | 7/2010 |

OTHER PUBLICATIONS

Kandzari, D. E. et al.. (2012), Catheter-Based Renal Denervation for Resistant Hypertension: Rationale and Design of the Symplicity HTN-3 Trial. Clin Cardiol, 35, 528-535.*
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.

(56) References Cited

OTHER PUBLICATIONS

"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards™" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dubuc, M., et al., "Feasibility of cardiac cryoablation using a transvenous steerable electrode catheter." J Intery Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing The Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Intery Radiol, 12: 862-868 (2001).
Hansen, J. M., et al. "The transplanted human kidney does not achieve functional reinnervation." Clin. Sci, 87: 13-19 (1994).
Hendee, W. R. et al. "Use of Animals in Biomedical Research: The Challenge and Response." American Medical Association White Paper (1988) 39 pages.
Hering, Dagmara et al., "Chronic kidney disease: role of sympathetic nervous system activation and potential benefits of renal denervation." EuroIntervention, vol. 9, 2013, 9 pages.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S. J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D. L., et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).

(56) References Cited

OTHER PUBLICATIONS

Ormiston, John et al., "First-in-human use of the OneShot™ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J. F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
U.S. Appl. No. 60/813,589, filed Dec. 29, 2005, Demarais et al.
2003 European Society of Hypertension—European Society of Cardiology guidelines for the management of arterial hypertension, Guidelines Committee, Journal of Hypertension 2003, vol. 21, No. 6, pp. 1011-1053.
Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.
Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, Dec. 16, 2008, pp. 1.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): pp. 754-758.
Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.
Allen, E.V., Sympathectomy for essential hypertension, Circulation, 1952, 6:131-140.
Amersham Health. Hypaque-Cysto, 2003, 6 pages.
Andrews, B.T. et al., The use of surgical sympathectomy in the treatment of chronic renal pain. Br J Urol. 1997; 80: 6-10.
Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.
Archer, Steffen et al., Cell Reactions to Dielectrophoretic Manipulation, Mar. 1, 1999, Biochemical and Biophysical Research Communications, 1999 Academic Press, pp. 687-698.
Arentz, T. et al., Incidence of pulmonary vein stenosis 2 years after radiofrequency catheter ablation of refractory atrial fibrillation. European Heart Journal. 2003. 24; pp. 963-969.
Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.
Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.
Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.

(56) References Cited

OTHER PUBLICATIONS

Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.
Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.
Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.
Badyal, D. K., H. Lata and A.P. Dadhich, Animal Models of Hypertension and Effect of Drugs, Aug. 19, 2003, Indian Journal of Pharmacology 2003, vol. 35, pp. 349-362.
Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.
Balazs, Tibor, Development of Tissue Resistance to Toxic Effects of Chemicals, Jan. 26, 1974, Toxicology, 2 (1974), Elsevier/North-Holland, Amsterdam, pp. 247-255.
Barajas, L. Innervation of the renal cortex. Fex Proc. 1978;37:1192-201.
Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.
Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.
Bassett, C. Andrew L. et al., Augmentation of Bone Repair by Inductively Coupled Electromagnetic Fields, May 3, 1974, Science, vol. 184, pp. 575-577.
Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.
Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.
Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.
Bello-Reuss, E. et al., Acute unilateral renal denervation in rats with extracellular volume expansion, Departments of Medicine and Physiology, University of North Carolina School of Medicine. F26-F32 Jul. 1975.
Bello-Reuss, E. et al., Effect of renal sympathetic nerve stimulation on proximal water and sodium reabsorption, J Clin Invest, 1976;57:1104-1107.
Bello-Reuss, E. et al., Effects of Acute Unilateral Renal Denervation in the Rat, J Clin Invest, 1975;56:208-217.
Berde, C. et al., Local Anesthetics, Anesthesia, Chapter 13, 5th addition, Churchill-Livingston, Philadelphia 2000, pp. 491-521.
Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.
Bhandari, A. and Ellias, M., Loin pain hematuria syndrome: Pain control with RFA to the Splanchanic plexus, The Pain Clinic, 2000, vol. 12, No. 4, pp. 323-327.
Bhatt, Deepak L. et al., Rhabdomyolysis Due to Pulsed Electric Fields, May 11, 1989, Plastic and Reconstructive Surgery Jul. 1990, pp. 1-11.

Bichet, D., et al., Renal intracortical blood flow and renin secretion after denervation by 6-hydroxydopamine. Can J Physiol Pharmacol. 1982;60:184-92.
Bigler, D. et al., Tachyphylaxis during postoperative epidural analgesia—new insights, Apr. 15, 1987, Letter to the Editor, Acta Anaesthesiol Scand. 1987, vol. 31, pp. 664-665.
Binder, Allan et al., Pulsed Electromagnetic Field Therapy of Persistent Rotator Cuff Tendinitis, The Lancet, Saturday Mar. 31, 1984, The Lancet Ltd., pp. 695-698.
Black, M.D., Henry R., Resistant Hypertension 2004, presentation at Rush University Medical Center, Jul. 15, 2004, 40 pages.
Blad, B., et al., An Electrical Impedance index to Assess Electroporation in Tissue, Tissue and Organ (Therapy), 2001, Oslo, www.bl.uk <http://www.bl.uk> British Library, pp. 31-34.
Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.
Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.
Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.
Bourge, R.C., Heart Failure Monitoring Devices: Rationale and Status 28 pages, Feb. 2001.
Braunwald, E., Heart Disease, A Textbook of Cardiovascular Medicine, 5th Ed., vol. 2, 1997, pp. 480-481, 824-825, 1184-1288 and 1923-1925, W.B. Saunders Company.
Bravo, E.L., et al., Renal denervation for resistant hypertension, American Journal of Kidney Diseases, 2009, 3 pgs.
Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;115:1999-2005.
Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.
Campese, V.M. et al., Renal Afferent Denervation Prevents the Progression of Renal Disease in the Renal Ablation Model of Chronic Renal Failure in the Rat, Am J Kidney Dis. 1995;26:861-5.
Campese, V.M., A new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.

(56) References Cited

OTHER PUBLICATIONS

Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, 1997 WB Saunders Company, pp. 480-481.
Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment for Chronic Heart Failure: Electrical Modulation of Myocardial Contractility. Transcatheter Cardiovascular Therapeutics 2005, 21 slides.
Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
Clinical Trials in Hypertension and Renal Diseases, Slide Source, www.hypertensiononline.org, 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.
Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Curtis, J.J. et al., Surgical theray for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.
Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.
Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.
Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
Dibona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
Dibona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.
Dibona, Gerald F. and Ulla C. Kopp, Neural Control of Renal Function, Physiological Reviews, vol. 77, No. 1, Jan. 1997, the American Physiological Society 1997, pp. 75-197.
Dibona, Gerald F. and Ulla C. Kopp, Role of the Renal Sympathetic Nerves in Pathophysiological States, Neural Control of Renal Function, vol. 77, pp. 142-197 Jan. 1997.
Dibona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
Dibona, Gerald F., L.L. Sawin, Effect of renal nerve stimulation on NaCl and H2O transport in Henle's loop of the rat,: 1982, American Physiological Society, F576-F580, 5 pgs.
Dibona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
Dibona, Gerald F., Neural Control of the Kidney—Past, Present and Future, Nov. 4, 2002, Novartis Lecture, Hypertension 2003, 41 part 2, 2002 American Heart Association, Inc., pp. 621-624.
DiBona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
DiBona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
DiBona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.

(56) References Cited

OTHER PUBLICATIONS

DiBona, Gerald F., Sympathetic Nervous System and the Kidney in Hypertension, Current Opinion in Nephrology and Hypertension 2002, vol. 11, 2002 Lippincott Williams & Wilkins, pp. 197-200.
DiBona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.
DiBona, Gerald, LL Sawin, Effect of renal denervation on dynamic autoregulation of renal blood flow, Feb. 12, 2004, AmJ Physiol Renal Physiol 286, pp. F1209-F1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.
Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 (Apr. 2000), National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, A Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev Arat-Ozkan, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; dated Jan. 19, 2010, 4 pgs.
European Examination Report; European Patent Application No. 09156661.2; Applicant: Ardian, Inc.; dated Jan. 19, 2010, 6 pgs.
European Search Report; European Patent Application No. 05806045.0; Applicant: Ardian, Inc.; dated Sep. 22, 2009, 8 pgs.
European Search Report; European Patent Application No. 05811851.4; Applicant: Ardian, Inc.; dated Oct. 1, 2009, 7 pgs.
European Search Report; European Patent Application No. 06847926.0; Applicant: Ardian, Inc.; dated Feb. 10, 2010, 6 pgs.
European Search Report; European Patent Application No. 07757925.8; Applicant: Ardian, Inc.; dated Apr. 29, 2010, 9 pgs.
European Search Report; European Patent Application No. 07798341.9; Applicant: Ardian, Inc.; dated Aug. 4, 2011; 6 pgs.
European Search Report; European Patent Application No. 07799148.7; Applicant: Ardian, Inc.; dated Jul. 23, 2009, 6 pgs.
European Search Report; European Patent Application No. 07868755.5; Applicant: Ardian, Inc.; dated Jul. 28, 2010, 7 pgs.
European Search Report; European Patent Application No. 09156661.2; Applicant: Ardian, Inc.; dated Jul. 23, 2009, 6 pgs.
European Search Report; European Patent Application No. 09167937.3; Applicant: Ardian, Inc.; dated Nov. 11, 2009, 6 pgs.
European Search Report; European Patent Application No. 09168202.1; Applicant: Ardian, Inc.; dated Nov. 11, 2009, 5 pgs.
European Search Report; European Patent Application No. 09168204.7; Applicant: Ardian, Inc.; dated Nov. 19, 2009, 6 pgs.
Evelyn, K.A. et al., Effect of thoracolumbar sympathectomy on the clinical course of primary (essential) hypertension, Am J Med, 1960;28:188-221.
*Ex parte Quayle Office Action*; U.S. Appl. No. 11/144,173; dated May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.
Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.
Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; dated Jan. 29, 2009, 11 pgs.
Final Office Action; U.S. Appl. No. 11/266,993; dated Jan. 8, 2010, 7 pgs.
Final Office Action; U.S. Appl. No. 11/363,867; dated May 1, 2009, 8 pgs.
Final Office Action; U.S. Appl. No. 11/451,728; dated Jan. 13, 2009, 7 pgs.
Final Office Action; U.S. Appl. No. 11/599,649; dated Jan. 15, 2009, 10 pgs.
Final Office Action; U.S. Appl. No. 11/599,723; dated Apr. 5, 2010, 17 pgs.
Final Office Action; U.S. Appl. No. 11/599,890; dated Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.
Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.

(56) References Cited

OTHER PUBLICATIONS

Gattone II, Vincent H. et al., Contribution of Renal Innervation to Hypertension in Polycystic Kidney Disease in the Rat, University of Chicago Section of Urology, 16 pages, Mar. 17, 2008.
Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.
Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.
Getts, R.T. et al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to TENS in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., The outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update. pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.
Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
Heart Disease and Stroke Statistics—2004 Update, American Heart Association, American Stroke Association, Dallas, Texas, 2003 American Heart Association, 52 pgs.
Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104(4): 771-786.
Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.
Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.
Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.
Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.
Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.
Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.
Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.
Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.
Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.
Hypertension and Renal Disease: Mechanisms, Slide Show by www.hypertensiononline.org, 22 pages Mar. 30, 2001.
Hypertension Incidence and Prevalence, Age-Specific Rates, by Gender, B.C., 2001/2002, Graph, Chronic Disease Management, May 2003, British Columbia Ministry of Health Services, 1 page.
Implantable Neurostimulation Systems, Medtronic Neurological, Jan. 18, 1999, 6 pages. http://medtronic.com/neuro/paintherapies/pain_treatment_ladder/pdf/implantable_brochure.pdf.
Implantable Pump—The Medtronic MiniMed 2007 Implantable Insulin Pump System, Medtronic MiniMed 2004, 4 pgs.

(56) References Cited

OTHER PUBLICATIONS

International Search Report and Written Opinion for PCT/US2009/069334; Applicant: Ardian, Inc.; dated Mar. 1, 2010, 10 pgs.
International Search Report and Written Opinion, PCT/US05/35693, dated Mar. 8, 2006, Applicant: Ardian, Inc., 29 pgs.
International Search Report and Written Opinion, PCT/US05/35757, dated Dec. 27, 2006, Applicant: Ardian, Inc., 8 pgs.
International Search Report and Written Opinion, PCT/US06/36120, dated Jun. 25, 2008, Applicant: Ardian, Inc., 10 pgs.
International Search Report and Written Opinion, PCT/US06/41889, dated Oct. 20, 2008, Applicant: Ardian, Inc., 7 pgs.
International Search Report and Written Opinion, PCT/US06/48822, dated Aug. 15, 2008, Applicant: Ardian, Inc., 12 pgs.
International Search Report and Written Opinion, PCT/US07/63322, dated Mar. 3, 2008, Applicant: Ardian, Inc., 10 pgs.
International Search Report and Written Opinion, PCT/US07/63324, dated Oct. 10, 2008, Applicant: Ardian, Inc., 10 pgs.
International Search Report and Written Opinion, PCT/US07/66539, dated Jan. 28, 2008, Applicant: Ardian, Inc., 6 pgs.
International Search Report and Written Opinion, PCT/US07/70799, dated Jul. 2, 2008, Applicant: Ardian, Inc., 7 pgs.
International Search Report and Written Opinion, PCT/US07/72396, dated Aug. 27, 2008, Applicant: Ardian, Inc., 9 pgs.
International Search Report and Written Opinion, PCT/US07/84701, dated Aug. 21, 2008, Applicant: Ardian, Inc., 11 pgs.
International Search Report and Written Opinion, PCT/US07/84705, dated Jul. 28, 2008, Applicant: Ardian, Inc., 12 pgs.
International Search Report and Written Opinion, PCT/US07/84708, dated Aug. 11, 2008, Applicant: Ardian, Inc., 9 pgs.
International Search Report, PCT/US02/0039, dated Sep. 11, 2002, Applicant: Advanced Neuromodulation Systems, Inc.
International Search Report, PCT/US02/25712, dated Apr. 23, 2003, Applicant: Cyberonics, Inc.
International Search Report, PCT/US03/08014, dated Sep. 23, 2003, Applicant: The General Hospital Corporation.
International Search Report, PCT/US03/09764, dated Oct. 28, 2003, Applicant: CVRX, Inc.
International Search Report, PCT/US04/38498, dated Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia, Jianping et al.., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.
Johansson, Bjorn, Electrical Membrane Breakdown, A Possible Mediator of the Actions of Electroconvulsive Therapy, Medical Hypotheses 1987, vol. 24, Longman Group UK Ltd 1987, pp. 313-324.
Joles, J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Joye, James D.et al., In Vivo Study of Endovascular Cryotherapy for the Prevention of Restenosis, 4 pages, 2003.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II): II-166-II-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F14.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.

(56) References Cited

OTHER PUBLICATIONS

Kopp, U.C. et al., Renal sympathetic nerve activity modulates afferent renal nerve activity by PGE2-dependent activation of alpha1- and alpha2-adrenoceptors on renal sensory nerve fibers. Am J Physiol Regul Integr Comp Physiol. 2007;293:R1561-72.

Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.

Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.

Kumagai, K. et al. New Approach to Pulmonary Vein Isolation for Atrial Fibrillation Using a Multielectrode Basket Catheter. Circulation Journal. 2006;70:88-93.

Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.

Lavie, Peretz, Ph.D. and Victor Hoffstein, M.D., Sleep Apnea Syndrome: A Possible Contributing Factor to Resistant Hypertension, Jun. 2001, SLEEP 2001, vol. 24, No. 6, pp. 721-725.

Le Noble, J.L. et al., Pharmacological evidence for rapid destruction of efferent renal nerves in rats by intrarenal infusion of 6-hydroxydopamine. J Hypertens Suppl. 1985;3:S137-40.

Lee, Michael A. (editor). SPORTSMed. Connecticut State Medical Society Committee on the Medical Aspects of Sports. Fall/Winter 2005. 10 pgs.

Lee, Raphael C. et al., Biophysical Injury Mechanisms in Electronic Shock Trauma, Annu. Rev. Biomed. Eng., 2000, vol. 2, Copyright © 2000 by Annual Reviews, pp. 477-509.

Lee, Raphael C. et al., Clinical Sequelae Manifested in Electrical Shock Survivors, Presentation by the Electrical Trauma Research Program, The University of Chicago, 37 pages Dec. 24, 2004.

Lee, Raphael C. et al., Membrane Biology and Biophysics, Chapter 25, Surgical Research, 2001 Academic Press, pp. 297-305.

Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.

Lenoble, L.M. et al., Selective efferent chemical sympathectomy of rat kidneys. Am J Physiol. 1985;249:R496-501.

Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.

Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.

Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.

Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.

Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.

Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.

Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.

Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.

Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.

Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.

Luippold, G. et al., Chronic renal denervation prevents glomerular hyperfiltration in diabetic rats, Nephrol Dial Transplant (2004) 19:342-347.

Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.

Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.

Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.

Mancia, G., Grassi, G., Giannattasio, C., Seravalle, G., Sympathetic acrivation of pathogenesis of hypertension and progression of organ damage, Hypertension 1999, 34 (4 Pt 2): 724-728.

Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.

Market for infusion pumps grows with an aging population, NWL 97-01, The BBI Newsletter, vol. 20, No. 2, Feb. 1, 1997, American Health Consultants, Inc., pp. 6.

Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.

McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.

Mccullough, Peter A., M.D., MPH et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.

McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.

Mcrobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.

Medtronic Neurostimulation Systems, Expanding the Array of Pain Control Solutions, informational pamphlet, 1999 Medtronic, Inc., 6 pages.

Medtronic, Spinal Cord Stimulation, Patient Management Guidelines for Clinicians, Medtronic, Inc. 1999, 115 pages.

Medtronic, SynchroMed Infusion System—Clinical Reference Guide for Pain Therapy, Medtronic, Inc. 1998, 198 pages.

Mehran, Roxana, Renal insufficiency and contrast nephropathy: The most common, least understood risk factor, Cardiovascular Research Foundation, Columbia University Medical Center, 2005, 86 slides.

Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.

Micro ETS Hyperhidrosis USA Hyperhidrosis USA. 2 pgs. <URL: http://www.hyperhidrosis-usa.com/Index.html>. Nov. 6, 2006.

(56) References Cited

OTHER PUBLICATIONS

Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. ½, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine HCI) Injection, RX only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You At Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; dated Mar. 21, 2006, 14 pgs.
Non-Final Office Action; U.S. Appl. No. 11/129,765; dated May 18, 2007, 10 pgs.
Non-Final Office Action; U.S. Appl. No. 11/129,765; dated Sep. 10, 2007, 5 pgs.
Non-Final Office Action; U.S. Appl. No. 11/129,765; dated Oct. 6, 2006, 30 pgs.
Non-Final Office Action; U.S. Appl. No. 11/133,925; dated Oct. 8, 2008, 41 pgs.
Non-Final Office Action; U.S. Appl. No. 11/144,173; dated Apr. 5, 2007, 33 pgs.
Non-Final Office Action; U.S. Appl. No. 11/144,173; dated Sep. 10, 2007, 5 pgs.
Non-Final Office Action; U.S. Appl. No. 11/144,298; dated Oct. 29, 2009, 8 pgs.
Non-Final Office Action; U.S. Appl. No. 11/144,298; dated Apr. 5, 2007, 33 pgs.
Non-Final Office Action; U.S. Appl. No. 11/144,298; dated Sep. 10, 2007, 5 pgs.
Non-Final Office Action; U.S. Appl. No. 11/144,298; dated Dec. 29, 2008, 7 pgs.
Non-Final Office Action; U.S. Appl. No. 11/145,122; dated Apr. 11, 2007, 33 pgs.
Non-Final Office Action; U.S. Appl. No. 11/145,122; dated Sep. 10, 2007, 5 pgs.
Non-Final Office Action; U.S. Appl. No. 11/189,563; dated May 28, 2009, 5 pgs.
Non-Final Office Action; U.S. Appl. No. 11/233,814; dated Jun. 17, 2008, 12 pgs.
Non-Final Office Action; U.S. Appl. No. 11/252,462; dated Feb. 22, 2010, 6 pgs.
Non-Final Office Action; U.S. Appl. No. 11/266,993; dated Jul. 8, 2009, 5 pgs.
Non-Final Office Action; U.S. Appl. No. 11/266,993; dated Dec. 30, 2008, 7 pgs.
Non-Final Office Action; U.S. Appl. No. 11/363,867; dated Sep. 25, 2008, 10 pgs.
Non-Final Office Action; U.S. Appl. No. 11/368,553; dated May 18, 2010, 4 pgs.
Non-Final Office Action; U.S. Appl. No. 11/368,553; dated Oct. 7, 2009, 5 pgs.
Non-Final Office Action; U.S. Appl. No. 11/368,809; dated Dec. 3, 2009, 4 pgs.
Non-Final Office Action; U.S. Appl. No. 11/368,949; dated Jun. 11, 2010, 6 pgs.
Non-Final Office Action; U.S. Appl. No. 11/368,971; dated Aug. 24, 2010, 9 pgs.
Non-Final Office Action; U.S. Appl. No. 11/451,728; dated Jun. 12, 2008, 41 pgs.
Non-Final Office Action; U.S. Appl. No. 11/451,728; dated Jul. 2, 2009, 5 pgs.
Non-Final Office Action; U.S. Appl. No. 11/451,728; dated Dec. 28, 2009, 7 pgs.
Non-Final Office Action; U.S. Appl. No. 11/504,117; dated Mar. 31, 2009, 10 pgs.
Non-Final Office Action; U.S. Appl. No. 11/599,649; dated Mar. 30, 2009, 10 pgs.
Non-Final Office Action; U.S. Appl. No. 11/599,649; dated Jun. 23, 2008, 9 pgs.
Non-Final Office Action; U.S. Appl. No. 11/599,723; dated Jun. 26, 2009, 17 pgs.
Non-Final Office Action; PU.S. Appl. No. 11/599,723; dated Oct. 15, 2010, 16 pgs.
Non-Final Office Action; U.S. Appl. No. 11/599,882; dated Jul. 6, 2009, 13 pgs.
Non-Final Office Action; U.S. Appl. No. 11/688,178; dated Jun. 28, 2010, 5 pgs.
Non-Final Office Action; U.S. Appl. No. 11/840,142; dated Apr. 3, 2009, 13 pgs.
Non-Final Office Action; U.S. Appl. No. 12/567,521; dated Sep. 3, 2010, 9 pgs.
Non-Final Office Action; U.S. Appl. No. 12/616,708; dated Sep. 16, 2010, 10 pgs.
Non-Final Office Action; U.S. Appl. No. 12/725,375; dated Oct. 12, 2010, 14 pgs.
Nozawa, T.et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1935;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.

(56) References Cited

OTHER PUBLICATIONS

Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al, The Histologic Effects of Pulsed and Continuous Radiofrequency Lesions at 42 C to Rat Dorsal Root Ganglion and Sciatic Nerve, Spine, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.

Renal Parenchymal Disease, Ch. 26, 5th Edition Heart Disease, A Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen, S.M. et al., Relationship of Vascular Reactivity to Plasma Renin Concentration in Patients with Terminal Renal Failure, Proc. Dialysis Transplant Forum 1974, pp. 45-47.
Roth, Bradley J. And Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.
Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Catheter ablation of cardiac autonomic nerves for prevention of vagal atrial fibrillation, Circulation. 102(22). Nov. 28, 2000. Abstract only. 2 pgs.
Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.
Scheiner, Avram, Ph.D., The design, development and implementation of electrodes used for functional electrial stimulation, Thesis paper, Case Western Reserve University, May 1992, 220 pages.
Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.
Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic

(56) References Cited

OTHER PUBLICATIONS

Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32 . . . An Implantable Bolus Infusion Pump for the Neurosciences, FRP, Apr. 2005, 3 pages.
Sensorcaine—MPF Spinal Injection, informational document, AstraZeneca 2001, 2 pgs.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shupak, Naomi M., Therapeutic Uses of Pulsed Magnetic-Field Exposure: A Review, Radio Science Bulletin Dec. 2003, No. 307, pp. 9-32.
Shu-Qing, Liu et al., Old spinal cord injury treated by pulsed electric stimulation, General Hospital of Beijing Command, Beijing, Dec. 6, 1990, 5 pages (full article in Chinese; abstract on last page).
Siegel, RJ et al., Clinical demonstration that catheter-delivered ultrasound energy reverses arterial vasoconstriction, Journal of the American College of Cardiology. 1992. 20; 732-735. Summary only. 2 pgs.
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006.
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.
Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Hypertension and associated cardiovascular disease: comparison of male and female mortality rates and their influence on selection of therapy, JAMA, 1956, 160:1023-1033.
Smithwick, R.H. et al., Splanchnicectomy for essential hypertension, Journal Am Med Assn, 1953;152:1501-1504.
Smith Wick, R.H., Surgical treatment of hypertension, Am J Med 1948, 4:744-759.

Sobotka, Paul A., Treatment Strategies for Fluid Overload, CHF Patients, CHF Solutions. Transcatheter Cardiovascular Therapeutics 2005. 20 slides.
Solis-Herruzo, J.A. et al., Effects of lumbar sympathetic block on kidney function in cirrhotic patients with hepatorenal syndrome, Journal of Hepatology, 1987; 5: 167-173.
Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.
Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.
Steffen, W. et al., Catheter-delivered high intensity, low frequency ultrasound induces vasodilation in vivo, European Heart Journal. 1994. 15; pp. 369-376.
Steg, PG et al., Pulsed ultraviolet laser irradiation produces endothelium-independent relaxation of vascular smooth muscle, Circulation: Journal of the American Heart Association. 1989. pp. 189-197.
Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.
Strojek, K. et al., Lowering of microalbuminuria in diabetic patients by a sympathicoplegic agent: novel approach to prevent progression of diabetic nephropathy? J Am Soc Nephrol. 2001;12:602-5.
Summary, Critical Reviews in Biomedical Engineering, vol. 17, Issue 5, 1989, pp. 515-529.
Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.
Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.
Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.
Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.
Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.
Terashima, Mitsuyasu et al. Feasibility and Safety of a Novel CryoPlasty™ System. Poster. 1 page, Mar. 15, 2002.
Thatipelli et al., CT Angiography of Renal Artery Anatomy for Evaluating Embolic Protection Devices, Journal of Vascular and Interventional Radiology, Jul. 2007, pp. 842-846.
The Antihypertensive and Lipid-Lowering Treatment to Prevent Heart Attack Trial, ALLHAT Research Group, JAMA, 2002, vol. 288, pp. 2981-2997.
Thomas, John R. and Oakley, E. Howard N. Chapter 15: Nonfreezing Cold Injury Medical Aspects of Harsh Environments, vol. 1. pp. 467-490, 2001.
Thompson, Gregory W., et al., Bradycardia Induced by Intravascular Versus Direct Stimulation of the Vagus Nerve, Aug. 24, 1997, The Society of Thoracic Surgeons 1998, pp. 637-642.
Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.
Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.
Trapani, Angelo J. et al., Neurohumoral interactions in conscious dehydrated rabbit, Am. J. Physiol. 254, 1988, the American Physiological Society 1988, pp. R338-R347.

(56) References Cited

OTHER PUBLICATIONS

Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.
Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.
Trumble, Dennis R. and James A. MaGovern, Comparison of Dog and Pig Models for Testing Substernal Cardiac Compression Devices, Nov. 2003, ASAIO Journal 2004, pp. 188-192.
Tsai, E., Intrathecal drug delivery for pain indications, technique, results, Pain Lecture presentation, Jun. 8, 2001, 31 pages.
Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.
Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.
Van Antwerp, Bill and Poonam Gulati, Protein Delivery from Mechanical Devices Challenges and Opportunities, Medtronic presentation, 19 pages, Jul. 2003.
Velazquez, Eric J., An international perspective on heart failure and left ventricular systolic dysfunction complicating myocardial infarction: the VALIANT registry, Aug. 5, 2004, European Heart Journal vol. 25, 2004 Elsevier, pp. 1911-1919.
Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.
Villarreal, Daniel et al., Effects of renal denervation on postprandial sodium excretion in experimental heart failure, Oct. 29, 1993, Am J Physiol 266, 1994, pp. R1599-R1604.
Villarreal, Daniel et al., Neurohumoral modulators and sodium balance in experimental heart failure, Nov. 6, 1992, Am. J. Physiol, vol. 264, 1993, pp. H1187-H1193.
Vonend, O. et al., Moxonidine treatment of hypertensive patients with advanced renal failure. J Hypertens. 2003;21:1709-17.
Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.
Wald, Jan D., Ph.D, et al., Cardiology Update: 2003, Sep. 11, 2003, AG Edwards 2003, 120 pages.
Wang, Xi et al., Alterations of adenylyl cyclase and G proteins in aortocaval shunt-induced heart failure, Jul. 2004, AM J Physiol Heart Circ Physiol vol. 287, 2004 the American Physiological Society, pp. H118-H125.
Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.
Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.
Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, Oct. 1974, pp. 575-585.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.
Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D. et al., Prognostic Significance of Serum Creatinine Concentration for In-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.
Ye, Richard D., M.D., Ph.D., Pharmacology of the Peripheral Nervous System, E-425 MSB, 6 pages, Jan. 2000.
Ye, S. et al., A limited renal injury may cause a permanent form of neurogenic hypertension. Am J Hypertens. 1998;11:723-8.
Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.
Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.
Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.
Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.
Zanchetti, A. et al., Neural Control of the Kidney—Are There Reno-Renal Reflexes?, Clin. and Exper. Hyper. Theory and Practice, A6 (1&2), 1984, Marcel Dekker, Inc. 1984, pp. 275-286.
Zanchetti, A. et al., Practice Guidelines for Primary Care Physicians: 2003 ESH/ESC Hypertension Guidelines, Journal of Hypertension, vol. 21, No. 10, 2003, pp. 1779-1786.
Zanchetti, A.S., Neural regulation of renin release: Experimental evidence and clinical implications in arterial hypertension, Circulation, 1977, 56(5) 691-698.
Zimmermann, Ulrich, Electrical Breakdown, Electropermeabilization and Electrofusion, Rev. Physiol. Biochem. Pharmacol., vol. 105, Springer-Verlag 1986, pp. 175-256.
Zoccali, C. et al., Plasma norepinephrine predicts survival and incident cardiovascular events in patients with end-stage renal disease. Circulation. 2002;105:1354-9.
Zucker, Irving H. et al., The origin of sympathetic outflow in heart failure: the roles of angiotensin II and nitric oxide, Progress in Biophysics & Molecular Biology, vol. 84, 2004, Elsevier Ltd. 2003, pp. 217-232.
Zundert, Jan Van, M.D. FIPP and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.

\* cited by examiner

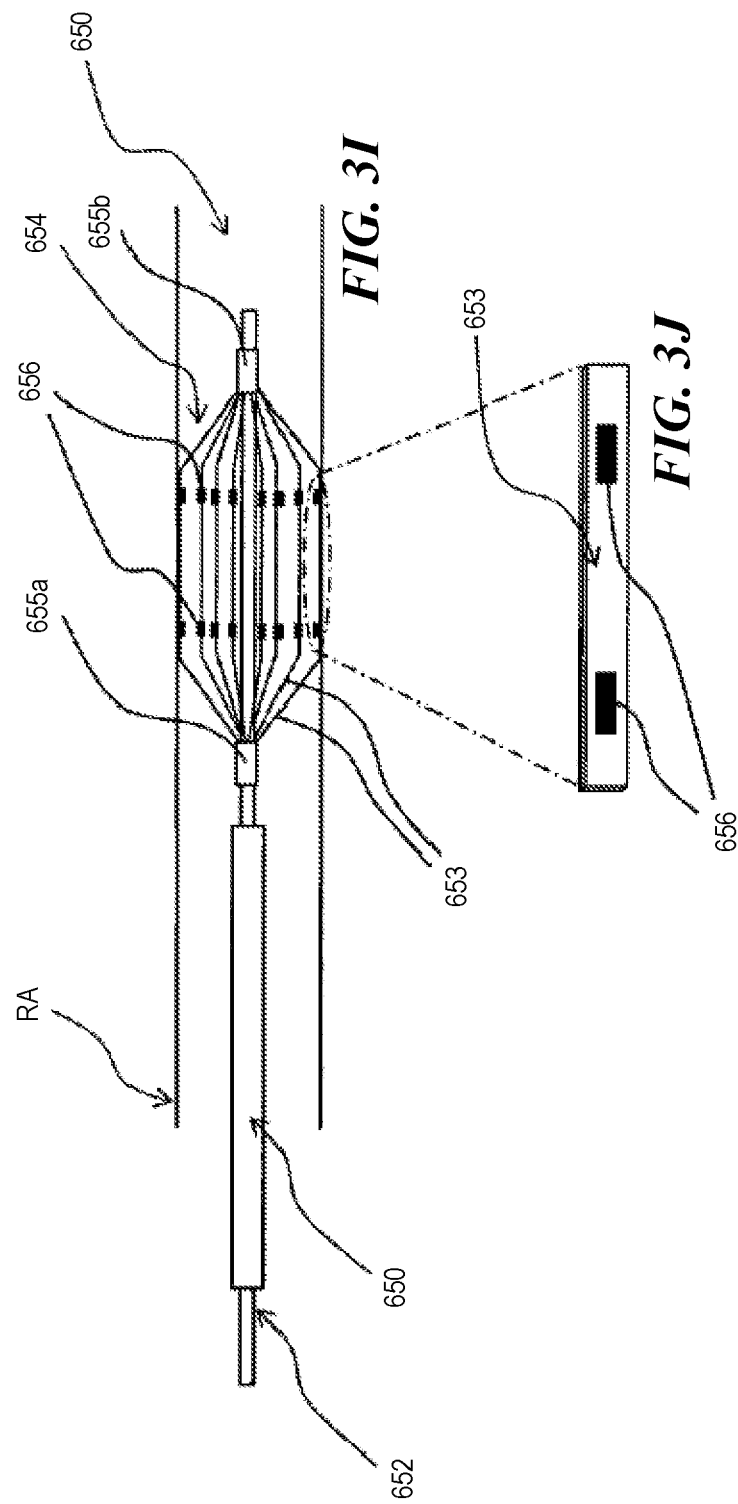

FIG. 4C

Baseline Patient Characteristics

| | All Patients (N = 1000) | SBP ≥160 mm Hg & Ambulatory SBP ≥135* mm Hg (N = 327) |
|---|---|---|
| Gender, (% male) | 61.2% | 63.9% |
| Age (years) | 60.7 ± 12.0 | 61.0 ± 10.9 |
| BMI (kg/m²) | 30.5 ± 5.5 | 30.9 ± 5.5 |
| Current smoking | 10.0% | 11.0% |
| History of cardiac disease | 50.5% | 52.9% |
| Renal impairment (eGFR <60 ml/min/1.73m²) | 23.4% | 27.9% |
| Sleep apnea (AHI≥5) | 4.2% | 5.9% |
| Diabetes, Type 1 | 3.2% | 2.5% |
| Diabetes, Type 2 | 38.5% | 42.6% |
| 1 co-morbidity | 39.7% | 36.7% |
| 2 co-morbidities | 35.5% | 34.6% |
| 3+ co-morbidities | 24.6% | 28.4% |

*FIG. 21B*

Antihypertensive Medication Use

| | All Patients<br>(N = 1000) | SBP ≥160 mm Hg &<br>Ambulatory SBP ≥135 mm Hg*<br>(N = 327) |
|---|---|---|
| Antihypertensive medication classes | 4.5 ± 1.3 | 4.7 ± 1.2 |
| Beta-blockers | 78.9% | 81.0% |
| ACE inhibitors | 33.8% | 38.5% |
| Angiotensin-receptor blockers | 67.3% | 67.9% |
| Calcium channel blockers | 76.3% | 78.9% |
| Diuretics | 78.2% | 79.8% |
| Aldosterone antagonists | 21.1% | 19.3% |
| Spironolactone | 18.6% | 15.9% |
| Alpha adrenergic blockers | 35.2% | 40.1% |
| Direct-acting vasodilators | 15.1% | 19.0% |
| Centrally acting sympatholytics | 33.2% | 37.6% |
| Direct renin inhibitor | 7.4% | 7.7% |

*FIG. 21C*

Procedural Detail

| | |
|---|---|
| # renal arteries | 2.2 ± 0.5 |
| Length | 41.5 ± 13.1 mm |
| Diameter left renal artery | 5.6 ± 1.2 mm |
| Diameter right renal artery | 5.7 ± 1.2 mm |
| Treatment time | 50 min |
| # bilateral ablations | 13.5 ± 4.1 |
| # 120 sec bilateral ablations | 11.3 ± 3.4 |
| Contrast volume used | 127.6 ± 81.1 cc | values are mean ± SD

*FIG. 21D*

Safety at 1 and 6 Months

| | 1 Month n=967 | 6 Month n=913 |
|---|---|---|
| Cardiovascular events | | |
| Cardiovascular death | 0.0% (0) | 0.2% (2) |
| Stroke | 0.2% (2) | 0.9% (8) |
| Hospitalization for new onset heart failure | 0.3% (3) | 0.7% (6) |
| Hospitalization for atrial fibrillation | 0.1% (1) | 0.9% (8) |
| Hypertensive crisis/emergency | 0.2% (2) | 1.0% (9) |
| Myocardial infarction | 0.0% (0) | 0.6% (5) |
| Renal events | | |
| New onset end stage renal disease | 0.1% (1) | 0.2% (2) |
| Serum creatinine elevation > 50% | 0.1% (1) | 0.2% (2) |
| New renal artery stenosis >70% | 0.0% (0) | 0.0% (0) |
| Post-procedural events | | |
| Non-cardiovascular death | 0.0% (0) | 0.2% (2) |
| Renal artery re-intervention | 0.1% (1) | 0.2% (2) |
| Vascular complication | 0.4% (4) | 0.4% (4) |

*FIG. 21E*

METHODS FOR CATHETER-BASED RENAL NEUROMODULATION

CROSS-REFERENCE TO RELATED APPLICATIONS

This application claims the benefit of the following applications:

U.S. Provisional Patent Application No. 61/967,873, filed Mar. 28, 2014;
U.S. Provisional Patent Application No. 61/967,874, filed Mar. 28, 2014;
U.S. Provisional Patent Application No. 61/967,875, filed Mar. 28, 2014;
U.S. Provisional Patent Application No. 61/967,876, filed Mar. 28, 2014;
U.S. Provisional Patent Application No. 61/967,877, filed Mar. 28, 2014;
U.S. Provisional Patent Application No. 61/967,880, filed Mar. 28, 2014;
U.S. Provisional Patent Application No. 61/967,888, filed Mar. 28, 2014;
U.S. Provisional Patent Application No. 61/967,891, filed Mar. 28, 2014;
U.S. Provisional Patent Application No. 62/018,919, filed Jun. 30, 2014;
U.S. Provisional Patent Application No. 62/049,770, filed Sep. 12, 2014;
U.S. Provisional Patent Application No. 62/050,083, filed Sep. 13, 2014;
U.S. Provisional Patent Application No. 62/056,658, filed Sep. 29, 2014;
U.S. Provisional Patent Application No. 62/056,659, filed Sep. 29, 2014;
U.S. Provisional Patent Application No. 62/060,627, filed Oct. 7, 2014;
U.S. Provisional Patent Application No. 62/068,262, filed Oct. 24, 2014;
U.S. Provisional Patent Application No. 62/101,939, filed Jan. 9, 2015;
U.S. Provisional Patent Application No. 62/101,936, filed Jan. 9, 2015;
U.S. Provisional Patent Application No. 62/102,128, filed Jan. 12, 2015.

All of the foregoing applications are incorporated herein by reference in their entireties. Further, components and features of embodiments disclosed in the applications incorporated by reference may be combined with various components and features disclosed and claimed in the present application.

TECHNICAL FIELD

The present technology relates generally to methods and systems for catheter-based renal neuromodulation. In particular, several embodiments are directed to treatment of hypertension and/or improving one or more measurable physiological parameters corresponding to hypertension using renal neuromodulation and associated systems and methods.

BACKGROUND

The sympathetic nervous system (SNS) is a primarily involuntary bodily control system typically associated with stress responses. Fibers of the SNS extend through tissue in almost every organ system of the human body. For example, some fibers extend from the brain, intertwine along the aorta, and branch out to various organs. As groups of fibers approach specific organs, fibers particular to the organs can separate from the groups. Signals sent via these and other fibers can affect characteristics such as pupil diameter, gut motility, and urinary output. Such regulation can have adaptive utility in maintaining homeostasis or in preparing the body for rapid response to environmental factors. Chronic activation of the SNS, however, is a common maladaptive response that can drive the progression of many disease states. Excessive activation of the renal SNS in particular has been identified experimentally and in humans as a likely contributor to the complex pathophysiology of hypertension, states of volume overload (such as heart failure), and progressive renal disease. As examples, radiotracer dilution has demonstrated increased renal norepinephrine (NE) spillover rates in patients with essential hypertension.

Sympathetic nerves of the kidneys terminate in the blood vessels, the juxtaglomerular apparatus, and the renal tubules. Stimulation of the renal sympathetic nerves can cause increased renin release, increased sodium ($Na^+$) reabsorption, and a reduction of renal blood flow. These neural regulation components of renal function are considerably stimulated in disease states characterized by heightened sympathetic tone as well as likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure). Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II calcium channel blockers), vasodilators (to counteract peripheral vasoconstriction caused by increased sympathetic drive), aldosterone blockers (to block the actions of increased aldosterone released from activation of the renin-angiotensin-aldosterone system (RAAS) and aldosterone activation consequent to renin release), and diuretics (intended to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present disclosure can be better understood with reference to the following drawing(s). The components in the drawings are not necessarily to scale. Instead, emphasis is placed on illustrating clearly the principles of the present disclosure.

FIG. 3I is a schematic side-view, partially in section, of an intravascular device having an expandable basket and a plurality of electrodes at the basket in accordance with another embodiment of the technology.

FIG. 3J is a schematic detail view of the apparatus of FIG. 3I illustrating one embodiment of the electrodes in accordance with another embodiment of the technology.

FIGS. 21A-24 are display diagrams illustrating baseline data and corresponding results from another study to determine the effects of renal denervation in a real world population of 1000 human patients with uncontrolled hypertension.

DETAILED DESCRIPTION

Figure 1:
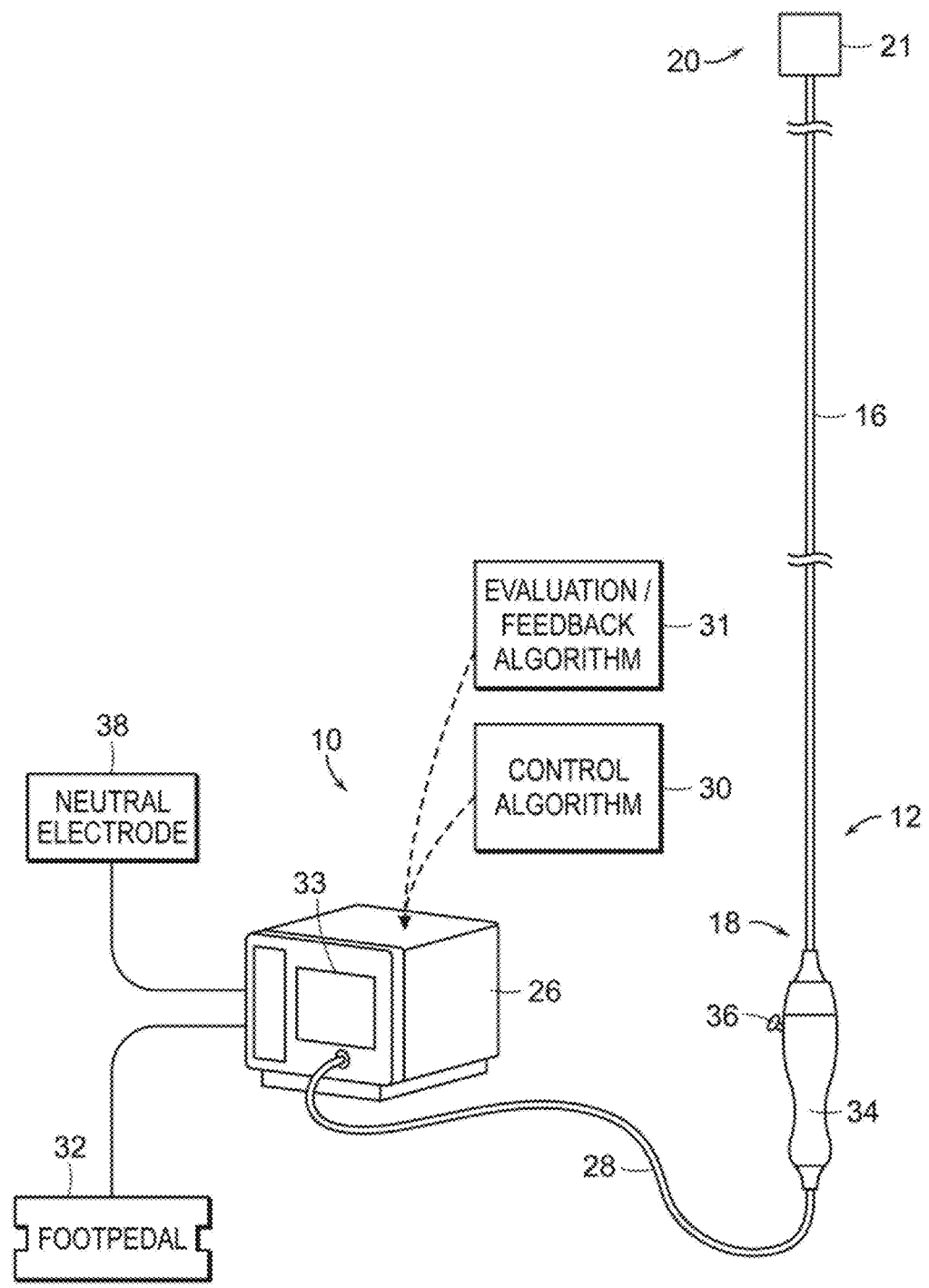
FIG. 1 illustrates an intravascular neuromodulation system configured in accordance with an embodiment of the present technology.

The present technology is directed to apparatuses, systems, and methods for treating hypertension and/or improving one or more measurable physiological parameters corresponding to hypertension using renal neuromodulation. For example, some embodiments include performing therapeutically-effective renal neuromodulation on a patient diagnosed with hypertension. As discussed in greater detail below, renal neuromodulation can include rendering neural fibers inert, inactive, or otherwise completely or partially reduced in function. This result can be electrically-induced, thermally-induced, or induced by another mechanism during a renal neuromodulation procedure, e.g., a procedure including percutaneous transluminal intravascular access.

Specific details of several embodiments of the technology are described below with reference to FIGS. 1-24. Although many of the embodiments are described herein with respect to electrically-induced, thermally-induced, and chemically-induced approaches, other treatment modalities in addition to those described herein are within the scope of the present technology. Additionally, several other embodiments of the technology can have different configurations, components, or procedures than those described herein. A person of ordinary skill in the art, therefore, will accordingly understand that the technology can have other embodiments with additional elements and that the technology can have other embodiments without several of the features shown and described below with reference to FIGS. 1-24.

As used herein, the terms "distal" and "proximal" define a position or direction with respect to the treating clinician or clinician's control device (e.g., a handle assembly). "Distal" or "distally" can refer to a position distant from or in a direction away from the clinician or clinician's control device. "Proximal" and "proximally" can refer to a position near or in a direction toward the clinician or clinician's control device.

I. RENAL NEUROMODULATION

Renal neuromodulation is the partial or complete incapacitation or other effective disruption of nerves innervating the kidneys. In particular, renal neuromodulation can include inhibiting, reducing, and/or blocking neural communication along neural fibers (i.e., efferent and/or afferent nerve fibers) innervating the kidneys. Such incapacitation can be long-term (e.g., permanent or for periods of months, years, or decades) or short-term (e.g., for periods of minutes, hours, days, or weeks). While long-term disruption of the renal nerves can be desirable for alleviating symptoms and other sequelae associated with hypertension over longer periods of time, short-term modulation of the renal nerves may also be desirable. For example, some patients may benefit from short-term modulation to address acute symptoms of hypertension.

Intravascular devices that reduce sympathetic nerve activity by applying, for example, RF energy to a target site in the renal artery have recently been shown to reduce blood pressure in patients with resistant hypertension. For purposes of this disclosure, a person has "resistant hypertension" when that person's systolic blood pressure remains at or above 140 mm Hg despite adherence to at least three maximally tolerated doses of antihypertension medications from complementary classes, including a diuretic at an appropriate dose.

The renal sympathetic nerves arise from T10-L2 and follow the renal artery to the kidney. The sympathetic nerves innervating the kidneys terminate in the blood vessels, the juxtaglomerular apparatus, and the renal tubules. Stimulation of renal efferent nerves results in increased renin release (and subsequent RAAS activation) and sodium retention and decreased renal blood flow. These neural regulation components of renal function are considerably stimulated in disease states characterized by heightened sympathetic tone and likely contribute to increased blood pressure in hypertensive patients. The reduction of renal blood flow and glomerular filtration rate as a result of renal sympathetic efferent stimulation is likely a cornerstone of the loss of renal function in cardio-renal syndrome (i.e., renal dysfunction as a progressive complication of chronic heart failure).

Various techniques can be used to partially or completely incapacitate neural pathways, such as those innervating the kidney. The purposeful application of energy (e.g., electrical energy, thermal energy) to tissue can induce one or more desired thermal heating and/or cooling effects on localized regions along all or a portion of the renal artery and adjacent regions of the renal plexus RP, which lay intimately within or adjacent to the adventitia of the renal artery. Some embodiments of the present technology, for example, include electrode-based or transducer-based approaches, which can be used for therapeutically-effective renal neuromodulation. For example, an energy delivery element (e.g., electrode) can be configured to deliver electrical and/or thermal energy at a treatment site. Suitable energy modalities can include, for example, radiofrequency (RF) energy (monopolar and/or bipolar), pulsed RF energy, microwave energy, ultrasound energy (e.g., intravascularly delivered ultrasound, extracorporeal ultrasound, high-intensity focused ultrasound (HIFU)), laser, optical energy, magnetic energy, direct heat, radiation (e.g., infrared, visible, gamma), or other suitable energy modalities alone or in combination. Where a system uses a monopolar configuration, a return electrode or ground patch fixed externally on the subject can be used. Further, electrodes (or other energy delivery elements) can be used alone or with other electrodes in a multi-electrode array. Examples of suitable multi-electrode devices are described in U.S. patent application Ser. No. 13/281,360, filed Oct. 25, 2011, and incorporated herein by reference in its entirety. Other suitable devices and technologies are described in U.S. patent application Ser. No. 13/279,330, filed Oct. 23, 2011, U.S. Provisional Patent App. No. 61/968,310, filed Mar. 20, 2014, and U.S. Provisional Patent App. No. 61/932,213, filed Jan. 27, 2014. Additional thermal devices are described in U.S. patent application Ser. No. 13/279,205, filed Oct. 21, 2011. All of the foregoing patent references are incorporated herein by reference in their entireties.

In some embodiments, a treatment procedure can include applying a suitable treatment modality at a treatment location in a testing step followed by a treatment step. The testing step, for example, can include applying the treatment modality at a lower intensity and/or for a shorter duration than during the treatment step. This can allow an operator to determine (e.g., by neural activity sensors and/or patient feedback) whether nerves proximate the treatment location are suitable for modulation. Performing a testing step can be particularly useful for treatment procedures in which targeted nerves are closely associated with nerves that could cause undesirable side effects if modulated during a subsequent treatment step.

II. SELECTED EXAMPLES OF NEUROMODULATION MODALITIES

Complete or partial renal neuromodulation in accordance with embodiments of the present technology can be electrically-induced, thermally-induced, chemically-induced, or induced in another suitable manner or combination of manners at one or more suitable locations during a treatment procedure. For example, neuromodulation may be achieved using various modalities, including for example monopolar or bipolar radio frequency (RF) energy, pulsed RF energy, microwave energy, laser light or optical energy, magnetic energy, ultrasound energy (e.g., intravascularly delivered ultrasound, extracorporeal ultrasound, high-intensity focused ultrasound (HIFU)), direct heat energy, or cryotherapeutic energy, chemicals (e.g., drugs or other agents), or combinations thereof. In certain embodiments, neuromodulation may utilize one or more devices including, for example, catheter devices such as the Symplicity™ catheter (Medtronic, Inc.). Other suitable thermal devices are described in U.S. Pat. No. 7,653,438, U.S. Pat. No. 8,347,891, and U.S. patent application Ser. No. 13/279,205, filed Oct. 21, 2011, and examples of suitable multi-electrode devices are described in U.S. patent application Ser. No. 13/281,360, filed Oct. 25, 2011, and U.S. Pat. No. 8,888,773. Other examples of suitable direct heat devices are described in U.S. Provisional Patent Application No. 61/789,113 filed Mar. 15, 2013, and U.S. patent application Ser. No. 14/203,933, filed Mar. 11, 2014. The disclosures of these applications are incorporated herein by reference in their entireties.

In those embodiments of the methods disclosed herein that utilize partial ablation, the level of energy delivered to the renal artery and surrounding tissue may be different than the level that is normally delivered for complete neuromodulation. For example, partial neuromodulation using RF energy may use alternate algorithms or different power levels than RF energy for complete neuromodulation. Alternatively, partial neuromodulation methods may utilize the same level of energy, but delivered to a different depth within the tissue or to a more limited area. In certain embodiments, partial neuromodulation may be achieved using a device that differs from a device used for complete neuromodulation. In certain embodiments, a particular treatment or energy modality may be more suitable for partial neuromodulation than other treatment or energy modalities.

In some embodiments, neuromodulation may be achieved using one or more chemical agents, such as by drug delivery. In those embodiments that utilize partial neuromodulation, the methods may utilize the same devices and/or drug delivery systems used for complete neuromodulation, or they may use completely different devices for energy and/or drug delivery.

Thermal effects can include both thermal ablation and non-ablative thermal alteration or damage (e.g., via sustained heating and/or resistive heating) to partially or completely disrupt the ability of a nerve to transmit a signal. Such thermal effects can include the heating effects associated with electrode-based or transducer-based treatment. For example, a treatment procedure can include raising the temperature of target neural fibers to a target temperature above a first threshold to achieve non-ablative alteration, or above a second, higher threshold to achieve ablation. In some embodiments, the target temperature can be higher than about body temperature (e.g., about 37° C.) but less than about 45° C. for non-ablative alteration, and the target temperature can be higher than about 45° C. for ablation. More specifically, heating tissue to a temperature between about body temperature and about 45° C. can induce non-ablative alteration, for example, via moderate heating of target neural fibers or vascular/luminal structures that perfuse the target neural fibers. In cases where vascular structures are affected, the target neural fibers can be denied perfusion resulting in necrosis of the neural tissue. For example, this may induce non-ablative thermal alteration in the fibers or structures. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C., e.g., less than about 85° C., less than about 80° C., or less than about 75° C. Other embodiments can include heating tissue to a variety of other suitable temperatures.

In some embodiments, complete or partial renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, as mentioned above, neuromodulation in accordance with embodiments of the present technology can include delivering monopolar or bipolar RF energy, pulsed RF energy, microwave energy, laser light or optical energy, ultrasound energy (e.g., intravascularly delivered ultrasound, extracorporeal ultrasound, HIFU), magnetic energy, direct heat energy, or another suitable type of energy alone or in combination. In some embodiments, renal neuromodulation can be conducted in conjunction with one or more other tissue modulation procedures. An element, transducer, or electrode used to deliver this energy can be used alone or with other elements, transducers, or electrodes in a multi-element array. Furthermore, the energy can be applied from within the body (e.g., within the vasculature or other body lumens in a catheter-based approach or outside the vasculature using, for example, a Natural Orifice Transluminal Endoscopic Surgery or NOTES procedure) and/or from outside the body, e.g., via an applicator positioned outside the body. In some embodiments, energy can be used to reduce damage to non-targeted tissue when targeted tissue adjacent to the non-targeted tissue is subjected to neuromodulating cooling.

As an alternative to or in conjunction with electrode-based or transducer-based approaches, other suitable energy delivery techniques, such as a cryotherapeutic treatment modality, can be used for achieving therapeutically-effective renal neuromodulation. For example, cryotherapeutic treatment can include cooling tissue at a treatment location in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death, e.g., during tissue thawing and subsequent hyperperfusion. Neuromodulation using a cryotherapeutic treatment in accordance with embodiments of the present technology can include cooling a structure proximate an inner surface of a vessel or chamber wall such that tissue is effectively cooled to a depth where sympathetic renal nerves reside. For example, a cooling assembly of a cryotherapeutic device can be cooled to the extent that it causes therapeutically-effective, cryogenic renal neuromodulation. In some embodiments, a cryotherapeutic treatment modality can include cooling that is not configured to cause neuromodulation. For example, the cooling can be at or above cryogenic temperatures and can be used to control neuromodulation via another treatment modality, e.g., to protect tissue from neuromodulating energy. Other suitable cryotherapeutic devices are described, for example, in U.S. patent application Ser. No. 13/279,330, filed Oct. 23, 2011, and incorporated herein by reference in its entirety.

Cryotherapeutic treatment can be beneficial in certain embodiments. For example, rapidly cooling tissue can provide an analgesic effect such that cryotherapeutic treatment can be less painful than other treatment modalities. Neuromodulation using cryotherapeutic treatment can therefore require less analgesic medication to maintain patient comfort during a treatment procedure compared to neuromodulation using other treatment modalities. Additionally, reducing pain can reduce patient movement and thereby increase operator success and/or reduce procedural complications. Cryogenic cooling also typically does not cause significant collagen tightening, and therefore is not typically associated with vessel stenosis. In some embodiments, cryotherapeutic treatment can include cooling at temperatures that can cause therapeutic elements to adhere to moist tissue. This can be beneficial because it can promote stable, consistent, and continued contact during treatment. The typical conditions of treatment can make this an attractive feature because, for example, patients can move during treatment, catheters associated with therapeutic elements can move, and/or respiration can cause the kidneys to rise and fall and thereby move the renal arteries and other structures associated with the kidneys. In addition, blood flow is pulsatile and can cause structures associated with the kidneys to pulse. Cryogenic adhesion also can facilitate intravascular or intraluminal positioning, particularly in relatively-small structures (e.g., relatively-short arteries) in which stable intravascular or intraluminal positioning can be difficult to achieve.

The use of ultrasound energy can be beneficial in certain embodiments. Focused ultrasound is an example of a transducer-based treatment modality that can be delivered from outside the body (i.e., extracorporeal). In some embodiments, focused ultrasound treatment can be performed in close association with imaging, e.g., magnetic resonance, computed tomography, fluoroscopy, ultrasound (e.g., intravascular or intraluminal), optical coherence tomography, or another suitable imaging modality. For example, imaging can be used to identify an anatomical position of a treatment location, e.g., as a set of coordinates relative to a reference point. The coordinates can then be entered into a focused ultrasound device configured to change the distance from source to target, power, angle, phase, or other suitable parameters to generate an ultrasound focal zone at the location corresponding to the coordinates. In some embodiments, the focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight). In certain embodiments, the ultrasound device may be a catheter device with an ultrasound transducer or an array of ultrasound transducers on its distal tip. In other embodiments the ultrasound device may comprise a cylindrical transducer. In certain embodiments wherein the ultrasound device is being used to perform partial ablation, the device may include discrete and/or forward-facing transducers that can be rotated and inserted at specific conditions, thereby allowing for more discrete lesion formation. In other embodiments, however, the extracorporeal and/or intravascular ultrasound devices may have different arrangements and/or different features.

In some embodiments, renal neuromodulation can be effected using a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. In some embodiments, the chemical can be guanethidine, vincristine, ethanol, phenol, a neurotoxin, or another suitable agent selected to alter, damage, or disrupt nerves. In some embodiments, energy (e.g., light, ultrasound, or another suitable type of energy) can be used to activate the chemical and/or to cause the chemical to become more bioavailable. A variety of suitable techniques can be used to deliver chemicals to tissue at a treatment location. For example, chemicals can be delivered via one or more needles originating outside the body or within the vasculature or other body lumens (see, e.g., U.S. Pat. No. 6,978,174, the disclosure of which is hereby incorporated by reference in its entirety). In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a vessel wall, electrophoresis, or another suitable mechanism. Similar techniques can be used to introduce chemicals that are not configured to cause neuromodulation, but rather to facilitate neuromodulation via another treatment modality. Examples of such chemicals include, but are not limited to, anesthetic agents and contrast agents.

Renal neuromodulation in conjunction with the methods and devices disclosed herein may be carried out at a location proximate (e.g., at or near) a vessel or chamber wall (e.g., a wall of a renal artery, one or more branch vessels from the renal artery, a ureter, a renal pelvis, a major renal calyx, a minor renal calyx, and/or another suitable structure), and the treated tissue can include tissue proximate the treatment location. For example, with regard to a renal artery, a treatment procedure can include modulating nerves in the renal plexus, which lay intimately within or adjacent to the adventitia of the renal artery.

In certain embodiments, the efficacy of partial neuromodulation may be monitored by measuring the levels of one or more biomarkers associated with neuromodulation including, for example, proteins or non-protein molecules that exhibit an increase or decrease in level or activity in response to neuromodulation (see, e.g., International Patent App. No. PCT/US2013/030041, filed Mar. 8, 2013, the disclosure of which is incorporated herein by reference in its entirety).

III. SELECTED EMBODIMENTS OF RENAL NEUROMODULATION SYSTEMS AND DEVICES

FIG. 1 illustrates a renal neuromodulation system 10 configured in accordance with an embodiment of the present technology. The system 10, for example, may be used to perform therapeutically-effective renal neuromodulation on a patient diagnosed with hypertension. The system 10 includes an intravascular treatment device 12 operably coupled to an energy source or console 26 (e.g., RF energy generator, a cryotherapy console). In the embodiment shown in FIG. 1, the treatment device 12 (e.g., a catheter) includes an elongated shaft 16 having a proximal portion 18, a handle 34 at a proximal region of the proximal portion 18, and a distal portion 20 extending distally relative to the proximal portion 18. The treatment device 12 further includes a neuromodulation assembly or treatment section 21 at the distal portion 20 of the shaft 16. The neuromodulation assembly 21 can include one or more electrodes or energy-delivery elements, a cryotherapeutic cooling assembly and/or a nerve monitoring device configured to be delivered to a renal blood vessel (e.g., a renal artery) in a low-profile configuration.

In one embodiment, for example, the neuromodulation assembly 21 can include a single electrode. In other embodiments, the neuromodulation assembly 21 may comprise a basket and a plurality of electrodes carried by the basket. The electrodes on the basket may be spaced apart from each other such that each electrode is approximately 90° apart from a neighboring electrode. In yet another embodiment, the neuromodulation assembly 21 can include a balloon and a plurality of bipolar electrodes carried by the balloon. In still another embodiment, the neuromodulation assembly 21 has a plurality of electrodes arranged along an elongated member transformable between a low-profile, delivery configuration (e.g., contained in a delivery catheter) and an expanded, deployed configuration in which the elongated member has a helical/spiral shape. In any of the foregoing embodiments, the neuromodulation assembly 21 may comprise one or more irrigated electrodes.

Upon delivery to a target treatment site within a renal blood vessel, the neuromodulation assembly 21 can be further configured to be deployed into a treatment state or arrangement for delivering energy at the treatment site and providing therapeutically-effective electrically-induced and/or thermally-induced renal neuromodulation. In some embodiments, the neuromodulation assembly 21 may be placed or transformed into the deployed state or arrangement via remote actuation, e.g., via an actuator 36, such as a knob, pin, or lever carried by the handle 34. In other embodiments, however, the neuromodulation assembly 21 may be transformed between the delivery and deployed states using other suitable mechanisms or techniques.

The proximal end of the neuromodulation assembly 21 can be carried by or affixed to the distal portion 20 of the elongated shaft 16. A distal end of the neuromodulation assembly 21 may terminate with, for example, an atraumatic rounded tip or cap. Alternatively, the distal end of the neuromodulation assembly 21 may be configured to engage another element of the system 10 or treatment device 12. For example, the distal end of the neuromodulation assembly 21 may define a passageway for engaging a guide wire (not shown) for delivery of the treatment device using over-the-wire ("OTW") or rapid exchange ("RX") techniques. The treatment device 12 can also be a steerable or non-steerable catheter device (e.g., a guide catheter) configured for use without a guide wire. Body lumens (e.g., ducts or internal chambers) can be treated, for example, by non-percutaneously passing the shaft 16 and neuromodulation assembly 21 through externally accessible passages of the body or other suitable methods.

The console 26 can be configured to generate a selected form and magnitude of energy for delivery to the target treatment site via the neuromodulation assembly 21. A control mechanism, such as a foot pedal 32, may be connected (e.g., pneumatically connected or electrically connected) to the console 26 to allow an operator to initiate, terminate and, optionally, adjust various operational characteristics of the console 26, including, but not limited to, power delivery. The system 10 may also include a remote control device (not shown) that can be positioned in a sterile field and operably coupled to the neuromodulation assembly 21. The remote control device can be configured to allow for selective activation of the neuromodulation assembly 21. In other embodiments, the remote control device may be built into the handle assembly 34. The energy source 26 can be configured to deliver the treatment energy via an automated control algorithm 30 and/or under the control of the clinician. In addition, the energy source 26 may include one or more evaluation or feedback algorithms 31 to provide feedback to the clinician before, during, and/or after therapy.

The energy source 26 can further include a device or monitor that may include processing circuitry, such as a microprocessor, and a display 33. The processing circuitry may be configured to execute stored instructions relating to the control algorithm 30. The energy source 26 may be configured to communicate with the treatment device 12 (e.g., via a cable 28) to control the neuromodulation assembly and/or to send signals to or receive signals from the nerve monitoring device. The display 33 may be configured to provide indications of power levels or sensor data, such as audio, visual or other indications, or may be configured to communicate information to another device. For example, the console 26 may also be configured to be operably coupled to a catheter lab screen or system for displaying treatment information, such as nerve activity before and/or after treatment.

In certain embodiments, a neuromodulation device for use in the methods disclosed herein may combine two or more energy modalities. For example, the device may include both a hyperthermic source of ablative energy and a hypothermic source, making it capable of, for example, performing both RF neuromodulation and cryo-neuromodulation. The distal end of the treatment device may be straight (for example, a focal catheter), expandable (for example, an expanding mesh or cryoballoon), or have any other configuration. For example, the distal end of the treatment device can be at least partially helical/spiral in the deployed state. Additionally or alternatively, the treatment device may be configured to carry out one or more non-ablative neuromodulatory techniques. For example, the device may comprise a means for diffusing a drug or pharmaceutical compound at the target treatment area (e.g., a distal spray nozzle).

IV. SELECTED EXAMPLES OF TREATMENT PROCEDURES FOR RENAL NEUROMODULATION

Figure 2:
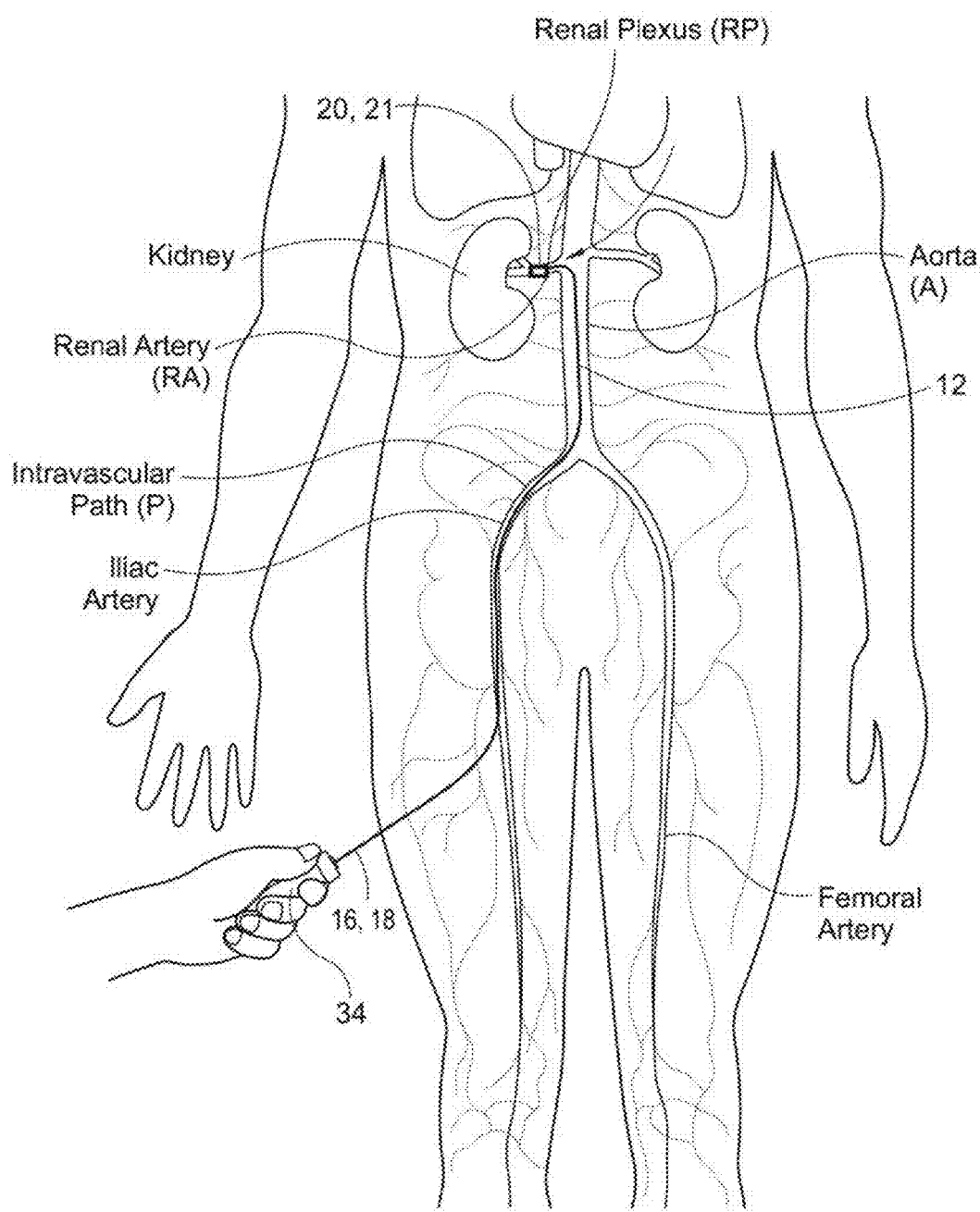
FIG. 2 illustrates modulating renal nerves with a neuromodulation system configured in accordance with an embodiment of the present technology.

FIG. 2 illustrates modulating renal nerves with an embodiment of the system 10 (FIG. 1). The treatment device 12 provides access to the renal plexus RP through an intravascular path P, such as a percutaneous access site in the femoral (illustrated), brachial, radial, or axillary artery to a targeted treatment site within a respective renal artery RA. As illustrated, a section of the proximal portion 18 of the shaft 16 is exposed externally of the patient. By manipulating the proximal portion 18 of the shaft 16 from outside the intravascular path P, the clinician may advance the shaft 16 through the sometimes tortuous intravascular path P and remotely manipulate the distal portion 20 of the shaft 16. Image guidance, e.g., computed tomography (CT), fluoroscopy, intravascular ultrasound (IVUS), optical coherence tomography (OCT), or another suitable guidance modality, or combinations thereof, may be used to aid the clinician's manipulation. Further, in some embodiments, image guidance components (e.g., IVUS, OCT) may be incorporated into the treatment device 12. In some embodiments, the shaft 16 and the neuromodulation assembly 21 can be 3, 4, 5, 6, or 7 French or another suitable size. Furthermore, the shaft 16 and the neuromodulation assembly 21 can be partially or fully radiopaque and/or can include radiopaque markers corresponding to measurements, e.g., every 5 cm.

After the neuromodulation assembly 21 is adequately positioned in the renal artery RA, it can be radially expanded or otherwise deployed using the handle 34 or other suitable control mechanism until the neuromodulation assembly is positioned at its target site and in stable contact with the inner wall of the renal artery RA. The purposeful application of energy from the neuromodulation assembly can then be applied to tissue to induce one or more desired neuromodulating effects on localized regions of the renal artery RA and adjacent regions of the renal plexus RP, which lay intimately within, adjacent to, or in close proximity to the adventitia of the renal artery RA. The neuromodulating effects may include denervation, thermal ablation, and non-ablative thermal alteration or damage (e.g., via sustained heating and/or resistive heating). The purposeful application of the energy may achieve neuromodulation along all or at least a portion of the renal plexus RP.

Figure 3A:
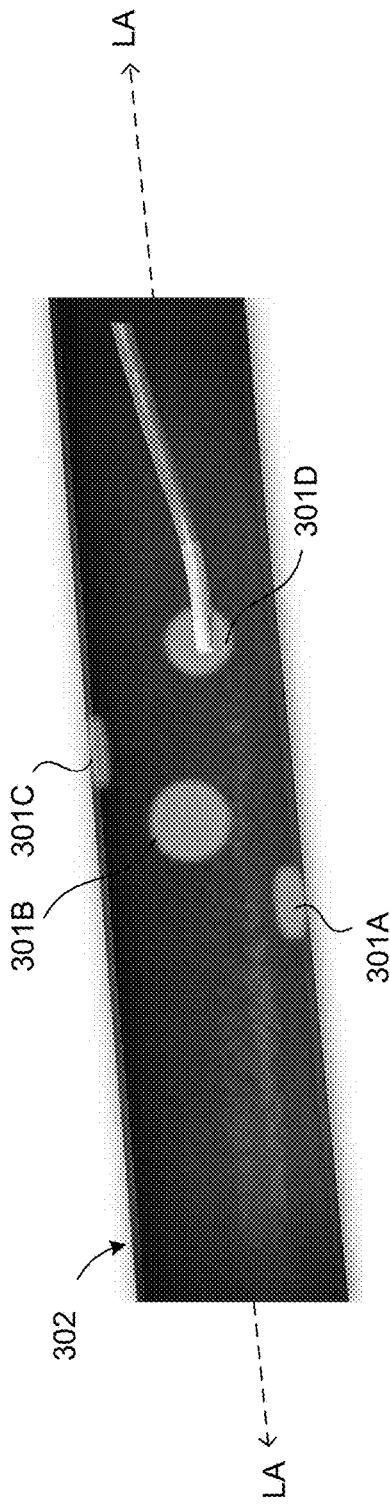
FIGS. 3A-3B illustrate a pattern of lesions that can be formed on the interior vessel wall in accordance with an embodiment of the present technology.
Figure 3B:
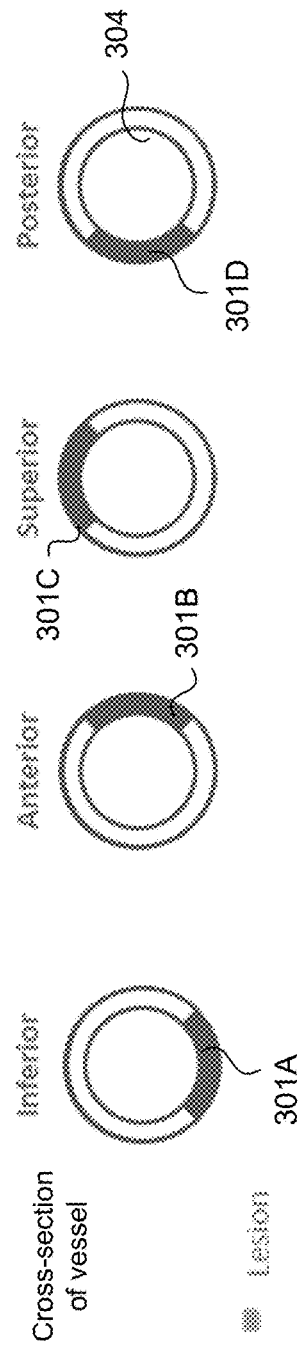

In the deployed state, the neuromodulation assembly 21 can be configured to contact an inner wall of a vessel of the renal vasculature and to form a suitable lesion or pattern of lesions without the need for repositioning. For example, the neuromodulation assembly 21 can be configured to form a single lesion or a series of lesions, e.g., overlapping and/or non-overlapping. In some embodiments, the lesion(s) (e.g., pattern of lesions) can extend around generally the entire circumference of the vessel, but can still be non-circumferential at longitudinal segments or zones along a lengthwise portion of the vessel. This can facilitate precise and efficient treatment with a low possibility of vessel stenosis. In other embodiments, the neuromodulation assembly 21 can be configured to form a partially-circumferential lesion or a fully-circumferential lesion at a single longitudinal segment or zone of the vessel. FIGS. 3A-3B, for example, illustrate a pattern of lesions that can be formed on the interior vessel wall along the lengthwise portion of the vessel in accordance with an embodiment of the present technology. For example, and in certain embodiments, the treatment locations 301 (individually identified as 301A-D) can be spaced apart from each other (e.g., by not less than approximately 5 mm) along a longitudinal axis LA of the vessel 302 (FIG. 3A). In some embodiments, the treatment locations 301 (e.g., location of lesions or ablation sites around a circumference of an interior vessel wall) can be arranged in a pattern around the wall 304 of the blood vessel 302 (such as a helical/spiral pattern—FIG. 3B). In certain embodiments, and as shown in FIG. 3B, a helical pattern can include at least one treatment location 301 in each of an inferior (301A), anterior (301B), superior (301C) and posterior (301D) position around the wall 304.

During treatment, the neuromodulation assembly 21 can be configured for partial or full occlusion of a vessel. Partial occlusion can be useful, for example, to reduce ischemia, while full occlusion can be useful, for example, to reduce interference (e.g., warming or cooling) caused by blood flow through the treatment location. In some embodiments, the neuromodulation assembly 21 can be configured to cause therapeutically-effective neuromodulation (e.g., using ultrasound energy) without contacting a vessel wall.

As mentioned previously, the methods disclosed herein may use a variety of suitable energy modalities, including RF energy, pulsed RF energy, microwave energy, laser, optical energy, ultrasound energy (e.g., intravascularly delivered ultrasound, extracorporeal ultrasound, HIFU), magnetic energy, direct heat, cryotherapy, radiation (e.g., infrared, visible, gamma), or a combination thereof. Alternatively or in addition to these techniques, the methods may utilize one or more non-ablative neuromodulatory techniques. For example, the methods may utilize non-ablative SNS neuromodulation by removal of target nerves (e.g., surgically), injection of target nerves with a destructive drug or pharmaceutical compound, or treatment of the target nerves with non-ablative energy modalities (e.g., laser or light energy). In certain embodiments, the amount of reduction of the sympathetic nerve activity may vary depending on the specific technique being used.

Furthermore, a treatment procedure can include treatment at any suitable number of treatment locations, e.g., a single treatment location, two treatment locations, or more than two treatment locations. In some embodiments, the number of treatment locations receiving ablation treatments in a renal artery can be 4-6 treatment locations, greater than 6 treatment locations, no less than 8 treatment locations, equal to or greater than 8 treatment locations, etc. In some embodiments, different treatment locations can correspond to different portions of the renal artery RA, the renal vein, and/or other suitable structures proximate tissue having relatively high concentrations of renal nerves. The shaft 16 can be steerable (e.g., via one or more pull wires, a steerable guide or sheath catheter, etc.) and can be configured to move the neuromodulation assembly 21 between treatment locations. At each treatment location, the neuromodulation assembly 21 can be activated to cause modulation of nerves proximate the treatment location. Activating the neuromodulation assembly 21 can include, for example, heating, cooling, stimulating, or applying another suitable treatment modality at the treatment location. Activating the neuromodulation assembly 21 can further include applying various energy modalities at varying power levels, intensities and for various durations for achieving modulation of nerves proximate the treatment location. In some embodiments, power levels, intensities and/or treatment duration can be determined and employed using various algorithms for ensuring modulation of nerves at select distances (e.g., depths) away from the treatment location. Furthermore, as noted previously, in some embodiments, the neuromodulation assembly 21 can be configured to introduce (e.g., inject) a chemical (e.g., a drug or other agent) into target tissue at the treatment location. Such chemicals or agents can be applied at various concentrations depending on treatment location and the relative depth of the target nerves.

As discussed, the neuromodulation assembly 21 can be positioned at a treatment location within the renal artery RA, for example, via a catheterization path including a femoral artery and the aorta, or another suitable catheterization path, e.g., a radial or brachial catheterization path. Catheterization can be guided, for example, using imaging, e.g., magnetic resonance, computed tomography, fluoroscopy, ultrasound, intravascular ultrasound, optical coherence tomography, or another suitable imaging modality. The neuromodulation assembly 21 can be configured to accommodate the anatomy of the renal artery RA, the renal vein, and/or another suitable structure. For example, the neuromodulation assembly 21 can include a balloon (not shown) configured to inflate to a size generally corresponding to the internal size of the renal artery RA, the renal vein, and/or another suitable structure. In some embodiments, the neuromodulation assembly 21 can be an implantable device and a treatment procedure can include locating the neuromodulation assembly 21 at the treatment location using the shaft 16, fixing the neuromodulation assembly 21 at the treatment location, separating the neuromodulation assembly 21 from the shaft 16, and withdrawing the shaft 16. Other treatment procedures for modulation of renal nerves in accordance with embodiments of the present technology are also possible.

Figure 3C:
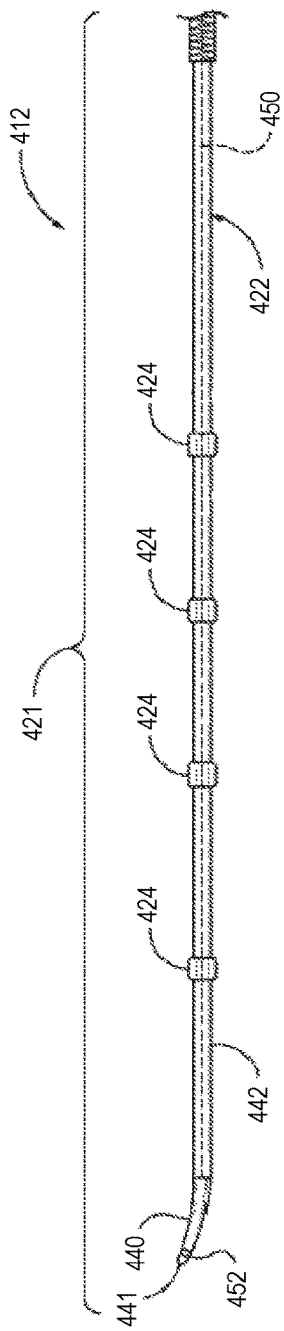
FIG. 3C is a side view of a distal portion of a catheter having a therapeutic assembly or treatment section in a delivery state (e.g., low-profile or collapsed configuration) outside a patient in accordance with an embodiment of the present technology.
Figure 3D:
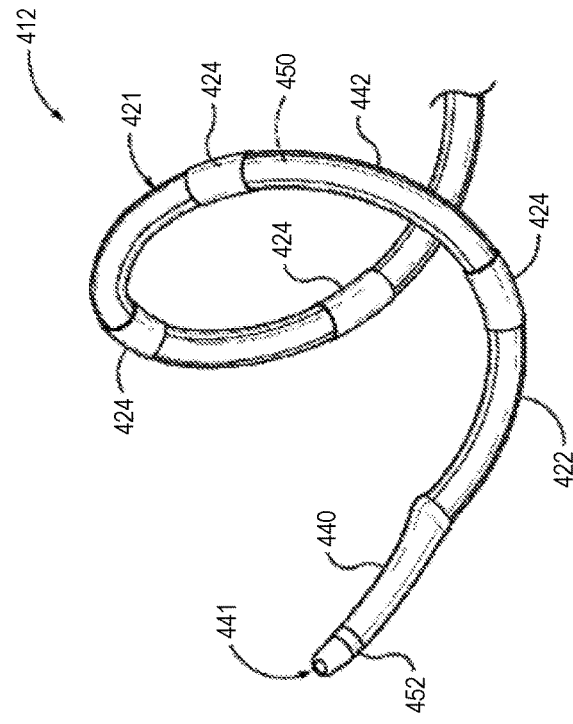
FIG. 3D is a perspective view of the distal portion of the catheter of FIG. 3C in a deployed state (e.g., expanded configuration) outside the patient.

FIG. 3C is a side view of a distal portion of a catheter 412 and a therapeutic assembly or treatment section 421 in a delivery state (e.g., low-profile or collapsed configuration) outside a patient, and FIG. 3D is a perspective view of the therapeutic assembly 421 in a deployed state (e.g., expanded configuration) outside the patient. As described previously, the catheter 412 may be configured for OTW delivery from an access site in which a guide wire (not shown) is initially inserted to a treatment site (e.g., within a renal artery), and the catheter 412 is installed over the guide wire. As described in greater detail below, a guide wire may be either inserted into or at least partially withdrawn from the distal portion to transform the therapeutic assembly 421 between the delivery state (FIG. 3C) and the deployed state (FIG. 3D). For example, as shown in FIG. 3C, a guide wire (not shown) extending through at least a portion of the length of the catheter 412 may be configured to straighten a pre-shaped spiral/helical control member 450 (shown schematically in broken lines) of the catheter 412 during delivery, and the guide wire may be at least partially withdrawn or slidably moved relative to the distal portion 420 to allow the therapeutic assembly 421 to transform to the deployed state (FIG. 3D).

As best seen in FIG. 3C, the therapeutic assembly 421 includes multiple (e.g., four, five, etc.) energy delivery elements 424 carried by support structure 422. In this embodiment, the support structure 422 comprises a flexible tube 442 and the pre-shaped control member 450 within the tube 442. The flexible tube 442 may be composed of a polymer material such as polyamide, polyimide, polyether block amide copolymer sold under the trademark PEBAX, polyethylene terephthalate (PET), polypropylene, aliphatic, polycarbonate-based thermoplastic polyurethane sold under the trademark CARBOTHANE, or a polyether ether ketone (PEEK) polymer that provides the desired flexibility. In other embodiments, however, the tube 442 may be composed of other suitable materials.

As mentioned above, the pre-shaped control member 450 may be used to provide a spiral/helical shape to the relatively flexible distal portion 420 of the catheter 412. As best seen in FIG. 3D, for example, the control member 450 is a tubular structure comprising a nitinol multifilar stranded wire with a lumen therethrough and sold under the trademark HELICAL HOLLOW STRAND (HHS), and commercially available from Fort Wayne Metals of Fort Wayne, Ind. The tubular control member 450 may be formed from a variety of different types of materials, may be arranged in a single or dual-layer configuration, and may be manufactured with a selected tension, compression, torque and pitch direction. The HHS material, for example, may be cut using a laser, electrical discharge machining (EDM), electrochemical grinding (ECG), or other suitable means to achieve a desired finished component length and geometry. For example, as best seen in FIG. 3D, the control member 450 in the present embodiment has a pre-set spiral/helical configuration that defines the deployed state of the therapeutic assembly 421 such that the energy delivery elements 424 of the therapeutic assembly 421 are offset from each other (e.g., both angularly and longitudinally offset relative to a longitudinal axis of the renal artery) and may be positioned in stable apposition with a wall of the renal artery (FIG. 2) for treatment. For purposes of clarification, the pre-set helical shape of the therapeutic assembly 421 in its deployed state may be defined by dimensions (e.g., helix diameter and pitch) that are distinct from the dimensions (e.g., helix diameter and pitch) of the HHS itself. In other words, the multifilar hollow tube forming control member 450 is itself pre-set into a helical shape.

Forming the control member 450 of nitinol multifilar stranded wire(s) or other similar materials is expected to eliminate the need for any additional reinforcement wire(s) or structures within the support structure 422 to provide a desired level of support and rigidity to the therapeutic assembly 421. This feature is expected to reduce the number of manufacturing processes required to form the catheter 412 and reduce the number of materials required for the device. Another feature of the therapeutic assembly 421 is that the control member 450 and inner wall of the tube 442 are in intimate contact and there is little or no space between the control member 450 and the tube 442. In one embodiment, for example, tube 442 can be expanded prior to assembly such that applying hot air to the tube 442 during the manufacturing process can shrink the tube onto the control member 450, as will be understood by those familiar with the ordinary use of shrink tubing materials. This feature is expected to inhibit or eliminate wrinkles or kinks that might occur in the tube 442 as the therapeutic assembly 421 transforms from the relatively straight delivery state to the deployed, generally helical state.

In other embodiments, the control member 450 and/or other components of the support structure 422 may be composed of different materials and/or have a different arrangement. For example, the control member 450 may be formed from other suitable shape memory materials (e.g., nickel-titanium (nitinol), wire or tubing besides HHS, shape memory polymers, electro-active polymers) that are pre-formed or pre-shaped into the desired deployed state. Alternatively, the control member 450 may be formed from multiple materials such as a composite of one or more polymers and metals.

The array of energy delivery elements 424 can include series of separate band electrodes spaced along the support structure 422 and bonded to the tube 442 using an adhesive. Band or tubular electrodes may be used in some embodiments, for example, because they typically have lower power requirements for ablation as compared to disc or flat electrodes. In other embodiments, however, disc or flat electrodes are also suitable. In still another embodiment, electrodes having a spiral or coil shape may be utilized. In some embodiments, the energy delivery elements 424 may be equally spaced apart along the length of the support structure 422. The energy delivery elements 424 may be formed from any suitable metallic material (e.g., gold, platinum, an alloy of platinum and iridium, etc.). In other embodiments, however, the number, arrangement, and/or composition of the energy delivery elements 424 may vary. Additional details regarding the catheter 412 and other examples of suitable multi-electrode devices are described in U.S. Pat. No. 8,888,773, which is incorporated herein by reference as noted previously.

FIGS. 3E-3H illustrate an apparatus 500 configured in accordance with another embodiment of the present technology. The apparatus 500, for example, includes a catheter 502 having an optional positioning element 504 (e.g., a balloon, an expandable wire basket, other mechanical expanders, etc.) and expandable electrode element 506 positioned along the shaft of the catheter and illustratively located over the positioning element. The electrode element 506 can have one or more electrodes 507 electrically coupled to a field generator 550 for delivery of an electric field to the target neural fibers. In an alternative embodiment, one or more of the electrode(s) 507 of the electrode element 506 may comprise Peltier electrodes for heating or cooling the target neural fibers to modulate the fibers. The electrode(s) 507 optionally may be individually assignable and may be utilized in a bipolar fashion, and/or may be utilized in a monopolar fashion with an external ground pad attached to the exterior of the patient.

The field generator 550, as well as any of the electrode embodiments described herein, may be utilized with any embodiment of the present technology for delivery of an electric field with desired field parameters. The field generator 550 can be external to the patient. It should be understood that electrodes of embodiments described hereinafter may be electrically connected to the generator even though the generator is not explicitly shown or described with each embodiment. Furthermore, the field generator optionally may be positioned internal to the patient, and the electrodes and/or the field generator optionally may be temporarily or permanently implanted within the patient.

The positioning element 504 optionally may position or otherwise drive the electrode(s) 507 into contact with the vessel wall. The positioning element 504 may also comprise an impedance-altering element that alters the impedance within the vessel during the therapy to direct the electric field across the vessel wall. This may reduce an energy required to achieve desired neuromodulation or denervation and may reduce a risk of injury to non-target tissue. Applicants have previously described use of an impedance-altering element, for example, in U.S. patent application Ser. No. 11/266,993, filed Nov. 4, 2005, which is incorporated herein by reference in its entirety. When the positioning element 504 comprises an inflatable balloon, as in FIGS. 3E-3H, the balloon may serve as both a centering and/or expansion element for the expandable electrode element 506, and as an impedance-altering electrical insulator for directing an electric field delivered via the electrode(s) 507 into or across the vessel wall for modulation of target neural fibers. Electrical insulation provided by the element 504 may reduce the magnitude of applied energy or other parameters of the electric field necessary to achieve desired modulation of the target fibers, up to and including full denervation of tissue containing the target fibers.

Furthermore, element 504 optionally may be utilized as a thermal element. For example, it may be inflated with a chilled fluid that serves as a heat sink for removing heat from tissue that contacts the element. Conversely, element 504 may be inflated with a warmed fluid that heats tissue in contact with the element. The thermal fluid within the element optionally may be circulated and/or exchanged within the positioning element 504 to facilitate more efficient conductive and/or convective heat transfer. Thermal fluids also may be used to achieve thermal neuromodulation via thermal cooling or heating mechanisms, as described in greater detail herein below.

The electrode(s) 507 can be individual electrodes (i.e., independent contacts), a segmented electrode with commonly connected contacts, or a single continuous electrode. Furthermore, the electrode(s) 507 may be configured to provide a bipolar signal, or the electrode(s) 507 may be used together or individually in conjunction with a separate patient ground pad for monopolar use. As an alternative or in addition to placement of the electrode(s) 507 along the expandable electrode element 506, as in FIGS. 3E and 3F, the electrode(s) 507 may be attached to the positioning element 504 such that they contact the wall of the artery upon expansion of the positioning element. In such a variation, the electrode(s) may, for example, be affixed to the inside surface, outside surface or at least partially embedded within the wall of the positioning element. In another embodiment, the electrode(s) do not contact the vessel wall, and may be positioned at any desired location within the vessel.

The electrode(s) 507 or any other portion of the apparatus 500, such as catheter 502 or element 504, additionally or alternatively may comprise one or more sensors, such as thermocouples 510, for monitoring the temperature or other parameters of the target tissue, the non-target tissue, the electrodes, the positioning element and/or any other portion of the apparatus 500 or of the patient's anatomy. The treatment regime may be controlled using the measured parameter(s) as feedback. This feedback may be used, for example, to maintain the parameter(s) below a desired threshold, for example, a threshold that may cause injury to the non-target tissues. Conversely, the feedback may be used to maintain the parameter(s) at or above a desired threshold, for example, a threshold that may induce a desired effect in the target tissues, such as neuromodulation of target neural fibers or denervation of tissues innervated by the target neural fibers. Furthermore, the feedback may be used to keep the parameter(s) within a range that will induce the desired effect in the target tissues without injuring the non-target tissues to an unacceptable extent. Multiple parameters (or the same or multiple parameters at multiple locations) optionally may be used as control feedback for ensuring the desired effects while mitigating the undesired effects.

Figure 3E:
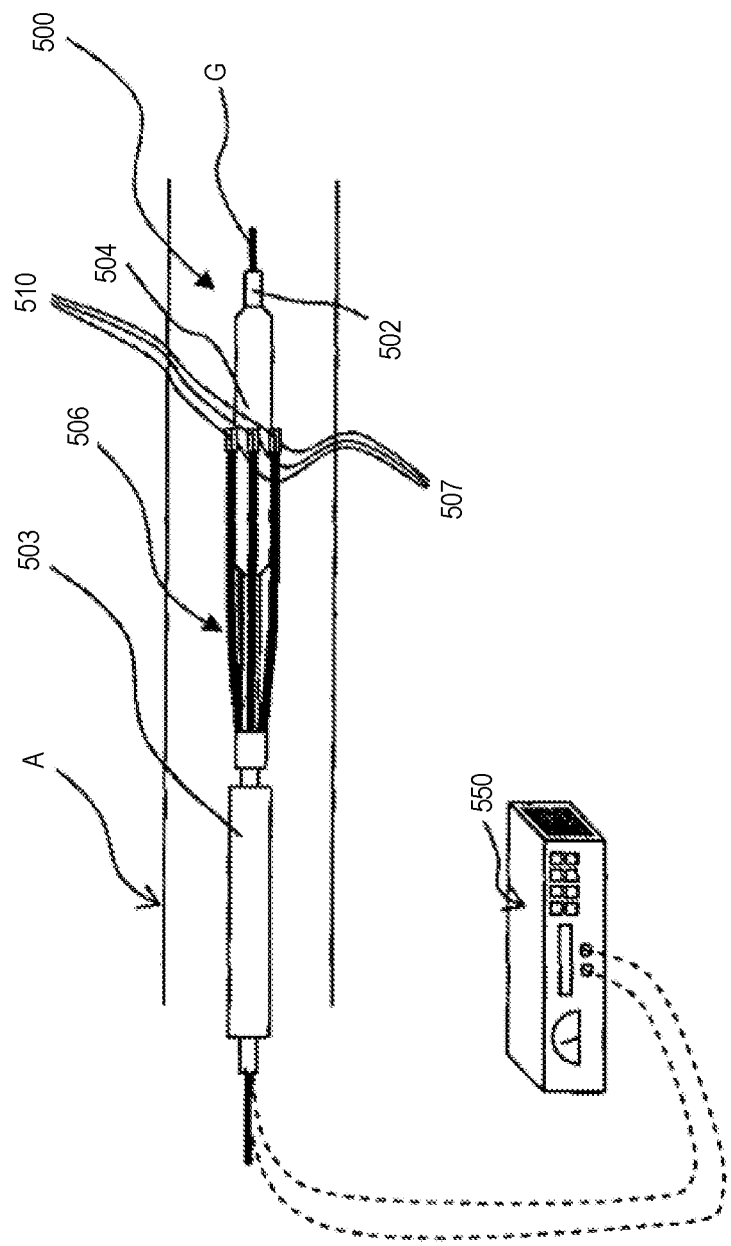
FIGS. 3E-3H are schematic side views, partially in section, and cross-sectional views illustrating an example of methods and apparatus for a non-continuous circumferential treatment of a body lumen.

As seen in FIG. 3E, the catheter 502 may be delivered to a treatment site within the artery A (or within a vein or any other vessel in proximity to target neural fibers) in a low profile delivery configuration, for example, through the guide catheter or sheath 503. Alternatively, catheters may be positioned in multiple vessels for neuromodulation, e.g., within both an artery and a vein. Multi-vessel techniques for electric field neuromodulation have been described previously, for example, in Applicant's U.S. patent application Ser. No. 11/451,728, filed Jul. 12, 2006, which is incorporated herein by reference in its entirety.

Figure 3F:
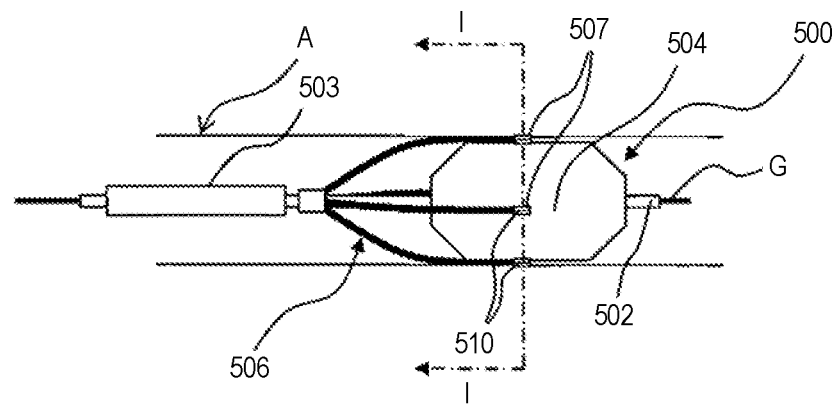

Once positioned within the vasculature as desired, the optional positioning element 504 may be expanded to deploy the electrode element 506 and bring the electrode(s) 507 into contact with an interior wall of the vessel, as seen in FIG. 3F. An electric field then may be generated by the field generator 550, transferred through the catheter 502 to the electrode element 506 and the electrodes 507, and delivered via the electrode(s) 507 across the wall of the artery. The electric field modulates the activity along neural fibers within the wall of the artery or in proximity to the artery, e.g., at least partially denervates tissue or organ(s) innervated by the neural fibers. This may be achieved, for example, via ablation or necrosis or via non-ablative injury or other changes to the target neural fibers or supporting structures. The electric field also may induce electroporation in the neural fibers.

Figure 3G:
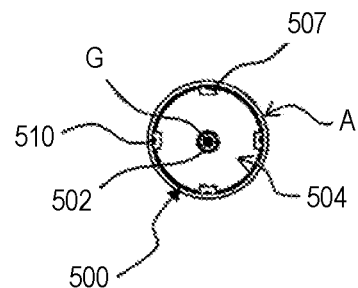
Figure 3H:
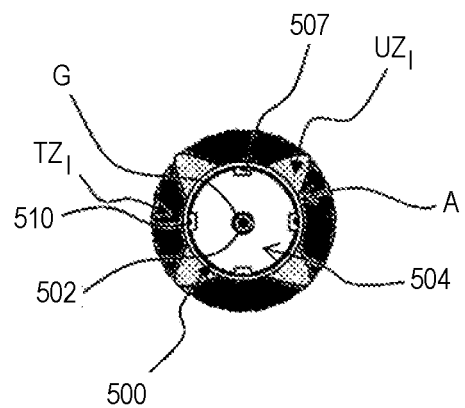

As seen in the cross-sectional view of FIG. 3G taken along the radial plane I-I of FIG. 3F, the apparatus 500 illustratively comprises four electrodes 507 equally spaced about the circumference of the electrode element 506 and the positioning element 504. As seen in FIG. 3H, when utilized in a monopolar fashion in combination with an external ground (not shown; per se known), the circumferential segments treated by each electrode overlap to form discrete treatment zones $TZ_I$ that are not continuous completely around the circumference of the artery in a radial plane normal to the vessel wall. As a result, there are discrete untreated zones $UZ_I$ about the circumference of the artery. Additional details regarding the apparatus 500 and other examples of suitable treatment devices are described in U.S. Pat. No. 8,347,891, which is incorporated herein by reference as noted previously.

FIGS. 3I and 3J illustrate yet another embodiment of an apparatus configured in accordance with the present technology. FIG. 3I, for example, illustrates an apparatus 650 comprising an expandable basket having a plurality of electrodes that may be expanded into contact with the vessel wall. The apparatus 650 comprises a catheter 652 having expandable distal basket 654 formed from a plurality of circumferential struts or members. A plurality of electrodes 656 are formed along the members of basket 654. Each member of the basket illustratively comprises a bipolar electrode pair configured to contact a wall of renal artery RA or another desired blood vessel.

Basket 654 may be fabricated, for example, from a plurality of shape-memory wires or ribbons, such as Nitinol, spring steel or elgiloy wires or ribbons, that form basket members 653. When the basket members comprise ribbons, the ribbons may be moved such that a surface area contacting the vessel wall is increased. Basket members 653 are coupled to catheter 652 at proximal and distal connections 655a and 655b, respectively. In such a configuration, the basket may be collapsed for delivery within sheath 650, and may self-expand into contact with the wall of the artery upon removal from the sheath. Proximal and/or distal connection 655a and 655b optionally may be configured to translate along the shaft of catheter 652 for a specified or unspecified distance in order to facilitate expansion and collapse of the basket.

Basket 654 alternatively may be formed from a slotted and/or laser-cut hypotube. In such a configuration, catheter 652 may, for example, comprise inner and outer shafts that are moveable relative to one another. Distal connection 655b of basket 654 may be coupled to the inner shaft and proximal connection 655a of the basket may be coupled to the outer shaft. Basket 654 may be expanded from a collapsed delivery configuration to the deployed configuration of FIG. 3I by approximating the inner and outer shafts of catheter 652, thereby approximating the proximal and distal connections 655a and 655b of the basket and expanding the basket. Likewise, the basket may be collapsed by separating the inner and outer shafts of the catheter.

As seen in FIG. 3J, individual electrodes may be arranged along a basket strut or member 653. In one embodiment, the strut is formed from a conductive material coated with a dielectric material, and the electrodes 656 may be formed by removing regions of the dielectric coating. The insulation optionally may be removed only along a radially outer surface of the member such that electrodes 656 remain insulated on their radially interior surfaces; it is expected that this will direct the current flow outward into the vessel wall.

In addition, or as an alternative, to the fabrication technique of FIG. 3J, the electrodes may be affixed to the inside surface, outside surface or embedded within the struts or members of basket 654. The electrodes placed along each strut or member may comprise individual electrodes, a common but segmented electrode, or a common and continuous electrode. Individual electrodes or groups of electrodes may be configured to provide a bipolar signal, or all or a subset of the electrodes may be actuated together in conjunction with an external patient ground for monopolar use. Further details regarding the apparatus 650 and other examples of suitable treatment devices are described in U.S. Pat. No. 7,653,438, which is incorporated herein by reference as noted previously.

V. METHODS FOR TREATMENT OF HYPERTENSION

Disclosed herein are several embodiments of methods directed to treatment of hypertension and other conditions (e.g., conditions related to hypertension) using catheter-based renal neuromodulation. The methods disclosed herein are expected to represent various advantages over a number of conventional approaches and techniques in that they may allow for potential targeting of the cause(s) of hypertension and/or improving one or more measurable physiological parameters corresponding to hypertension, thereby providing for localized treatment and limited duration treatment regimens (e.g., one-time treatment), thereby reducing patient long-term treatment compliance issues.

In certain embodiments, the methods provided herein comprise performing renal neuromodulation, thereby decreasing sympathetic renal nerve activity. In certain embodiments, renal neuromodulation may be repeated one or more times at various intervals until a desired sympathetic nerve activity level or another therapeutic benchmark is reached. In one embodiment, a decrease in sympathetic nerve activity may be observed via a marker of sympathetic nerve activity in patients having hypertension, such as decreased levels of plasma norepinephrine (noradrenaline). Other measures or markers of sympathetic nerve activity can include muscle sympathetic nerve activity (MSNA), NE spillover, and/or heart rate variability. In another embodiment, other measurable physiological parameters or markers, such as improved blood pressure control, changes in aldosterone-to-renin ratio, changes in a salt suppression test, changes in blood plasma levels of potassium, etc., can be used to assess efficacy of the renal neuromodulation treatment for patients having hypertension.

In certain embodiments of the methods provided herein, renal neuromodulation is expected to result in a change in blood pressure and/or sympathetic nerve activity over a specific timeframe. For example, in certain of these embodiments, blood pressure and/or sympathetic nerve activity levels are decreased over an extended timeframe, e.g., within 1 month, 2 months, 3 months, 6 months, 9 months or 12 months post-ablation.

In several embodiments, the methods disclosed herein may comprise an additional step of measuring blood pressure and/or sympathetic nerve activity levels, and in certain of these embodiments, the methods can further comprise comparing the activity level to a baseline activity level. Such comparisons can be used to monitor therapeutic efficacy and to determine when and if to repeat the neuromodulation procedure (e.g., immediately, after a predetermined period of time, repeated procedures at set periods of time, or in other cases for a specific patient population such as patients that have experienced a sufficient drop in blood pressure by 3 months, etc.). In certain embodiments, a baseline blood pressure and/or sympathetic nerve activity level is derived from the subject undergoing treatment. For example, baseline blood pressure and/or sympathetic nerve activity level may be measured in the subject at one or more timepoints prior to treatment. A baseline blood pressure and/or sympathetic nerve activity value may represent blood pressure and/or sympathetic nerve activity at a specific timepoint before renal neuromodulation, or it may represent an average activity level at two or more timepoints prior to renal neuromodulation. In certain embodiments, the baseline value is based on blood pressure and/or sympathetic nerve activity immediately prior to treatment (e.g., after the subject has already been catheterized). Alternatively, a baseline value may be derived from a standard value for blood pressure and/or sympathetic nerve activity observed across the population as a whole or across a particular subpopulation. In certain embodiments, post-neuromodulation sympathetic nerve activity levels are measured in extended timeframes post-neuromodulation, e.g., 3 months, 6 months, 12 months, etc. post-neuromodulation.

In certain embodiments of the methods provided herein, the methods are designed to decrease blood pressure and/or sympathetic nerve activity to a target level. In these embodiments, the methods include a step of measuring blood pressure and/or sympathetic nerve activity levels post-neuromodulation (e.g., 3 months post-treatment, 6 months post-treatment, 12 months post-treatment, etc.) and comparing the resultant activity level to a baseline activity level as discussed above. In certain of these embodiments, the treatment is repeated until the target sympathetic nerve activity level is reached. In other embodiments, the methods are simply designed to decrease blood pressure and/or sympathetic nerve activity below a baseline level without requiring a particular target activity level.

Renal neuromodulation may be performed on a patient diagnosed with hypertension to reduce one or more measurable physiological parameters corresponding to the hypertension. In some embodiments, renal neuromodulation may decrease blood pressure, decrease aldosterone-to-renin ratio, change the result of a salt suppression test (e.g., negative result), increase blood plasma levels of potassium, etc. For example, renal neuromodulation may reduce the severity and/or frequency of hypertension in a patient. A reduction in blood pressure can be, for example, by at least about 5%, 10%, or a greater amount as determined by average blood pressure analysis before and after (e.g., 1, 3, 6, or 12 months after) a renal neuromodulation procedure. Corresponding results may be obtained with plasma aldosterone concentration, plasma renin activity, aldosterone-to-renin ratio, and/or blood plasma levels of potassium (e.g., to assess reversal of a hypokalemia state). A reduction in plasma aldosterone concentration can be, for example, by at least about 5%, 10% or a greater amount as determined by blood analysis. In a specific example, plasma aldosterone concentration can be reduced by an amount up to about 90% as determined by blood analysis. In another instance, a reduction in an aldosterone-to-renin ratio can be, for example, by at least about 5%, 10% or a greater amount (e.g., about 50%, about 80%, about 90%) as determined by blood analysis and calculation. In the case of secondary hypertension, renal neuromodulation may provide a reduction in plasma renin activity, for example, by about 5%, 10% or a greater amount as determined by blood analysis. In a specific example, plasma renin activity can, for example, be reduced by an amount up to about 80% as determined by blood analysis. Additionally, an increase in blood plasma levels of potassium can be, for example, by about 5%, 10% or a greater amount as determined by blood analysis. For example, normal plasma potassium levels are approximately between 3.5 to about 5.0 mEq/L. Accordingly, hypokalemia can be characterized by a plasma potassium level less than about 3.5 mEq/L.

In addition to or instead of affecting the blood pressure or hypokalemia in a patient, renal neuromodulation may efficaciously treat other measurable physiological parameter(s) or sequelae corresponding to hypertension. For example, in some embodiments, renal neuromodulation may reduce the severity and/or frequency of headaches, muscle cramps/spasms, muscle fatigue, numbness, tingling, metabolic alkalosis, polyuria, polydipsia, and/or patient reported fatigue. Furthermore, renal neuromodulation may improve markers of renal injury (e.g., serum BUN levels, serum creatinine levels, serum cystatin C levels, proteinuria levels, NGAL levels, and Kim-1 levels) or may improve renal function (e.g., slow a decline in glomerular filtration rate) in a patient, prevent end-stage renal disease, etc. These and other results may occur at various times, e.g., directly following renal neuromodulation or within about 1 month, 3 months, 6 months, a year, or a longer period following renal neuromodulation.

As previously discussed, the progression of hypertension may be related to sympathetic overactivity and, correspondingly, the degree of sympathoexcitation in a patient may be related to the severity of the clinical presentation of the hypertension. The kidneys are strategically positioned to be both a cause (via afferent nerve fibers) and a target (via efferent sympathetic nerves) of elevated central sympathetic drive. In some embodiments, renal neuromodulation is used to reduce central sympathetic drive in a patient diagnosed with hypertension in a manner that treats the patient for the hypertension and/or sequelae associated with hypertension. In some embodiments, for example, MSNA can be reduced by at least about 10% in the patient within about three months after at least partially inhibiting sympathetic neural activity in nerves proximate a renal artery of the kidney. Similarly, in some instances whole body NE spillover can be reduced at least about 20% in the patient within about three months after at least partially inhibiting sympathetic neural activity in nerves proximate a renal artery of the kidney. Additionally, measured NE content (e.g., assessed via renal biopsy, assessed in real-time via intravascular blood collection techniques, etc.) can be reduced (e.g., at least about 5%, 10%, or by at least 20%) in the patient within about three months after at least partially inhibiting sympathetic neural activity in nerves proximate a renal artery innervating the kidney.

In one prophetic example, a patient diagnosed with hypertension can be subjected to a baseline assessment indicating a first set of measurable parameters corresponding to the hypertension. Such parameters can include, for example, blood pressure, sodium level, potassium level, plasma aldosterone concentration, plasma renin activity, aldosterone-to-renin ratio, salt suppression, levels of components of the RAAS (e.g., angiotensinogen II levels), urinary $Na^+/K^+$ levels, levels of central sympathetic drive (e.g., MSNA, whole body NE spillover), and markers of renal damage or measures of renal function (e.g. creatinine level, estimated glomerular filtration rate, blood urea nitrogen level, creatinine clearance, cystatin-C level, NGAL levels, KIM-1 levels, presence of proteinuria or microalbuminuria, urinary albumin creatinine ratio). Following baseline assessment, the patient can be subjected to a renal neuromodulation procedure. Such a procedure can, for example, include any of the treatment modalities described herein or another treatment modality in accordance with the present technology. The treatment can be performed on nerves proximate one or both kidneys of the patient. Following the treatment (e.g., 1, 3, 6, or 12 months following the treatment), the patient can be subjected to a follow-up assessment. The follow-up assessment can indicate a measurable improvement in one or more physiological parameters corresponding to the hypertension.

The methods described herein address the sympathetic excess that is thought to be an underlying cause of hypertension or a central mechanism through which hypertension manifests its multiple deleterious effects on patients. In contrast, known therapies currently prescribed for patients having hypertension typically address only specific manifestations of hypertension. Additionally, these known therapies can have significant limitations including limited efficacy, undesirable side effects and can be subject to adverse or undesirable drug interactions when used in combination. Moreover, conventional therapies may require the patient to remain compliant with the treatment regimen over time. In contrast, renal neuromodulation can be a one-time or otherwise limited treatment that would be expected to have durable benefits to inhibit the long-term disease progression and thereby achieve a favorable patient outcome.

In some embodiments, patients diagnosed with hypertension can be treated with renal neuromodulation alone. However, in other embodiments, patients diagnosed with hypertension can be treated with one or more combinations of therapies for treating primary causative modes of hypertension and/or sequelae of hypertension. For example, combinations of therapies can be tailored based on specific manifestations of the disease in a particular patient. In a specific example, patients having hypertension and presenting hypertension can be treated with both antihypertensive drugs and renal neuromodulation and/or other forms of tissue modulation (e.g., carotid body modulation, etc.). In another example, renal neuromodulation can be combined with angiotensin-converting-enzyme (ACE) inhibitors (e.g., Captopril, Zofenopril, Enalapril, Ramipril, Fosinopril, etc.) or angiotensin receptor blockers (ARBs) (e.g., Valsartan, Telmisartan, Losartan, etc.) to treat secondary hypertension. Primary hypertension can be treated using a combination of renal neuromodulation and surgical removal of a focal aldosterone producing adenoma (e.g., adrenalectomy) or drugs that block the secretion of aldosterone (e.g., spironolactone, eplerenone). In patients also experiencing hypokalemia, intravenous (IV) supplementation, oral potassium chloride supplements, and/or dietary modifications can accompany renal neuromodulation.

In further embodiments, patients taking maximum tolerated doses of one or more antihypertension drugs with a combination/cocktail of selected drugs may also be treated with renal neuromodulation. In some embodiments, this combined therapy may result in the patient being able to reduce the number of drugs being taken in the combination/cocktail, lower the dosage of one or more of the drugs, and/or eliminate one or more of the drugs. In still another embodiment, the combined therapy may result in other modifications to the patient's drug regimen (e.g., adjustments/exchanges/alterations of the combination/cocktail of selected drugs, change classes of antihypertension drugs, etc.) to help further improve/enhance treatment of the patient's hypertension and related conditions.

Treatment of hypertension or related conditions may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

A. ADDITIONAL EXAMPLES

Example 1: Effect of Renal Denervation in a Blinded Study of Patients with Uncontrolled Hypertension FIGS. 4A-20 are display diagrams illustrating baseline data and corresponding results from one particular study to determine the effects of renal denervation (RDN) on 535 human patients with uncontrolled hypertension (Kandzari, D. E., et. al., 2012, Clinical Cardiology 35: 528-35; incorporated herein by reference in its entirety).

Inclusion and Exclusion Criteria

Figure 4A:
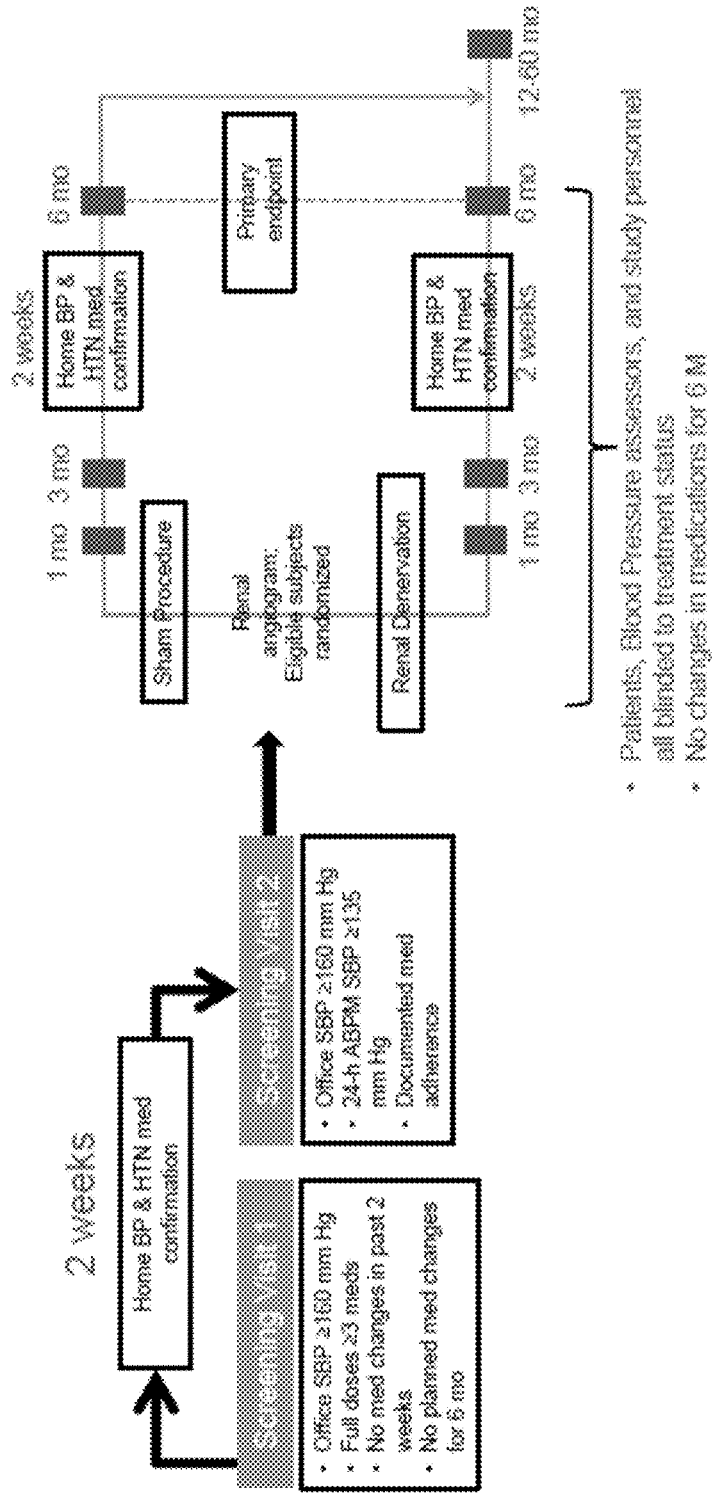
FIGS. 4A-20 are display diagrams illustrating baseline data and corresponding results from one particular study to determine the effects of renal denervation on 535 human patients with uncontrolled hypertension.

A prospective, single-blind, randomized, sham-controlled trial was conducted. Patients 18 to 80 years of age with medically diagnosed resistant hypertension were randomly assigned in a 2:1 ratio to undergo RDN or a sham procedure (FIG. 4A). Patients with severe resistant hypertension were prospectively enrolled in the study. On initial screening and before randomization, patients were required to have a systolic blood pressure of 160 mm Hg or higher (average of three measurements at an office visit [hereafter referred to as office blood pressure] while the patient was seated) and to be taking maximally tolerated doses of three or more antihypertensive medications of complementary classes, one of which had to be a diuretic at an appropriate dose. No changes in antihypertension medication in the previous 2 weeks were allowed. For the next 2 weeks, patients recorded their blood pressure at home (hereafter referred to as home blood pressure) in the morning and in the evening and kept a diary indicating their adherence to medical therapy. Then a confirmatory screening visit occurred, during which the systolic blood pressure of 160 mm Hg or higher was confirmed, adherence to medications was documented, and automated 24-hour ambulatory blood-pressure monitoring was performed to ensure a systolic blood pressure of 135 mm Hg or higher. Patients were also excluded if they had an estimated glomerular filtration rate (eGFR) of less than 45 ml per minute per 1.73 m² of body-surface area. Clinical exclusion criteria were known secondary causes of hypertension and more than one hospitalization for a hypertensive emergency in the previous year. Anatomical exclusion criteria were renal-artery stenosis of more than 50%, renal-artery aneurysm, prior renal-artery intervention, multiple renal arteries, a renal artery of less than 4 mm in diameter, or a treatable segment of less than 20 mm in length. The primary efficacy end point was the change in office systolic blood pressure at 6 months; a secondary efficacy end point was the change in mean 24-hour ambulatory systolic blood pressure. The primary safety end point was a composite of death, end-stage renal disease, embolic events resulting in end-organ damage, renovascular complications, or hypertensive crisis at 1 month or new renal-artery stenosis of more than 70% at 6 months. The Major Adverse Event (MAE) rate was required to be <0.7 to meet the primary safety end point.

Patients underwent renal angiography before randomization into treatment or control groups. At 6 months, patients in the control group were allowed to cross-over to undergo denervation if they still met the inclusion criteria for the study.

Figure 4B:
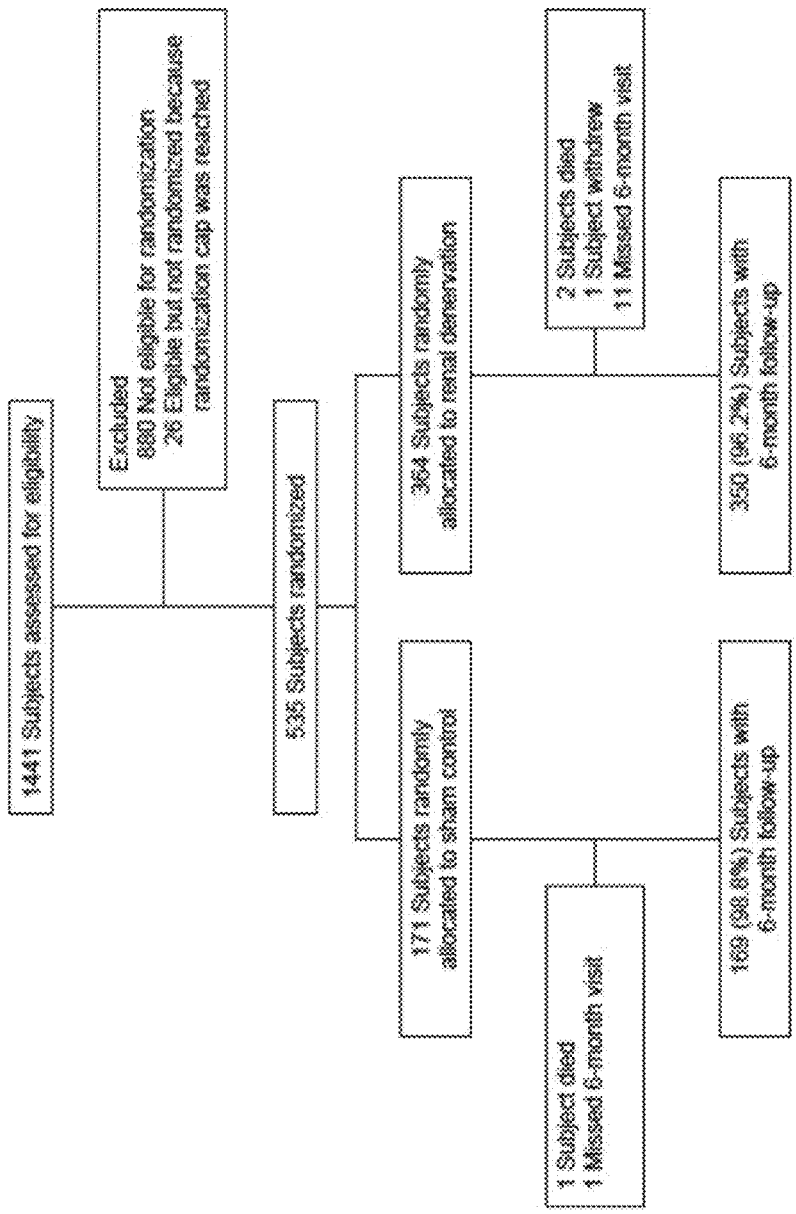
Figure 4C:
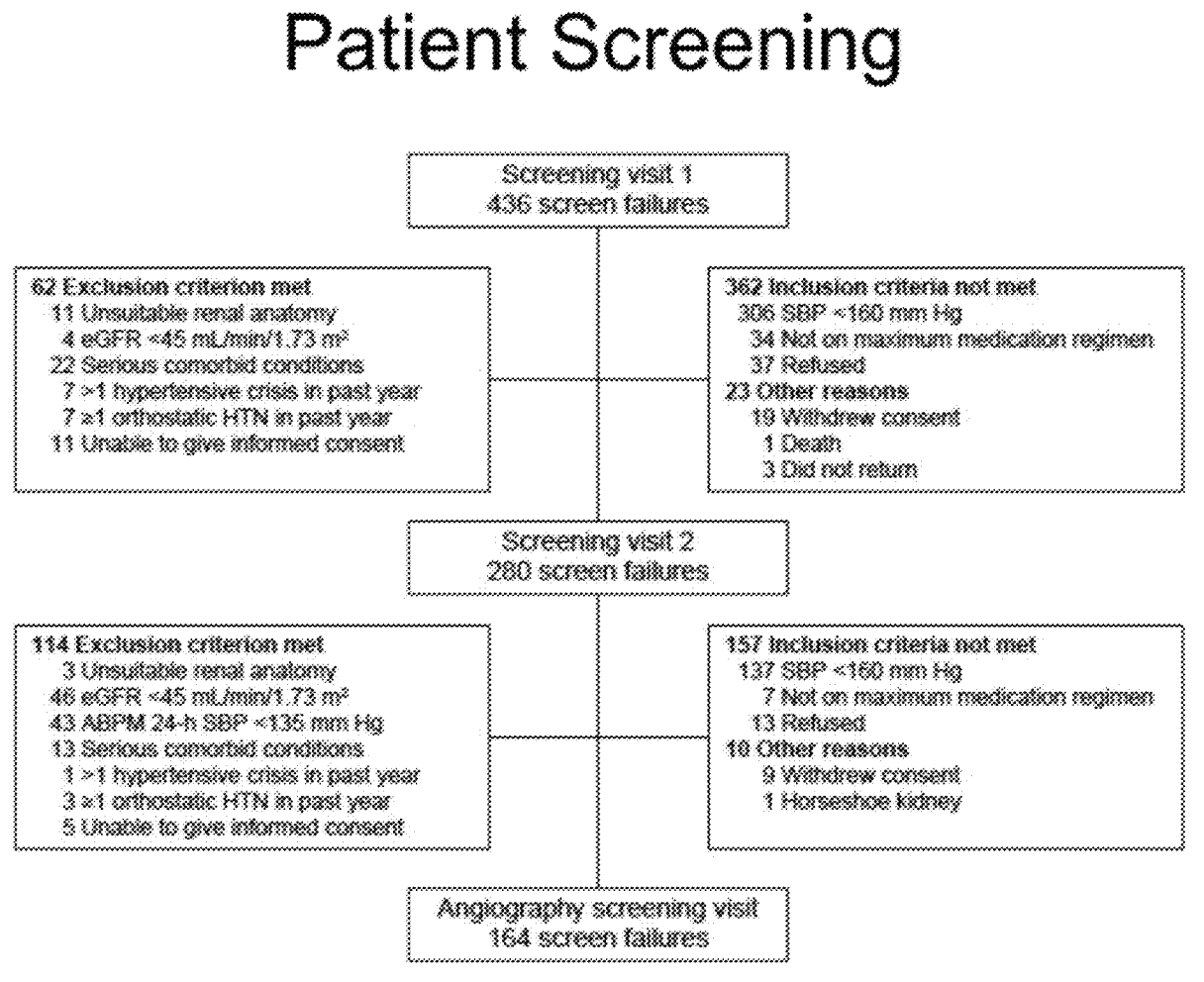

A total of 1441 patients were assessed for eligibility; of these patients, 535 (37.1%) from 88 sites in the United States were enrolled in the trial between October 2011 and May 2013. Of the 535 patients, nearly 70 percent had been treated for an average of ten years for uncontrolled hypertension according to standard of care. FIG. 4B is a flow diagram illustrating the selection process for patients randomized to receive RDN or sham control. FIG. 4C is flow diagram illustrating the patient criteria and reasons for non-study inclusion. Table 1 below shows the baseline characteristics of the patients selected for study inclusion.

TABLE 1

Baseline characteristics of the study population

| Characteristic | Renal-Denervation Group (N = 364) | Sham-Procedure Group (N = 171) |
|---|---|---|
| Age - yr | 57.9 ± 10.4 | 56.2 ± 11.2 |
| Male sex - no. (%) | 215 (59.1) | 110 (64.3) |
| Body-mass index† | 34.2 ± 6.5 | 33.9 ± 6.4 |
| Race - no./total no. (%)‡ | | |
| Black | 90/363 (24.8) | 50/171 (29.2) |
| White | 265/363 (73.0) | 119/171 (69.6) |
| Asian | 2/363 (0.6) | 0/171 |
| Other | 6/363 (1.7) | 2/171 (1.2) |
| Medical history - no. (%) | | |
| Renal insufficiency§ | 34 (9.3) | 17 (9.9) |
| Renal-artery stenosis | 5 (1.4) | 4 (2.3) |

TABLE 1-continued

Baseline characteristics of the study population

| Characteristic | Renal-Denervation Group (N = 364) | Sham-Procedure Group (N = 171) |
|---|---|---|
| Obstructive sleep apnea | 94 (25.8) | 54 (31.6) |
| Stroke | 29 (8.0) | 19 (11.1) |
| Transient ischemic attack | 28 (7.7) | 13 (7.6) |
| Peripheral artery disease | 19 (5.2) | 5 (2.9) |
| Cardiac disease | | |
| Coronary artery disease | 101 (27.7) | 43 (25.1) |
| Myocardial infarction | 32 (8.8) | 11 (6.4) |
| Diabetes | | |
| Type 1 | 0 | 0 |
| Type 2 | 171 (47.0) | 70 (40.9) |
| Hyperlipidemia - no. (%) | 252 (69.2) | 111 (64.9) |
| Current smoker - no. (%) | 36 (9.9) | 21 (12.3) |
| Family history of hypertension - no/total no. (%) | 305/361 (84.5) | 140/170 (82.4) |
| Hypertension history - no. (%) | | |
| Hospitalization for hypertensive crisis | 83 (22.8) | 38 (22.2) |
| Hospitalization for hypotension | 8 (2.2) | 4 (2.3) |
| No. Of antihypertensive medications | 5.1 ± 1.4 | 5.2 ± 1.4 |
| Type of antihypertensive medication - no. (%) | | |
| ACE inhibitor | | |
| Patients taking medication | 179 (49.2) | 71 (41.5) |
| Patients taking maximally tolerated dose | 167 (45.9) | 64 (37.4) |
| Angiotensin-receptor blocker | | |
| Patients taking medication | 182 (50.0) | 91 (53.2) |
| Patients taking maximally tolerated dose | 180 (49.5) | 88 (51.5) |
| Aldosterone antagonist | 82 (22.5) | 49 (28.7) |
| Alpha-adrenergic blocker | 40 (11.0) | 23 (13.5) |
| Beta-blocker | 310 (85.2) | 147 (86.0) |
| Calcium-channel blocker | | |
| Patients taking medication | 254 (69.8) | 125 (73.1) |
| Patients taking maximally tolerated dose | 208 (57.1) | 109 (63.7) |
| Centrally acting sympatholytic agent | 179 (49.2) | 75 (43.9) |
| Direct-acting renin inhibitor | 26 (7.1) | 12 (7.0) |
| Direct-acting vasodilator | 134 (36.8) | 77 (45.0) |
| Diuretic | | |
| Patients taking medication | 363 (99.7) | 171 (100) |
| Patients taking maximally tolerated dose | 351 (96.4) | 167 (97.7) |

*Plus-minus values are means ±SD. All differences in characteristics between groups were nonsignificant. ACE denotes angiotensin-converting enzyme.
†The body-mass index is the weight in kilograms divided by the square of the height in meters.
‡Race was determined by self-report.
§Renal insufficiency was defined as an estimated glomerular filtration rate of less than 60 ml per minute per 1.73 m² of body-surface area.

There were no significant differences between the patients assigned to the RDN treatment group and the patients assigned to the sham procedure control group. Table 2 shows the procedural characteristics for the RDN treatment group and the sham procedure control group.

TABLE 2

Procedural Characteristics

| Characteristic | Renal Denervation Group (N = 364) | Sham-Procedure Group (N = 171) |
|---|---|---|
| Procedure time (min.) | 92.5 ± 38.4 | 56.0 ± 27.5 |
| Denervation time (min.) | 46.4 ± 15.2 | n/a |
| Non-ionic contrast used (%) | 328 (90.1) | 155 (90.6) |

TABLE 2-continued

Procedural Characteristics

| Characteristic | Renal Denervation Group (N = 364) | Sham-Procedure Group (N = 171) |
|---|---|---|
| Volume of contrast used (cc) | 177.0 ± 76.6 | 78.6 ± 51.9 |
| Total # ablation attempts | 11.2 ± 2.8 | n/a |
| # 120 second ablations | 9.2 ± 2.0 | n/a |
| % 120 second ablations | 83.8 ± 15.6 | n/a |
| Intra-procedural medications | | |
| Pain medications (%) | 348 (97.2) | 162 (94.7) |
| Sedatives/Anxiolytics (%) | 355 (99.2) | 169 (98.8) |
| Atropine (%) | 10 (2.8) | 1 (0.6) |
| Hospitalization (days) | 1.0 ± 0.3 | 1.0 ± 0.4 |
| Device success* | 363 (99.7) | n/a |
| Procedure Success† | 363 (99.7) | n/a |

Values are expressed as n (%) or mean ± SD
*Defined as successful delivery of any radiofrequency energy
†Defined as successful delivery of any radiofrequency energy in the absence of an in-hospital major adverse event Patients were receiving an average of five antihypertensive medications, and on average, four of these medications were at maximally tolerated doses. Table 3 shows the medications used by patients in the RDN treatment and sham procedure control groups.

The numbers and types of antihypertensive medications at 6 months were similar to those at baseline in both groups. Table 4 shows the diuretic use for each group at baseline. As shown, a majority of patients were receiving hydrochlorothiazide.

TABLE 4

Diuretic Use for Each Group at Baseline

| Diuretic | Maximum tolerated dose* | Renal Denervation Group (N = 364) | Sham-Procedure Group (N = 171) |
|---|---|---|---|
| Chlorthalidone | 25 mg | 45 | 26 |
| Hydrochlorothiazide | 25 mg | 219 | 100 |
| Indapamide | 2.5 mg | 1 | 3 |
| Metolazone | 5 mg | 5 | 1 |
| Amiloride | 10 mg | 4 | 3 |
| Triamterene | 100 mg | 11 | 10 |
| Spironolactone** | 50 mg | 16 | 6 |
| Furosemide | 80 mg | 87 | 43 |
| Ethacrynic acid | 200 mg | 2 | 0 |

TABLE 3

Medication Use

| | Renal Denervation Group (N = 364) | Sham-Procedure Group (N = 171) | Renal Denervation Group (N = 364) | Sham-Procedure Group (N = 171) |
|---|---|---|---|---|
| Number of antihypertensive medications | 5.1 ± 1.4 | 5.2 ± 1.4 | 5.0 ± 1.4 | 5.2 ± 1.6 |
| Number of maximum tolerated antihypertensive medications | 4.0 ± 1.1 | 4.0 ± 1.0 | n/a | n/a |
| ACE inhibitor† | 179 (49.2) | 71 (41.5) | 167 (46.3) | 71 (41.8) |
| % taking maximally tolerated dose | 167 (45.9) | 64 (37.4) | | |
| Angiotensin receptor blocker | 182 (50.0) | 91 (53.2) | 179 (49.6) | 89 (52.4) |
| % taking maximally tolerated dose | 180 (49.5) | 88 (51.5) | | |
| Aldosterone antagonists | 82 (22.5) | 49 (28.7) | 87 (24.1) | 50 (29.4) |
| Alpha-adrenergic blocker | 40 (11.0) | 23 (13.5) | 38 (10.5) | 21 (12.4) |
| Beta blockers | 310 (85.2) | 147 (86.0) | 302 (83.7) | 148 (87.1) |
| Calcium channel blocker | 254 (69.8) | 125 (73.1) | 250 (69.3) | 129 (75.9) |
| % taking maximally tolerated dose | 208 (57.1) | 109 (63.7) | | |
| Centrally-acting sympatholytics | 179 (49.2) | 75 (43.9) | 176 (48.8) | 73 (42.9) |
| Diuretics | 363 (99.7) | 171 (100) | 347 (96.1) | 163 (95.9) |
| % taking maximally tolerated dose | 351 (96.4) | 167 (97.7) | | |
| Direct-acting renin inhibitors | 26 (7.1) | 12 (7.0) | 21 (5.8) | 13 (7.6) |
| Direct-acting vasodilators | 134 (36.8) | 77 (45.0) | 129 (35.7) | 71 (41.8) |

*There were 31 (5.8%) patients with a medication change between screening visit 1 and screening visit 2 but no significant difference in office systolic blood pressure was observed between the screening visit measurements.
†ACE denotes angiotensin-converting enzyme TABLE 4-continued Diuretic Use for Each Group at Baseline

| Diuretic | Maximum tolerated dose* | Renal Denervation Group (N = 364) | Sham-Procedure Group (N = 171) |
|---|---|---|---|
| Bumetanide | 2 mg | 7 | 4 |
| Torsemide | 10 mg | 10 | 7 |

*Based on JNC-7; 17 patients were on less than the maximum tolerated dose because of side effects;
**Spironolactone was the only diuretic being used by these 22 patients. Spironolactone was classified as a diuretic if there was no other diuretic in use and the Spironolactone daily dose was ≥50 mg. In all other situations spironolactone was classified as an aldosterone antagonist.

Table 5 shows the blinding index was significantly greater than 0.5 at discharge and at the 6-month follow-up visit, indicating proper blinding.

TABLE 5

Blinding Index

| Time | Blinding index | 95% CI |
|---|---|---|
| Discharge | 0.68 | (0.64, 0.72) |
| 6 Months | 0.77 | (0.74, 0.81) |

*The lower boundaries of the confidence intervals of the blinding index are both greater than 0.5, indicating that there is sufficient evidence for blinding.

Treatment

Patients in the treatment group underwent renal artery denervation using the Symplicity™ renal denervation system and the techniques described below. The Symplicity™ renal denervation system includes the Symplicity™ catheter and the Symplicity™ RF generator (Medtronic, Inc.). Patients were prepared using standard techniques for electrosurgery, with the patient's body insulated from contact with grounded metal. A disposable dispersive electrode was placed on the thigh or other non-bony area out of the angiogram field. Following system setup per manufacturer protocol, a 6 Fr (or larger) introducer sheath was introduced into the patient's femoral artery using standard interventional technique. A guide catheter was advanced into the targeted renal artery using fluoroscopic guidance. The catheter was advanced through the guide catheter to a distal treatment location in the main renal artery (≥5 mm proximal to the bifurcation) under fluoroscopic guidance.

After positioning the electrode in contact with the renal artery wall, the clinician engaged the Symplicity™ RF generator to deliver power to target tissue via the electrode using an automated algorithm that ceases power delivery when treatment is complete. The generator uses an algorithm to monitor temperature and impedance and control power output to assure delivery of energy to each site. Constant monitoring of temperature and impedance, for example, may allow the clinician to confirm stable wall contact, impedance drop (indicating delivery of energy), and safe, optimal temperature during the ablation period (approximate 2 minutes). Once treatment is complete, the catheter was repositioned to locate a next treatment site (e.g., approximately 5 mm proximal to the previous treatment site). While moving the electrode proximally within the renal artery, the catheter was torqued (e.g., rotated in 45 degree increments) to bring the electrode into apposition with the arterial wall at various circumferential positions defining a helical pattern about a longitudinal axis of the renal artery. In some patients, the helical pattern included at least one treatment location in each of an inferior, anterior, superior and posterior position around the wall (e.g., a four quadrant ablation pattern; FIG. 3B) in either a right or left renal artery or in both renal arteries. In other patients, neither the right nor left renal artery had a four quadrant ablation pattern. Tissue ablation treatments were continued until the desired number of treatments were completed in the renal artery (e.g., 4-6 ablation treatments per renal artery, greater than 6 ablation treatments per renal artery, or a maximum number of ablation treatments based on a length of the renal artery). The proceeding steps were then repeated for the patient's second renal artery, after which the catheter, guide catheter, and introducer sheath were removed from the patient.

Patients were unaware of whether they underwent renal-artery denervation or renal angiography only (sham control) as described further below. Blood-pressure assessors were also unaware of the study-group assignments. A blinding index, based on responses to a questionnaire, was calculated at hospital discharge and at 6 months to verify the effectiveness of blinding. The blinding index ranges from 0 (all patients correctly guessed their study-group assignments) to 1 (all patients did not know their study-group assignments), with values greater than 0.5 indicating successful blinding. According to protocol, changes in antihypertensive medication were not allowed during the 6-month follow-up period unless they were considered to be clinically necessary.

Sham Control

All patients underwent renal angiography according to standard procedures. Blinding was done by a combination of conscious sedation, sensory isolation (e.g., blindfold and music), and lack of familiarity with procedural details and expected duration. Patients were randomized after confirmation of suitable anatomy defined as bilateral single main renal arteries ≥4 mm in diameter and >20 mm in length, without significant stenosis or other abnormality. Following randomization patients in the sham-procedure group remained on the catheterization laboratory table for at least 20 minutes prior to removal of the introducer sheath. Family members were also blinded to the treatment. All patients were hospitalized overnight and standard of care post-intervention procedures were followed. Blood pressure assessments at each follow up visit were done by blinded, trained personnel.

At 6 months post-randomization (prior to unblinding), renal artery duplex ultrasound imaging was performed and assessed by the Vascular Ultrasound Core Laboratory (Boston, Mass.). If a clinically significant stenosis (e.g., renal artery to aorta peak systolic velocity ratio >3.5, or peak systolic velocity >200 cm/s with evidence of post-stenotic turbulence) was indicated, angiography was performed. The Angiography Core Laboratory (Boston, Mass.) compared the 6-month angiography with the baseline angiography to evaluate any potential new renal artery stenosis.

Results at 6 Months (Blinded Study)

The primary efficacy endpoint was the mean change in office systolic blood pressure from baseline to 6 months in the RDN treatment group, as compared with the mean change in the sham procedure control group, with a superiority margin of 5 mm Hg. Assuming a standard deviation of 25 mm Hg for both groups, at least a 10 mm Hg difference in 6 month blood pressure change would be required to successfully meet the efficacy endpoint. Symplicity HTN-1 and SYMPLICITY HTN-2 showed blood pressure reductions of 22.0±21.9 mm Hg and 31.7±23.1 mm Hg, respectively (Krum, H., et. al., 2009, Lancet 373:1275-81 and Esler M D, et. al., 2010 Lancet 376:1903-9, both of which are incorporated herein by reference in their entireties).

The study was also assessed for a secondary efficacy endpoint: the change in mean 24-hour ambulatory systolic blood pressure at 6 months. The primary safety end point was a composite of major adverse events, defined as death from any cause, end-stage renal disease, an embolic event resulting in end-organ damage, renal-artery or other vascular complications, or hypertensive crisis within 30 days or new renal-artery stenosis of more than 70% within 6 months. The objective performance criterion for the primary safety end point was a rate of major adverse events of 9.8%, which was derived from a meta-analysis of trials involving other renal interventions, with an estimated adjustment for hypertensive crises. Assuming a true major adverse event (MAE) rate for the RDN group of 6%, and using a one-sided 0.05 level of significance, a sample size of 316 RDN patients was required to yield 80% power to show that the MAE rate would be significantly lower than the performance goal. If no more than 22 of the 316 (7%) RDN patients experienced a MAE, the MAE rate would be statistically significantly less than the performance goal. Patients' systolic blood pressure can be followed semiannually through 5 years after randomization.

All office blood pressure measurements were taken with the Omron™ automatic blood pressure monitor and printer (Omron Healthcare, Inc., Bannockburn, Ill.). At the first screening visit, the appropriate arm for study measures was selected and then used for all subsequent follow-up visits. For each study visit, attempts were made to measure the patient's blood pressure within the same approximate timeframe of the day (i.e., morning, afternoon, or evening). Patients were requested to take all antihypertensive medications at least 1 hour prior to the blood pressure measurements, and were instructed not to drink coffee, or alcohol, smoke or exercise within 30 minutes before measurements. At least three seated blood pressure measurements taken at least 1 minute apart were obtained. If the lowest and highest systolic BP (SBP) values of 3 consecutive measurements were more than 15 mm Hg apart, additional readings were taken to try to get 3 consecutive readings within 15 mm Hg. If a less than a 15 mm Hg difference could not be obtained after at least 6 documented measurements, a 20 mm Hg difference was accepted. However, if the lowest and highest SBP values for the readings were more than 20 mm Hg apart after 6 measurements at screening visit 1 and screening visit 2, the patient was excluded from the study. All blood pressure assessors were licensed healthcare providers trained per American Heart Association methodology and certified prior to the start of the trial.

All 24-hour ambulatory blood pressure monitoring (ABPM) measurements were taken with a Spacelabs 24-hour ABPM device (Spacelabs Medical, Issaquah, Wash.), for consistency. The cuff was placed on the same arm as used for the office BP measurements. The ABPM parameters were set for every 30 minutes throughout the day (7 am to 9:59 pm) and for every 30 minutes at night (10 pm to 6:59 am). Patients were asked to keep a diary of key activities (going to bed and getting up, taking medications, other significant events). A 24-hour ABPM was considered adequate if the number of successful daytime readings captured was ≥21 and the number of successful nighttime readings captured was ≥12.

Figure 5A:
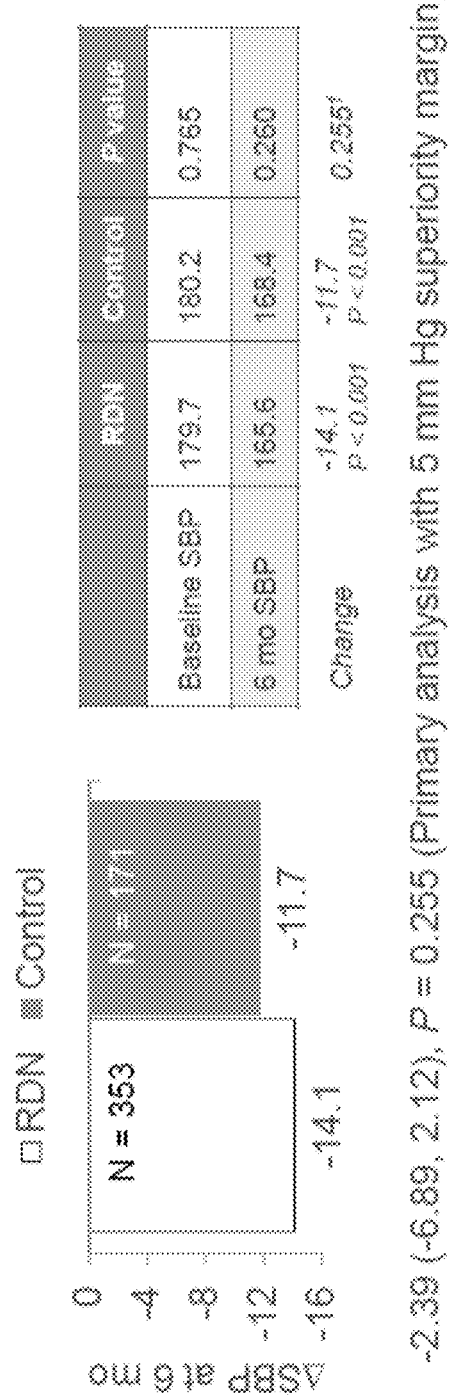
Figure 5B:
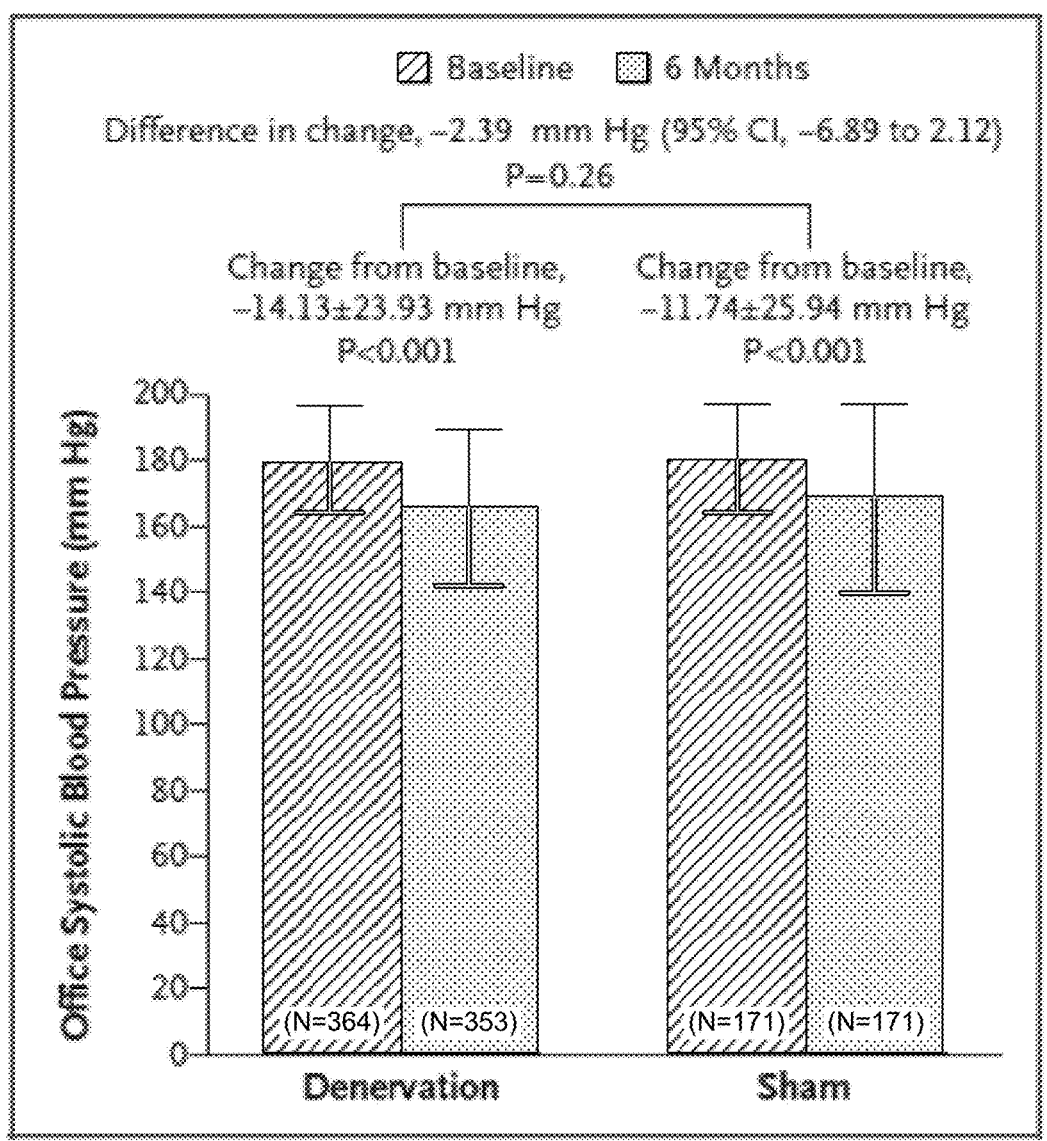
Figure 6A:
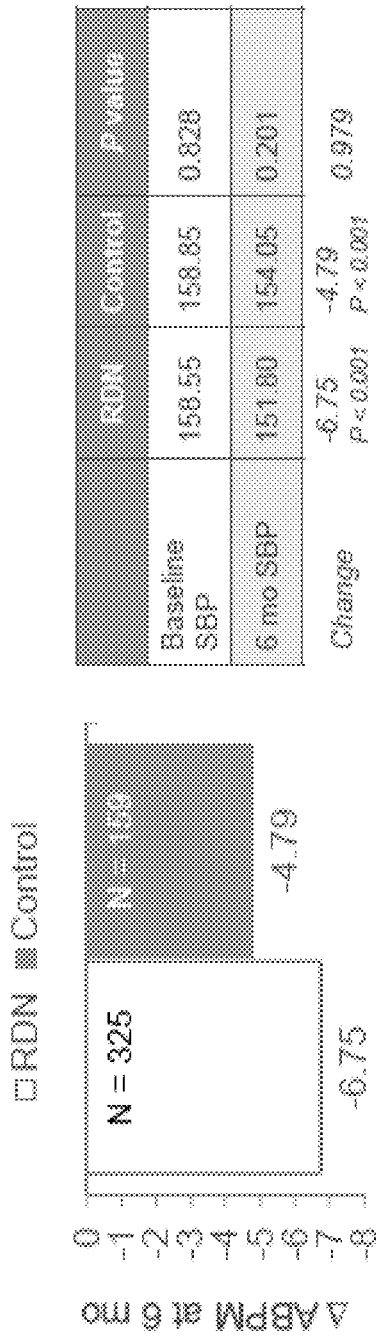
Figure 6B:
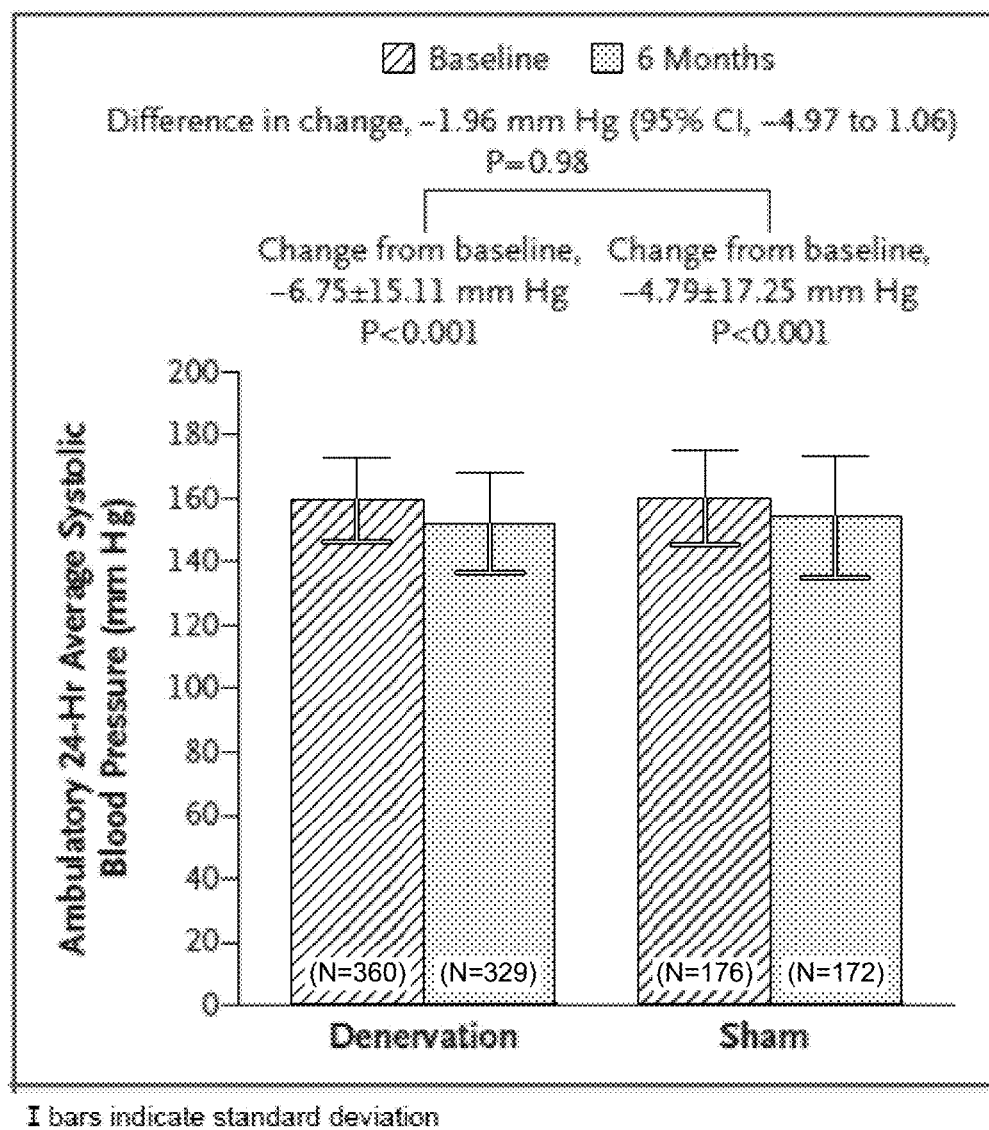
Figure 7:
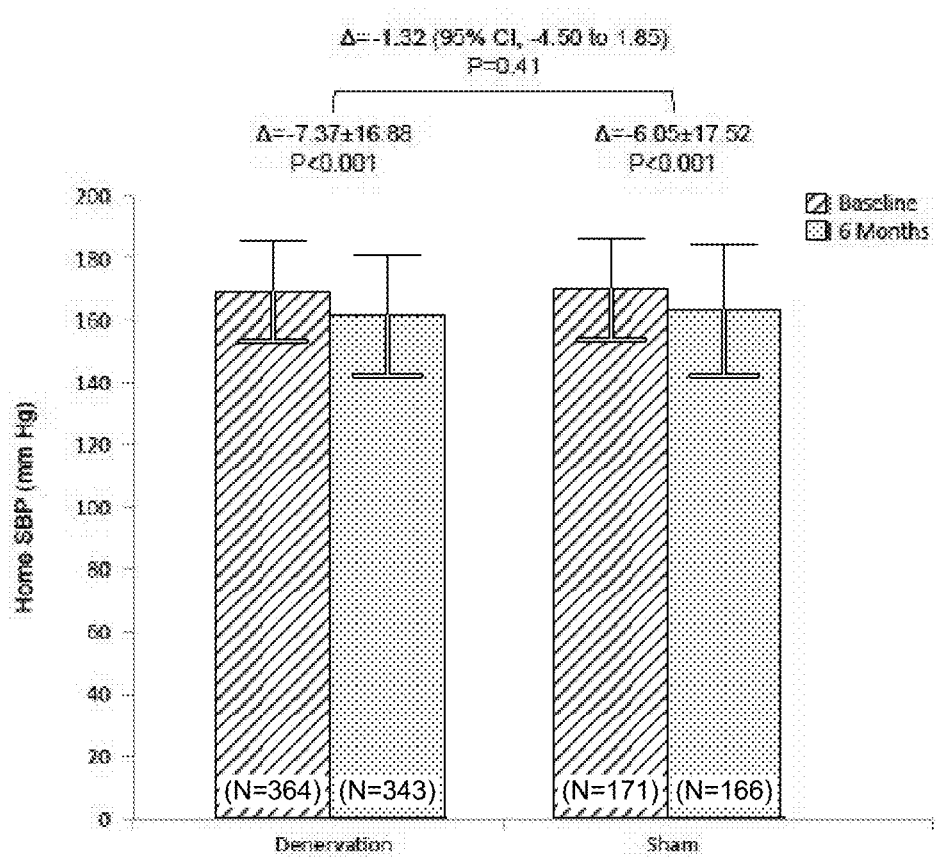

FIGS. 5A and 5B are display charts illustrating the results with regard to the primary efficacy end point (change in office systolic blood pressure at 6 months). As illustrated, a significant change from baseline to 6 months in office systolic blood pressure was observed in both study groups. The between-group difference (the primary efficacy end point) did not meet a test of superiority with a margin of 5 mm Hg. There was no significant between-group difference in the change in office blood pressure at 6 months: −14.13±23.93 mm Hg in the denervation group and −11.74±25.94 mm Hg in the sham-procedure group, for a difference of −2.39 mm Hg (95% confidence interval [CI], −6.89 to 2.12; P=0.26 with a superiority margin of 5 mm Hg). FIGS. 6A and 6B are display charts illustrating the results with regard to the secondary efficacy end point directed to a change in ambulatory blood pressure at 6 months. A significant change from baseline to 6 months in ambulatory 24-hour average systolic blood pressure was observed in both groups. The between-group difference (the secondary efficacy end point) did not meet a test of superiority with a margin of 2 mm Hg. The change in ambulatory blood pressure at 6 months was −6.75±15.11 mm Hg in the denervation group and −4.79±17.25 mm Hg in the sham-procedure group, for a difference of −1.96 mm Hg ((95% CI, −4.97 to 1.06); P=0.98 with a superiority margin of 2 mm Hg). FIG. 7 is a display chart showing the change in home systolic blood pressure for the RDN treatment and sham procedure control groups. As illustrated, there was no significant difference between the two groups with respect to home systolic blood pressure.

The observations regarding systolic blood pressure were consistent when diastolic blood pressure was examined. Table 6 shows the office, ambulatory, and home blood pressure measurements for both the RDN treatment and sham procedure control groups at baseline and at 6 months.

TABLE 6

Office, Ambulatory, and Home Blood Pressure Measurements

|  | Denervation Group | Sham Group | P-value |
| --- | --- | --- | --- |
| Baseline Office | N = 364 | N = 171 |  |
| SBP | 179.7 ± 16.1 | 180.2 ± 16.8 | 0.78 |
| DBP | 96.5 ± 16.6 | 98.9 ± 15.8 | 0.12 |
| Baseline Ambulatory | N = 360 | N = 167 |  |
| SBP | 159.1 ± 13.2 | 159.5 ± 15.3 | 0.78 |
| DBP | 88.0 ± 14.0 | 90.9 ± 14.4 | 0.03 |
| Baseline Home | N = 364 | N = 171 |  |
| SBP | 169.0 ± 15.9 | 169.1 ± 16.3 | 0.94 |
| DBP | 89.6 ± 15.9 | 92.9 ± 16.4 | 0.03 |
| 6 Months - Office | N = 353 | N = 171 |  |
| SBP | 165.6 ± 23.7 | 168.4 ± 28.6 | 0.26 |
| DBP | 89.5 ± 16.9 | 94.1 ± 17.7 | 0.01 |
| DBP change | −6.6 ± 11.9 | −4.6 ± 13.6 | 0.12 |
| 6 Months - Ambulatory | N = 329 | N = 162 |  |
| SBP | 151.8 ± 16.0 | 153.9 ± 19.1 | 0.24 |
| DBP | 83.1 ± 13.7 | 87.4 ± 14.6 | <0.01 |
| DBP change | −4.1 ± 9.2 | −3.1 ± 10.1 | 0.28 |
| 6 Months - Home | N = 343 | N = 166 |  |
| SBP | 161.1 ± 19.2 | 162.8 ± 21.1 | 0.36 |
| DBP | 86.0 ± 16.6 | 90.0 ± 16.4 | 0.01 |
| DBP change | −2.9 ± 9.1 | −2.8 ± 8.2 | 0.94 |

The proportions of patients with a reduction in office systolic or diastolic blood pressure of at least 5 mm Hg or at least 10 mm Hg are shown in Table 7.

TABLE 7

Systolic and Diastolic Blood Pressure Response Based on
≥5 mm Hg and ≥10 mm Hg Reduction From Baseline at 6 Months

| Effectiveness Measures | Renal Denervation Group (N = 364 Patients) | Sham-Procedure Group (N = 171 Patients) | P-Value |
|---|---|---|---|
| Reduction in Office SBP at 6 months | | | |
| ≥5 mm Hg | 66.9% (234/350) | 55.6% (94/169) | 0.02 |
| ≥10 mm Hg | 58.3% (204/350) | 48.5% (82/169) | 0.04 |
| Reduction in Office DBP at 6 months | | | |
| ≥5 mm Hg | 55.1% (193/350) | 43.8% (74/169) | 0.02 |
| ≥10 mm Hg | 37.7% (132/350) | 28.4% (48/169) | 0.04 |

The responses with regard to systolic and diastolic blood pressure were significantly greater in the denervation group than in the sham-procedure group.

Figure 8:
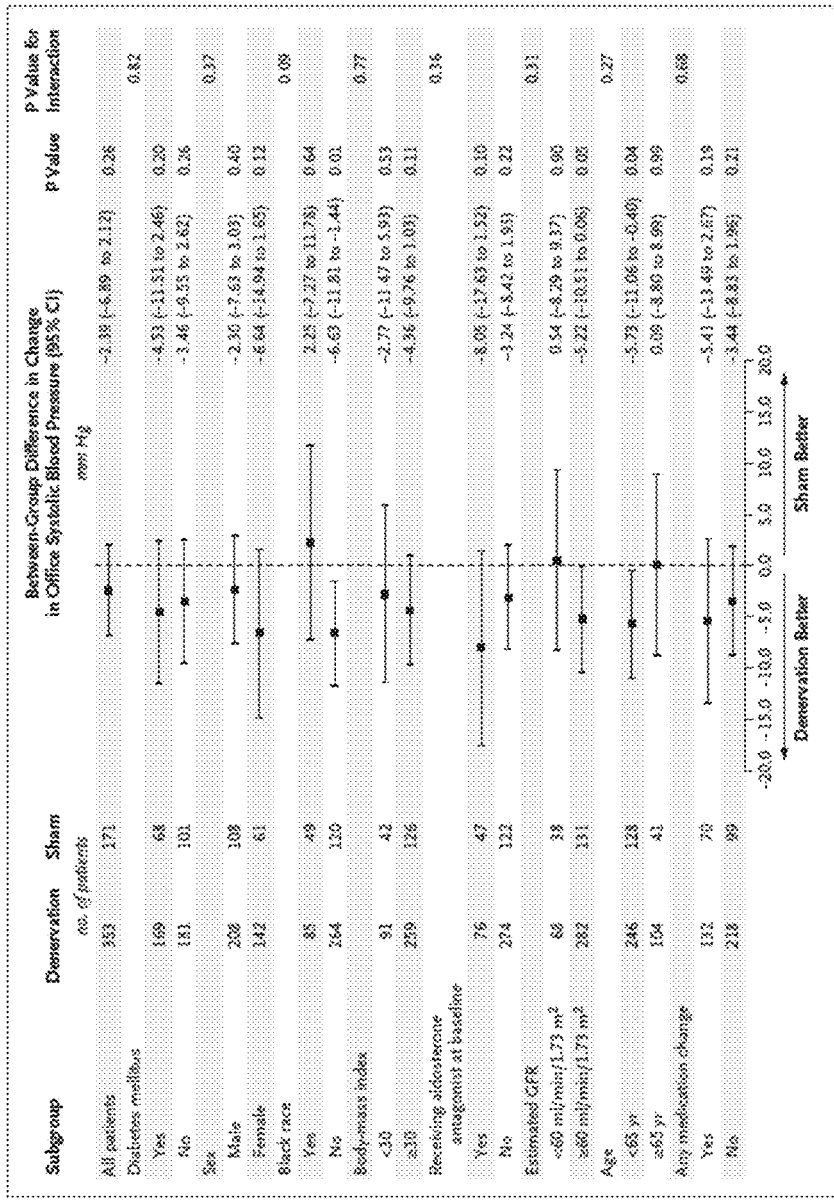

FIG. 8 is a display chart illustrating the change in office systolic blood pressure from baseline to 6 months in various prespecified subgroups and showing the difference between the RDN treatment and sham procedure control groups. Although the differences between the groups and within some subgroups were nominally significant, the absolute magnitude of the differences was small (<10 mm Hg). The differences were not significant with the use of a superiority margin of 5 mm Hg or after adjustment for multiple comparisons. There were no significant differences between the denervation and sham-procedure groups as a function of baseline systolic blood pressure. There was also no significant between-group difference in the change in heart rate from baseline to 6 months (−3.8±11.2 beats per minute in the denervation group and −2.7±10.9 beats per minute in the sham-procedure group, P=0.30).

As shown in Table 8, there were no significant differences between the RDN treatment and sham procedure control groups in kidney function at any time point; there were also no significant differences in the subgroup of patients with an estimated glomerular filtration rate (eGFR) of less than 60 ml per minute per 1.73 m² of body-surface area.

TABLE 8

Renal Function at Baseline and Post-Procedure

| Measure | Renal Denervation Group (N = 364) | Sham-Procedure Group (N = 171) | P Value |
|---|---|---|---|
| Baseline | | | |
| Serum Creatinine (mg/dl) | 1.03 ± 0.24 | 1.05 ± 0.25 | 0.42 |
| Cystatin C (mg/l) | 0.91 ± 0.26 | 0.87 ± 0.22 | 0.04 |
| eGFR (ml/min/1.73 m²) | 72.78 ± 15.67 | 74.03 ± 18.74 | 0.45 |
| Measurement at 1 Month | | | |
| Serum Creatinine (mg/dl) | 1.07 ± 0.27 | 1.07 ± 0.29 | 0.77 |
| Cystatin C (mg/l) | 0.92 ± 0.27 | 0.91 ± 0.26 | 0.54 |
| eGFR (ml/min/1.73 m²) | 70.70 ± 16.39 | 72.69 ± 18.02 | 0.21 |
| Change at 1 Month | | | |
| Serum Creatinine (mg/dl) | 0.04 ± 0.14 | 0.03 ± 0.16 | 0.60 |
| Cystatin C (mg/l) | 0.01 ± 0.20 | 0.03 ± 0.22 | 0.23 |
| eGFR (ml/min/1.73 m²) | −2.15 ± 10.77 | −1.47 ± 11.23 | 0.51 |
| Measurement at 6 Months | | | |
| Serum Creatinine (mg/dl) | 1.07 ± 0.30 | 1.08 ± 0.30 | 0.80 |
| Cystatin C (mg/l) | 0.97 ± 0.30 | 0.95 ± 0.28 | 0.31 |
| eGFR (ml/min/1.73 m²) | 70.59 ± 17.36 | 72.42 ± 19.00 | 0.28 |
| Change at 6 Months | | | |
| Serum Creatinine (mg/dl) | 0.04 ± 0.19 | 0.03 ± 0.18 | 0.47 |
| Cystatin C (mg/l) | 0.06 ± 0.24 | 0.07 ± 0.26 | 0.63 |
| eGFR (ml/min/1.73 m²) | −2.12 ± 12.91 | −1.72 ± 12.14 | 0.74 |

Values are expressed as n (%) or mean ± SD; eGFR denotes estimated glomerular filtration rate.

There was no significant between-group difference in the change in glycated hemoglobin levels from baseline to 6 months overall (0.06±0.93% in the denervation group and −0.06±0.87% in the sham-procedure group, P=0.19) or in the subgroup of patients with diabetes (0.12±1.15% in the denervation group and −0.22±1.14% in the sham-procedure group, P=0.051).

Attempts at correlation and assessment of successful ablation of renal nerves with the Symplicity™ renal denervation system and systolic blood pressure outcomes could be based, at least in part, on documentation of impedance drop and energy delivery from the RF generator as well as visualization of arterial notches following the ablation procedure. Correlation/assessment may also be based on documentation of significant reductions in renal NE spillover and MSNA in patients with hypertension following RDN (Krum, H., et. al., 2009, Lancet 373:1275-81).

Renal artery notching caused by edema post-procedure was observed on angiography following the denervation procedure. Table 9, for example, shows the percentages of patients who had "notching" on angiography, signifying energy delivery sufficient to cause spasm of the artery.

TABLE 9

Notching Following Renal Denervation

| | # notches | | | | | | | | | | |
|---|---|---|---|---|---|---|---|---|---|---|---|
| | 0 | 1 | 2 | 3 | 4 | 5 | 6 | 7 | 8 | 9 | Total |
| Denervation | 149 | 77 | 57 | 30 | 27 | 9 | 5 | 4 | 1 | 1 | 360 |
| (%) | (41.4) | (21.4) | (15.8) | (8.3) | (7.5) | (2.5) | (1.4) | (1.1) | (0.3) | (0.3) | |

Mean # number of notches in the denervated group: 1.41 ± 1.7.

This has been shown to resolve over time following the treatment. Such lesions have also been assessed using optical coherence tomography following denervation. No relationship was observed between the number of denervation notches and systolic blood pressure reduction.

Figure 9:
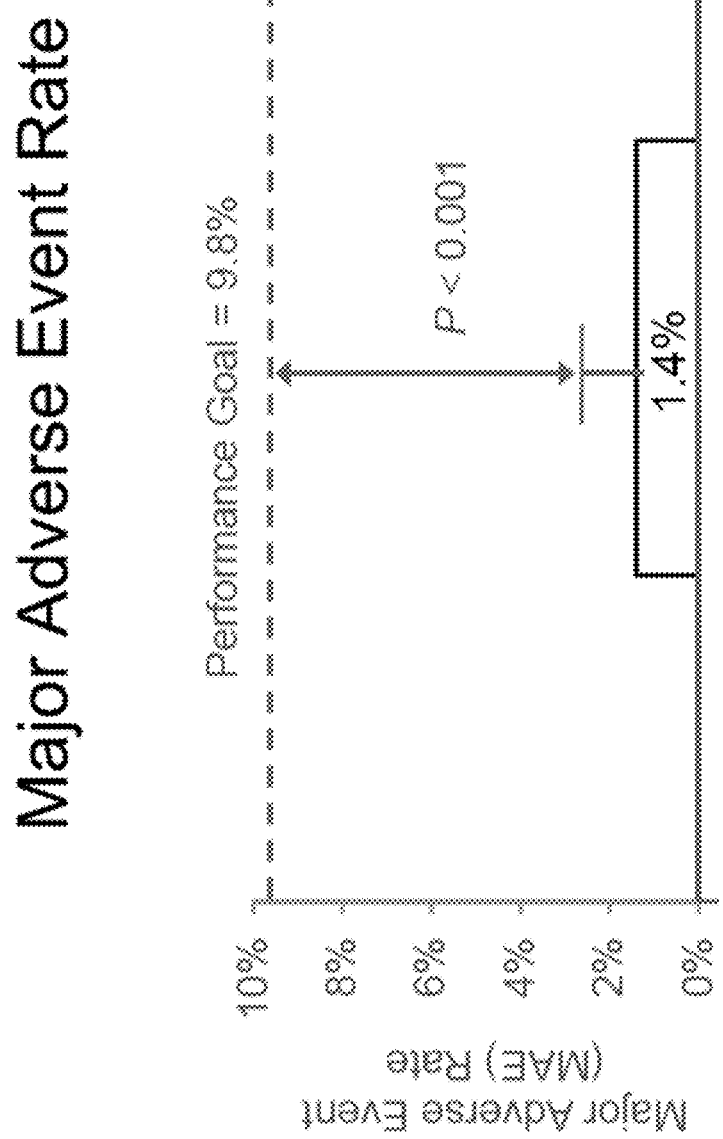

The primary safety endpoint was the composite endpoint of death, renal injury, vascular complications and embolic tissue injury to 1 month and renal artery stenosis to 6 months. A performance goal established from renal artery stenting required the MAE rate for safety be <9.8%. This requires the observed MAE rate to be <0.7, given the expected confidence interval for this endpoint. Table 10 shows the MAE rates for the RDN treatment and sham procedure control groups achieved at 1 month and 6 months. FIG. 9 is a display chart illustrating the MAE rate for the RDN treatment group at 1 month post-treatment.

TABLE 10

Major Adverse Event Rates at 1 Month and 6 Months

| Safety Measures | Renal Denervation (N = 364) | Sham Procedure (N = 171) | Difference (95% CI) | P |
|---|---|---|---|---|
| MAE at 30 days | 1.4% (5/361) | 0.6% (1/171) | 0.8% (−0.9%, 2.5%) | 0.67 |
| MAE at 6 mo | 4.0% (14/354) | 5.8% (10/171) | −1.9% (−6.0%, 2.2%) | 0.37 |

Table 11 shows the primary safety end point and other safety events. There were few major adverse events in the trial: five in the denervation group (1.4%) and one in the sham-procedure group (0.6%), for a difference of 0.8 percentage points (95% CI, −0.9 to 2.5; P=0.67).

TABLE 11

Safety End Points

| End point | Renal-Denervation Group no. of patients/total no. (%) | Sham-Procedure Group no. of patients/total no. (%) | Percentage-Point Difference (95% CI) |
|---|---|---|---|
| Major adverse event† | 5/361 (1.4) | 1/171 (0.6) | 0.8 (−0.9 to 2.5) |
| Composite safety end point at 6 mo‡ | 14/354 (4.0) | 10/171 (5.8) | −1.9 (−6.0 to 2.2) |
| Specific event within 6 mo | | | |
| Death | 2/352 (0.6) | 1/171 (0.6) | 0.0 (−1.4 to 1.4) |
| Myocardial infarction | 6/352 (1.7) | 3/171 (1.8) | 0.0 (−2.4 to 2.3) |
| New-onset end-stage renal disease | 0/352 | 0/171 | — |
| Increase in serum creatinine of >50% from baseline | 5/352 (1.4) | 1/171 (0.6) | 0.8 (−0.8 to 2.5) |
| Embolic event resulting in end-organ damage | 1/352 (0.3) | 0/171 | 0.3 (−0.3 to 0.8) |
| Renal-artery intervention | 0/352 | 0/171 | — |
| Vascular complication requiring treatment | 1/352 (0.3) | 0/171 | 0.3 (−0.3 to 0.8) |
| Hypertensive crisis or emergency | 9/352 (2.6) | 9/171 (5.3) | −2.7 (−6.4 to 1.0) |
| Stroke | 4/352 (1.1) | 2/171 (1.2) | 0.0 (−2.0 to 1.9) |
| Hospitalization for new-onset heart failure | 9/352 (2.6) | 3/171 (1.8) | 0.8 (−1.8 to 3.4) |
| Hospitalization for atrial fibrillation | 5/352 (1.4) | 1/171 (0.6) | 0.8 (−0.8 to 2.5) |
| New renal-artery stenosis of >70% | 1/332 (0.3) | 0/165 | 0.3 (−0.3 to 0.9) |

\* CI denotes confidence interval.
†The primary safety end point was a composite of major adverse events, defined as death from any cause, end-stage renal disease, an embolic event resulting in end-organ damage, renal-artery or other vascular complications, or hypertensive crisis within 30 days or new renal-artery stenosis of more than 70% within 6 months. The objective performance criterion for the primary safety end point was a rate of major adverse events of 9.8%, which was derived from historical data. The rate in the renal-denervation group was 1.4% with an upper boundary of the one-sided 95% CI of 2.9%; therefore, the performance criterion was met with a P value of <0.001.
‡This end point was a composite of death from any cause, end-stage renal disease, an embolic event resulting in end-organ damage, renal-artery or other vascular complications, hypertensive crisis, or new renal-artery stenosis of more than 70% within 6 months.

Referring to Tables 10 and 11 and FIG. 9 together, the primary safety endpoint was achieved in this example. The MAE for the RDN group was 1.4% at 1 month and 4.0% at 6 months post-treatment.

Additional Observations (6 Months)

Figure 10:
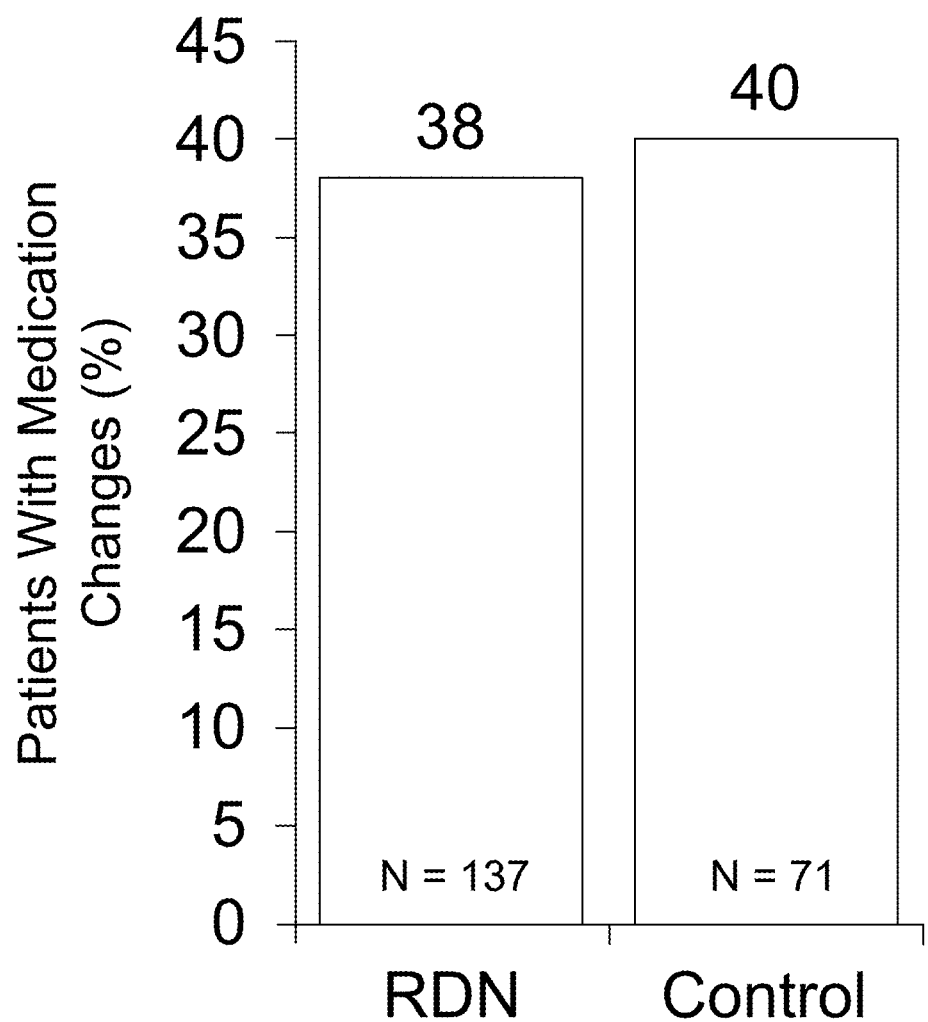

Several factors may have contributed to the results. For example, being enrolled and closely monitored in a clinical trial, as well as blinded to treatment, the patients may have improved or modified their lifestyle and drug adherence. Additionally, patients who were not otherwise on a maximum tolerated medication dosage were placed on a maximum tolerated dosage regimen. Further, and as shown in FIG. 10, the protocol called for a mandated maximum dosage of medication with no medication changes permitted, however, during the trial, approximately 40% of patients (n=208) required medication changes with 69% of the first medication changes were deemed medically necessary.

Figure 11:
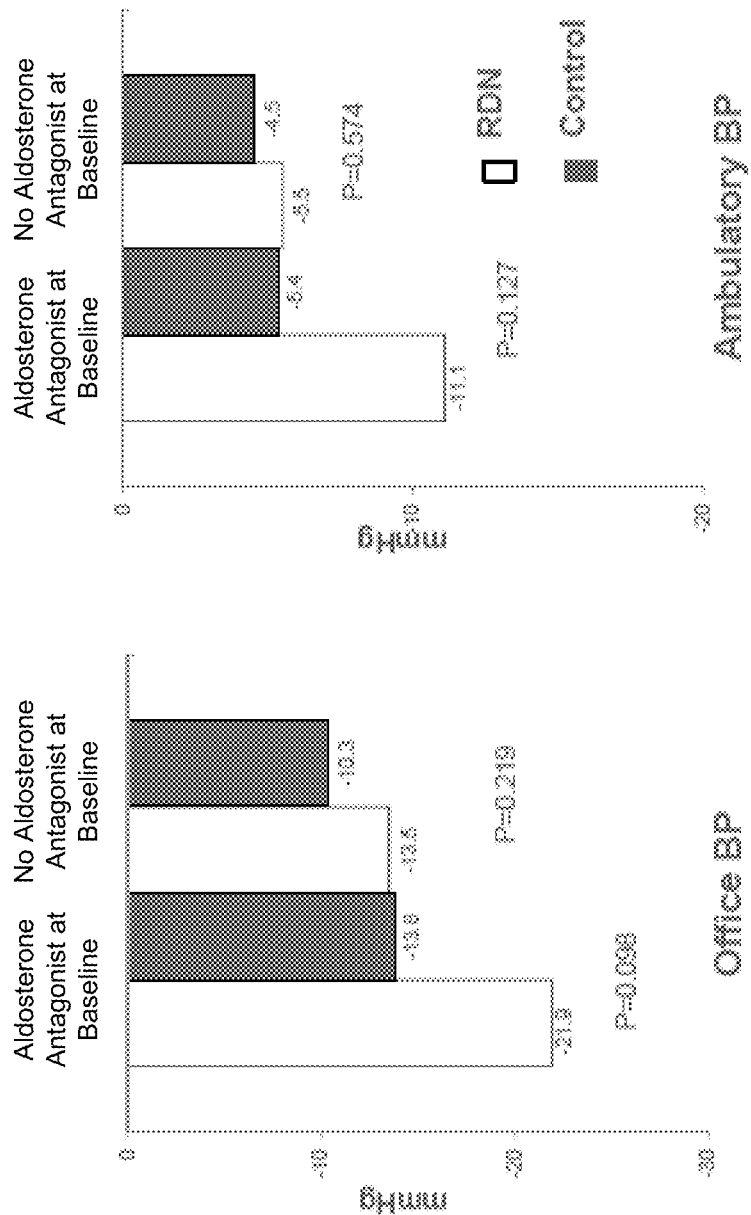

The results also show that RDN treatment group patients prescribed and taking an aldosterone antagonist medication at baseline and during the trial 6 month period had a greater decrease in Office and Ambulatory blood pressure readings compared to both RDN treatment group patients not prescribed and taking an aldosterone antagonist at baseline and to sham procedure control group patients regardless of aldosterone antagonist medication. FIG. 11 is a display chart illustrating the efficacy results of RDN treatment group patients taking aldosterone antagonist medication at baseline. As illustrated in FIG. 11, patients having received RDN and taking an aldosterone antagonist show approximately a 21.9 mm Hg decrease in systolic blood pressure compared to a 13.5 mm Hg decrease in systolic blood pressure in patients having received RDN without taking an aldosterone antagonist.

Figure 12A:
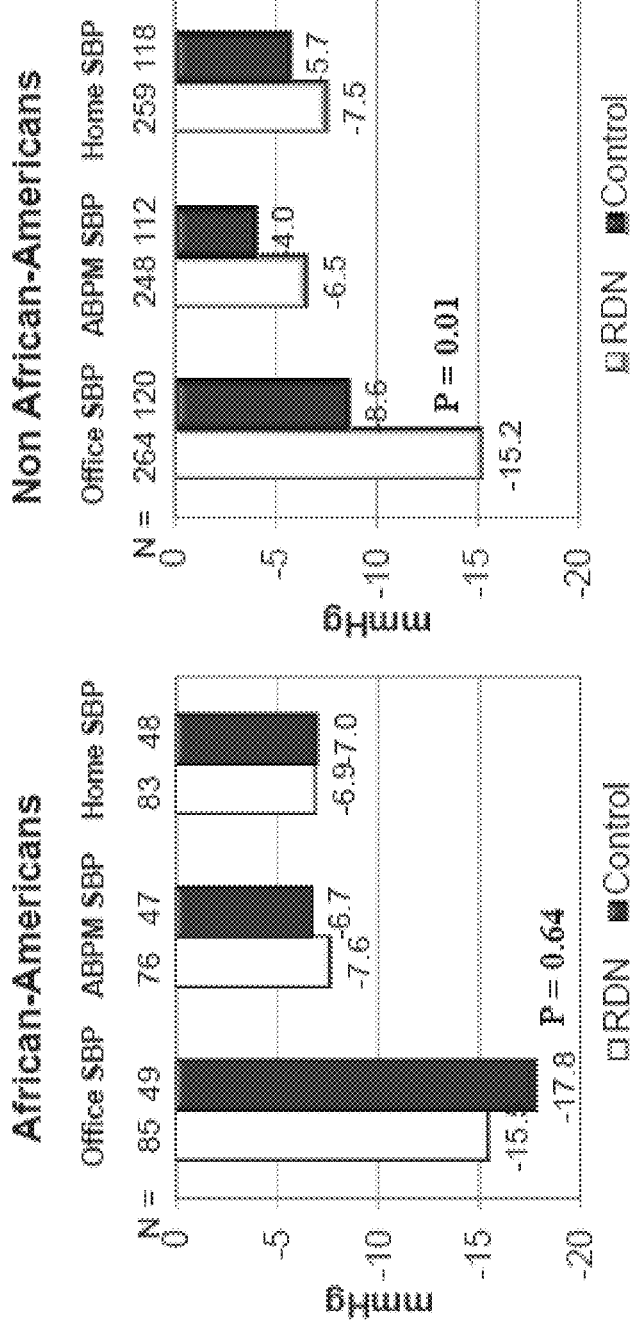
Figure 12B:
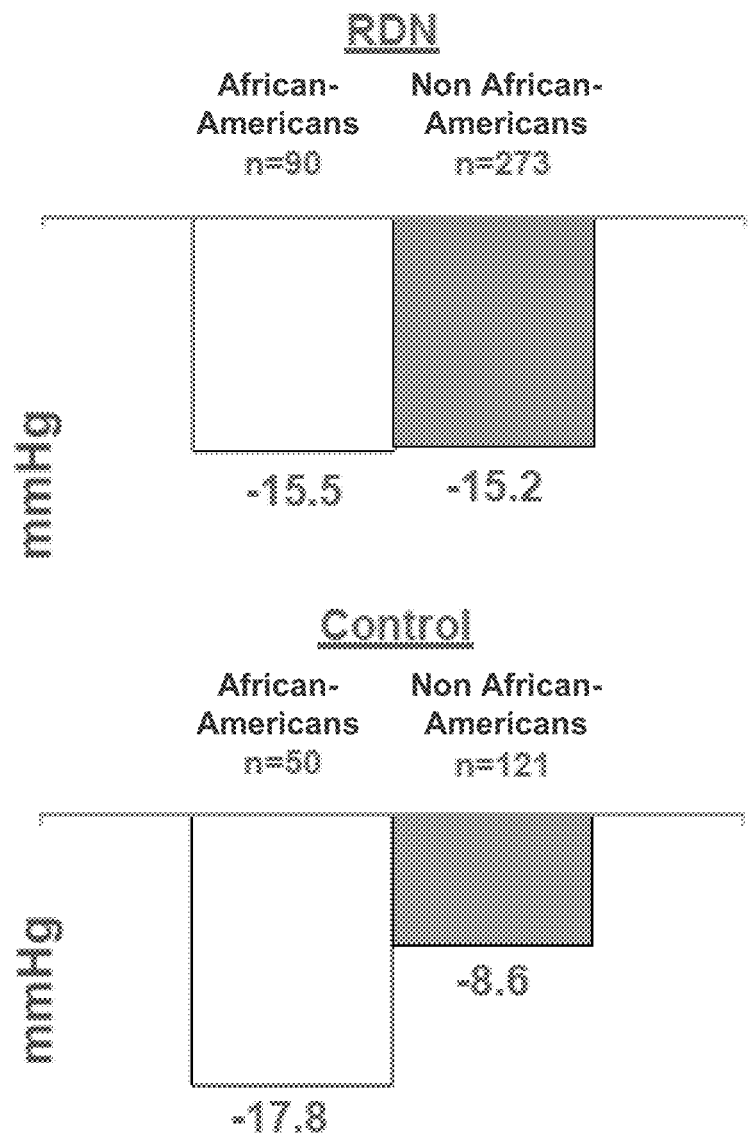

FIGS. 12A and 12B are display charts illustrating the impact of race demographics on the efficacy of RDN in this trial. For example, FIG. 12A shows that patients who are African American are less likely to show a difference in systolic blood pressure decrease between the RDN treatment and sham procedure control groups. For patients that do receive RDN, there was no significant difference between African American patients and non-African American patients (FIG. 12B). For example, of the patients who received RDN, African American patients had a 15.5 mm Hg decrease in systolic blood pressure and non-African American patients had a 15.2 mm Hg decrease in systolic blood pressure (FIG. 12B). Additionally, FIG. 12B shows that of the patients in the sham procedure control group, African American patients get a greater decrease in systolic blood pressure (e.g., −17.8 mm Hg) when compared to non-African American patients (e.g., −8.6 mm Hg) when on a maximum medication dose schedule.

Figure 13:
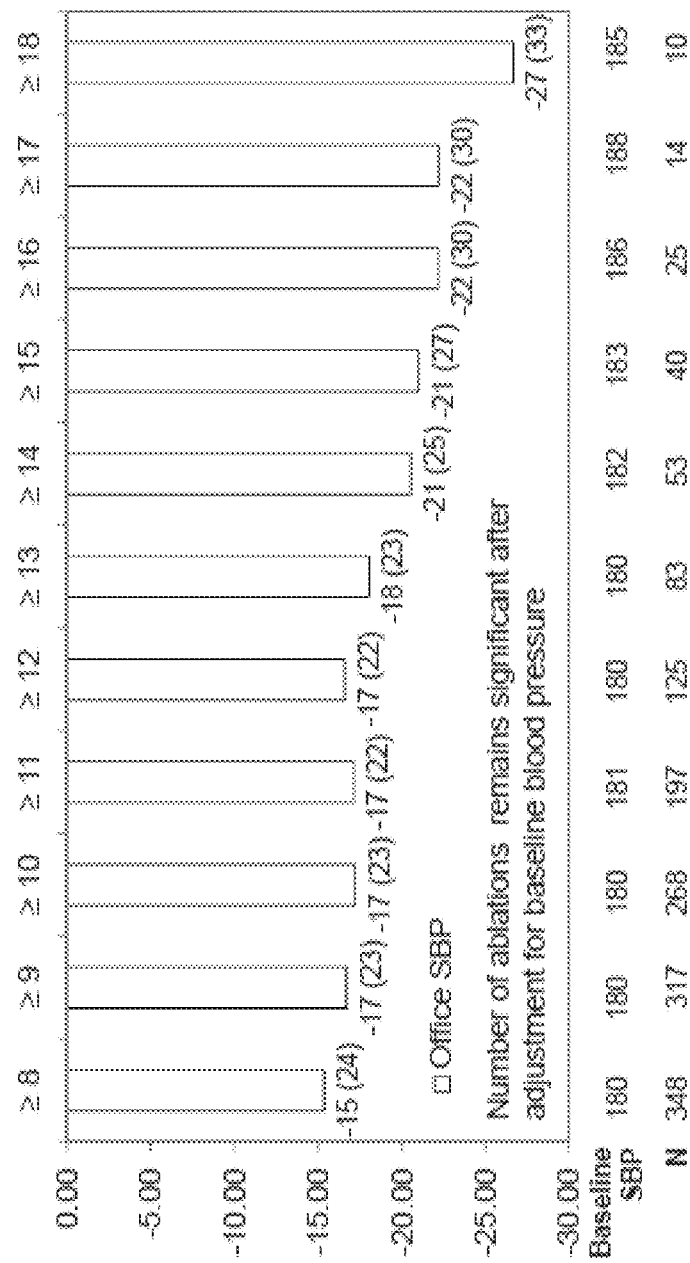

FIG. 13 is a display chart showing that the number of total ablations affects a patient's office systolic blood pressure measurement. For example, the greater the number of ablations a patient received correlated with a greater decrease in the patients' systolic blood pressure post-treatment.

Figure 14:
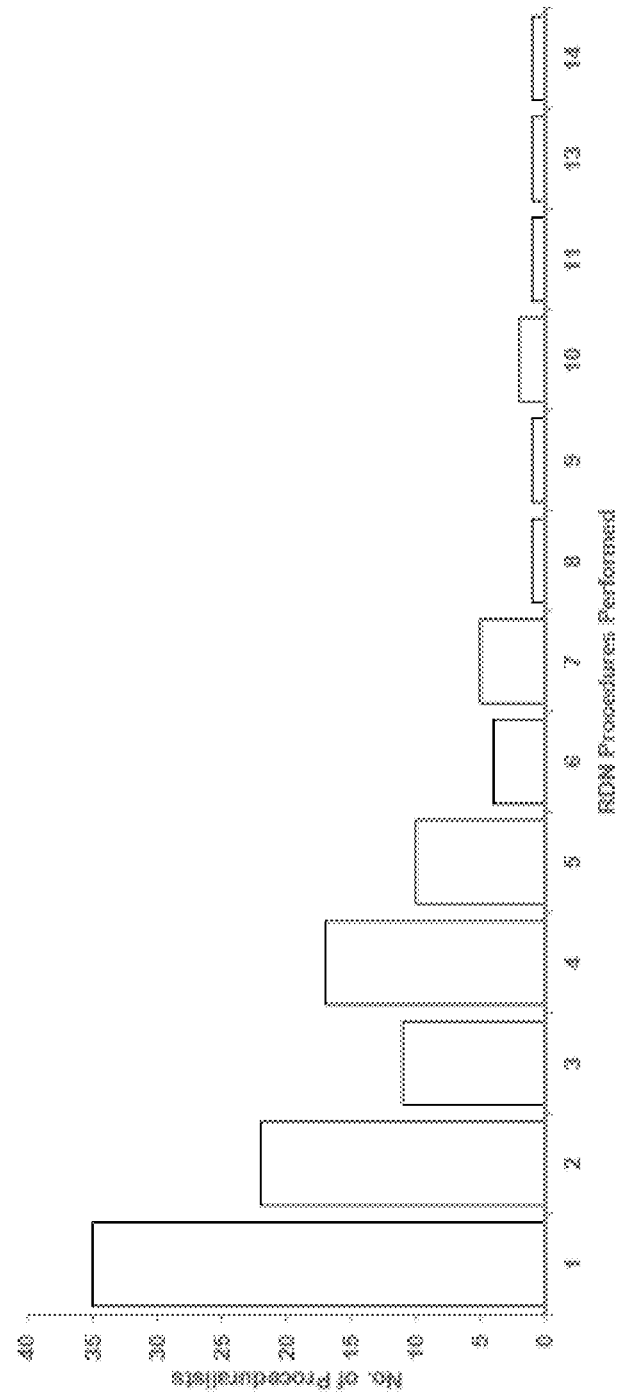

Additional factors may include procedural variability introduced by including a greater number of trial sites and proceduralists (i.e., medical practitioners performing the RDN procedure). In order to assess the possible impact of operator training and experience on results, several analyses were performed. FIG. 14 is a display chart showing the number of proceduralists performing 1 procedure, <5 procedures or ≥5 procedures, etc. Overall, >50% of proceduralists performed ≤2 RDN procedures in this trial. Outcomes for early and later procedures were compared to assess the presence of a learning curve. Additionally, outcomes for operators who did <5 procedures were compared with outcomes of operators who did or ≥5 procedures. Overall, there were 111 operators who did at least one procedure (31% did only 1 procedures) and 26 operators who did ≥5 procedures. The average office, home, and ambulatory systolic blood pressure drops for the first RDN procedures of all operators were close to or slightly higher than the overall average for the study. Furthermore there was no difference in the results of early versus later procedures for the operators who performed ≥5 procedures. Finally, there were 183 patients treated by physicians who performed ≥5 procedures and 181 patients treated by physicians who did <5 procedures. There was no difference in the 6 month change in office (−14.8±24.5 vs −15.9±23.4, P=0.67), ambulatory (−7.0±14.6 vs −6.5±15.7, P=0.75) or home (−8.0±17.6 vs −6.7±16.1, P=0.49) systolic blood pressure.

Figure 15:
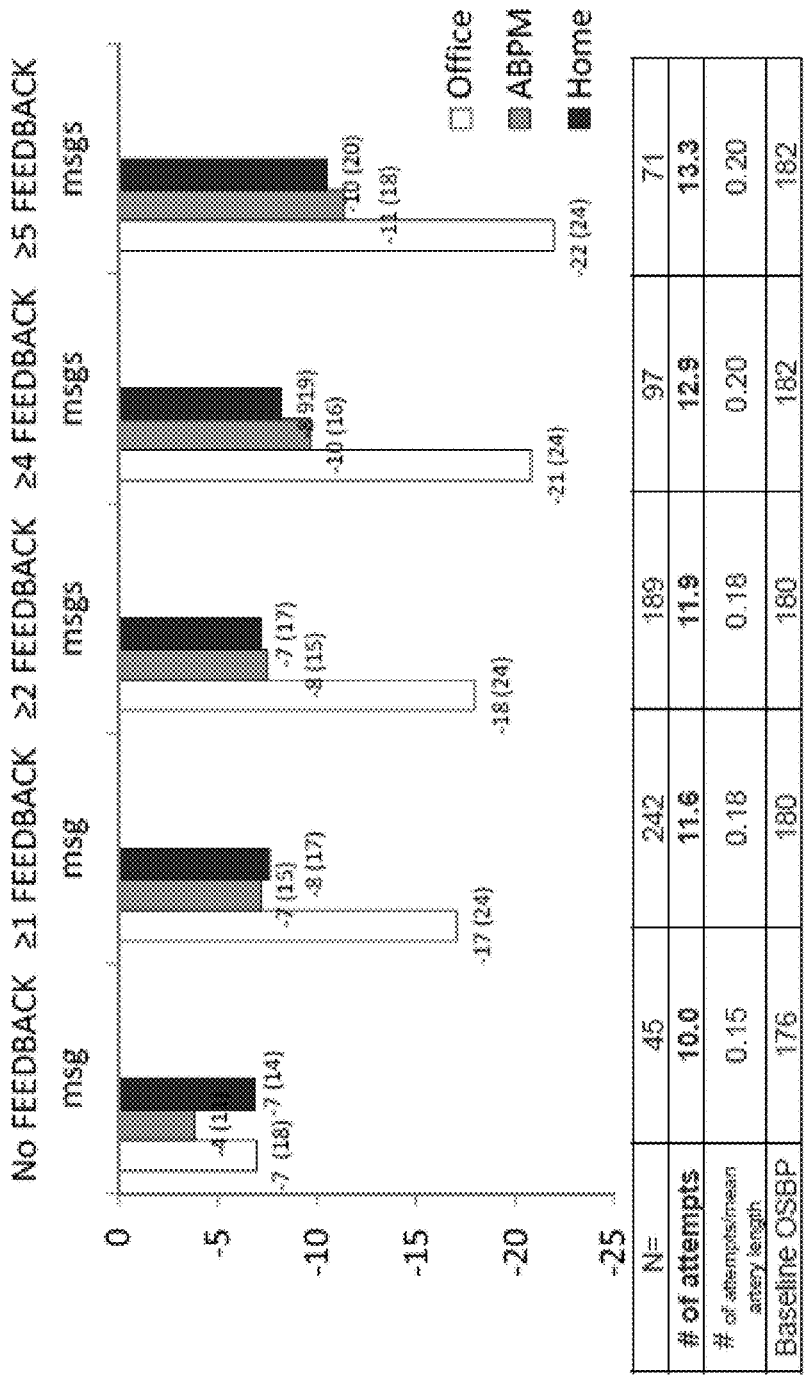

FIG. 15 is a display chart showing the impact of generator feedback messages on systolic blood pressure following RDN. During the RDN procedure, poor contact with the interior wall of the renal artery will cause the Symplicity™ RF generator to issue an operator message. When such a message was received, the clinician would reposition/move the electrode and repeat an ablation cycle at that treatment site. As shown in FIG. 15, such feedback messages with subsequent additional ablation cycles correlate with an increased decrease in systolic blood pressure.

Figure 16:
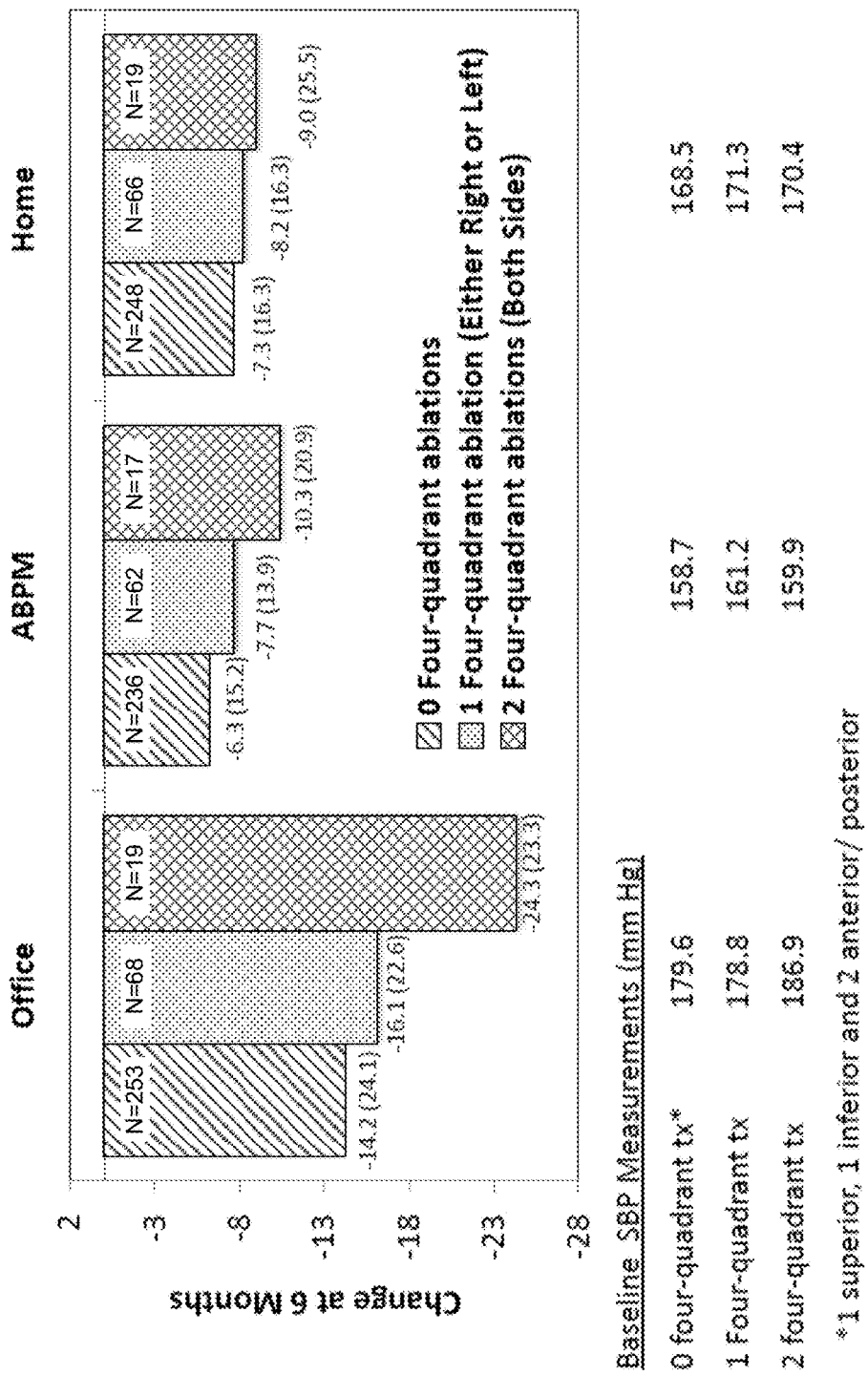

FIG. 16 is a display chart showing the impact of ablation pattern on systolic blood pressure change at 6 months following renal denervation procedure. As shown in FIG. 16, a four-quadrant ablation pattern (e.g., at least one ablation in each of an inferior, anterior, superior and posterior position around the interior wall) correlates with an increased decrease in office, 24-hour ambulatory, and home systolic blood pressure results. This decrease was further enhanced when patients received a four-quadrant ablation pattern on both the left- and right-side renal arteries.

Analysis of 24-hour ambulatory blood pressure measurements (ABPM) 6 months post randomization and treatment also revealed that renal artery denervation is correlated with an increased decrease in morning and night systolic BP for hypertensive patients. High nocturnal blood pressure and morning blood pressure surge are both associated with increased risk for stroke and cardiovascular complications. For example, the association of high daytime blood pressure with cardiovascular risk is attenuated by pharmacologic treatment but risk is not reduced when nocturnal blood pressure remains high. Average morning SBP (7 am to 9 am), maximum morning SBP (between 6 am and 10 am), average nocturnal SBP (1 am to 6 am), average peak nocturnal SBP (average of 3 highest SBPs between 1 am and 6 am) and average daytime SBP were calculated using pooled patient-level ABPM data. Six-month change in morning SBP parameters were compared between RDN treatment and control patients. Patient level data was pooled from the blinded, sham controlled trial for RDN presented in this example (n=535) and a separate, non-blinded, non-sham treated control study in Japan (n=41). A total of 386 patients (364 from HTN-3 and 22 from Japan) received RDN and 190 patients were in the control group (171 from HTN-3 and 19 from Japan). The average morning SBP was reduced −8.0±22.3 mmHg in the RDN group which was significantly more than the change in the control group (−3.5±22.2 mmHg, p=0.023). The maximum morning SBP change was −8.6±22.3 mmHg for RDN patients and −4.8±23.8 mmHg for controls (p=0.072). Furthermore, the change in average nocturnal and average peak nocturnal SBP was significantly greater in the RDN patients compared with the control patients; −6.3±18.1 vs −1.7±19.2 mmHg, p=0.008 for average nocturnal SBP and −6.7±20.0 vs −1.3±20.5 mmHg, p=0.004 for average peak nocturnal SBP. Average daytime SBP change was not significantly different between the RDN treatment and control groups (−7.1±16.0 vs −5.7±18.0 mmHg, p=0.349). This analysis demonstrated that renal artery denervation significantly reduced the morning and nighttime systolic blood pressure compared with control patients (e.g., patients not receiving RDN treatment). Accordingly, renal artery denervation is correlated with a greater reduction in an RDN-treated patient's systolic blood pressure during higher risk time periods than in a patient who did not receive treatment.

Results at 12 Months (6 Months Post Un-Blinding)

Figure 17:
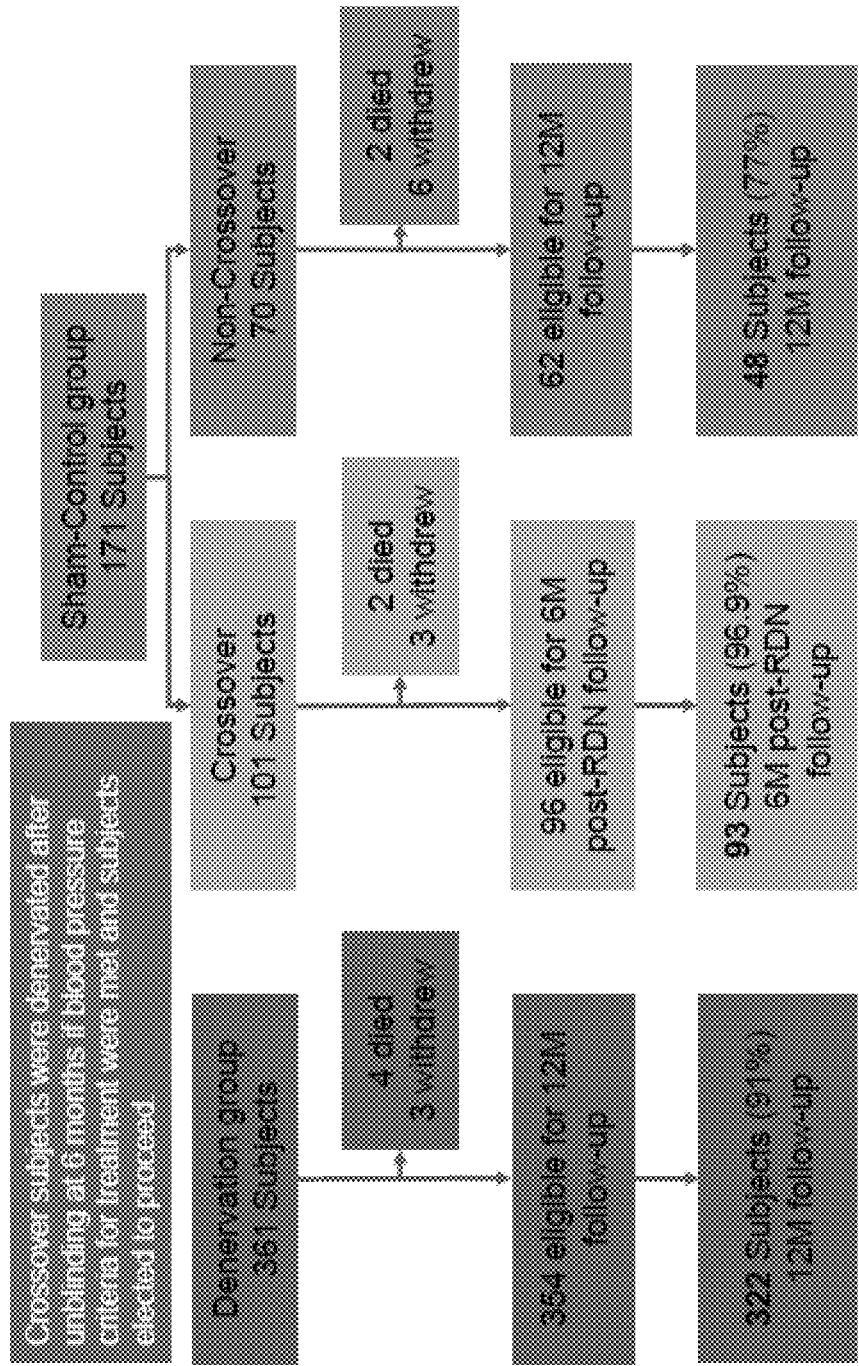

Six months following procedure, all patients and clinicians were un-blinded. Patients in the original sham control group (e.g., not treated with renal denervation) could elect to have RDN performed if eligible. Most patients not qualifying to crossover to the treatment group at the 6 month point (e.g., after un-blinding) had controlled office blood pressure at 6 months. FIG. 17 is a flow diagram illustrating the selection process for patients originally in the blinded sham control group to be included in a crossover group or to remain in the untreated group of patients. As illustrated in FIG. 17, out of the 171 patients in the sham control group, 101 patients received treatment at 6 months and 93 patients were evaluated 6 months following crossover treatment (e.g., 12 months post beginning the trial). There remained 70 non-crossover patients, of which 48 were evaluated at 12 months post beginning the trial. Of the original denervation treatment group (n=361), 322 patients were evaluated at 12 months post-procedure.

Table 12 below shows the baseline characteristics of the patients eligible for continued study inclusion up to 12 months post-initial procedure.

TABLE 12

Baseline characteristics of the study population

| Characteristic | Renal-Denervation (N = 364) | Crossover Group (N = 101) | Non-Crossover (N = 70) |
|---|---|---|---|
| Age - yr | 58 ± 10 | 55 ± 11 | 58 ± 12 |
| Male sex - no. (%) | 59.1 | 62.4 | 67.1 |
| Office systolic BP (mm Hg) | 180 ± 16 | 184 ± 19 | 176 ± 15 |
| 24-hr mean Systolic ABPM (mm Hg) | 159 ± 13 | 163 ± 16 | 155 ± 15 |
| Body-mass index (kg/m$^2$)† | 34.2 ± 6.5 | 33.0 ± 5.1 | 35.2 ± 7.8 |

TABLE 12-continued

Baseline characteristics of the study population

| Characteristic | Renal-Denervation (N = 364) | Crossover Group (N = 101) | Non-Crossover (N = 70) |
|---|---|---|---|
| Race - no/total no. (%)‡ | | | |
| White | 73.0 | 71.3 | 67.1 |
| Black or African Am. | 24.8 | 27.7 | 31.4 |
| Medical history - no. (%) | | | |
| Renal insufficiency§ | 9.6 | 9.9 | 10.0 |
| Renal-artery stenosis | 1.4 | 2.0 | 2.9 |
| Obstructive sleep apnea | 25.8 | 37.6 | 22.9 |
| Stroke | 8.2 | 11.9 | 10.0 |
| Type 2 Diabetes | 47.0 | 37.6 | 45.7 |
| Hypertensive Crisis | 23.1 | 20.8 | 24.3 |
| Hyperlipidemia | 69.5 | 63.4 | 67.1 |
| Current smoking | 9.9 | 14.9 | 8.6 |
| Prescribed antihypertensive drugs >10 yrs | 68.1 | 72.3 | 62.9 |

*Plus-minus values are means ± SD.
†The body-mass index is the weight in kilograms divided by the square of the height in meters.
‡Race was determined by self-report.
§Renal insufficiency was defined as an estimated glomerular filtration rate of less than 60 ml per minute per 1.73 m² of body-surface area.

Table 13 shows the number of prescribed antihypertensive medications for the renal denervation group, the crossover group and the non-crossover group at baseline, 6 months and 12 months following initial procedure.

TABLE 13

Prescribed Antihypertensive Medications

| | Renal-Denervation (N = 364) | Crossover Group (N = 101) | Non-Crossover (N = 70) |
|---|---|---|---|
| Baseline | 5.1 ± 1.4 | 5.2 ± 1.6 | 5.2 ± 1.4 |
| 6 Months | 5.0 ± 1.4 | 5.2 ± 1.6 | 5.1 ± 1.6 |
| 12 Months | 5.0 ± 1.6 | n/a | 4.9 ± 1.5 |

Table 14 shows the procedural characteristics for the renal denervation treatment group, the crossover group and the non-crossover group.

TABLE 14

Procedural Characteristics

| | Renal Denervation Group (N = 364) | Crossover Group (N = 101) | Non-Crossover Group (N = 70) |
|---|---|---|---|
| Procedure time (min.) | 93 ± 38 | 76 ± 30 | 56 ± 33 |
| Denervation time (min.) | 46 ± 15 | 46 ± 15 | n/a |
| Volume of contrast used (cc) | 177 ± 77 | 138 ± 60 | 81 ± 50 |
| Total # ablation attempts | 11.2 ± 2.8 | 11.2 ± 2.4 | n/a |
| # 120 second ablations | 9.2 ± 2.0 | 9.4 ± 1.9 | n/a |
| Hospitalization (days) | 1.0 ± 0.3 | 1.0 ± 0.1 | 1.1 ± 0.6 |

Values are expressed as n (%) or mean ± SD

Figure 18:
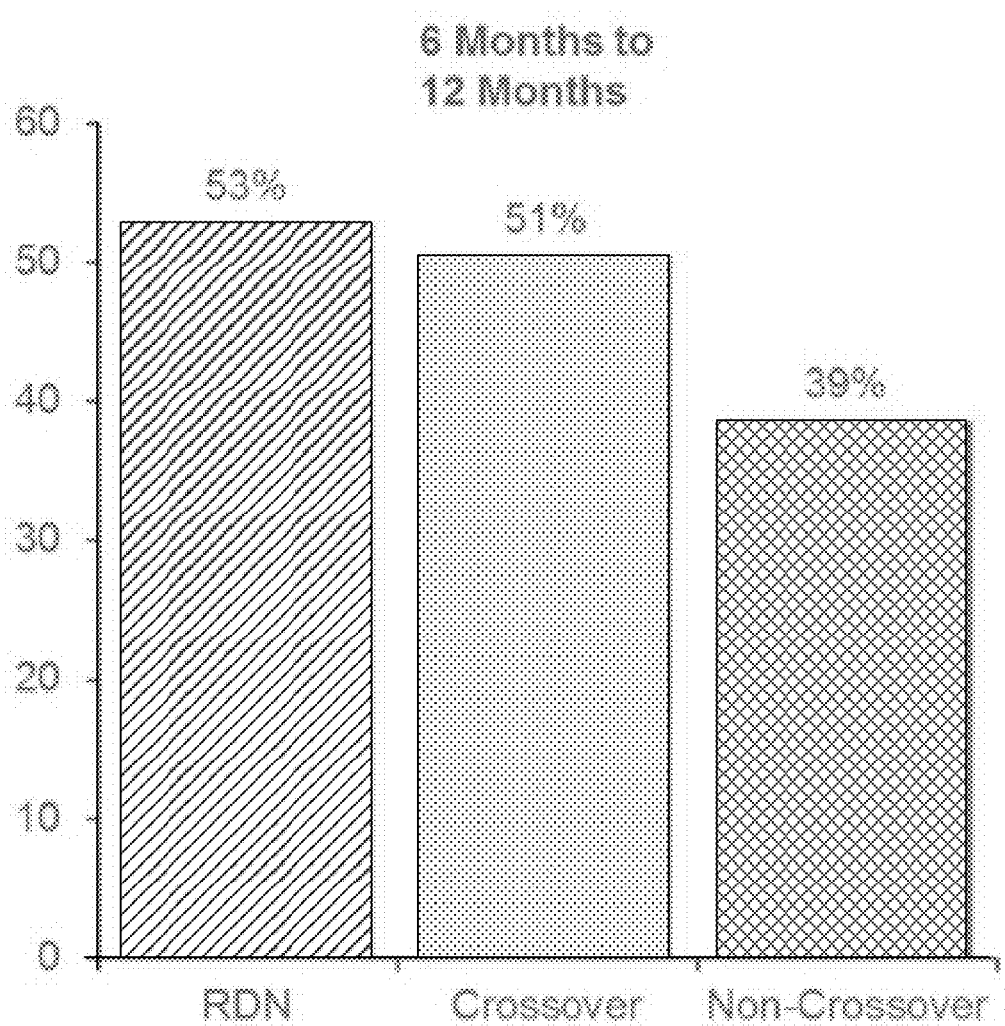

Patients in all groups were receiving an average of five antihypertensive medications, and on average, four of these medications were at maximally tolerated doses. While the numbers and types of antihypertensive medications at 6 months were similar to those at baseline in both the renal denervation treatment group and in the sham-procedure group (see Tables 3 and 4 above), medication changes did occur both prior to un-blinding (FIG. 10) as well as following un-blinding and up to 12 months following the original procedure, as shown in FIG. 18.

Table 15 shows the primary safety end point and other safety events. There were few major adverse events in the trial: five in the denervation group (1.4%) and one in the sham-procedure group (0.6%), for a difference of 0.8 percentage points (95% CI, −0.9 to 2.5; P=0.67).

TABLE 15

Safety End Points to 12 Months

| | Renal-Denervation n = 364 no. of patents/total no. (%) | Crossover* n = 101 | Non-crossover n = 70 |
|---|---|---|---|
| To 6 months | | | |
| Composite Safety to 6M (%) | 3.6 (13/358) | 5.2 (5/96) | 2.9 (2/70) |
| Death | 0.6 | 2.1 | 1.4 |
| New-onset end-stage renal disease | 0.0 | 0.0 | 0.0 |
| Embolic event resulting in end-organ damage | 0.3 | 0.0 | 0.0 |
| Renal-artery re-intervention | 0.0 | 0.0 | 0.0 |
| Vascular complication requiring treatment | 0.3 | 0.0 | 0.0 |
| Hypertensive crisis or emergency | 2.5 | 3.1 | 1.4 |
| New renal-artery stenosis of >70% | 0.0 | 0.0 | 0.0 |
| To 12 months | | | |
| Composite Safety to 6M (%) | 6.8 (24/355) | n/a | 7.2 (5/69) |
| Death | 1.8 | n/a | 3.6 |
| New-onset end-stage renal disease | 0.3 | n/a | 0.0 |
| Embolic event resulting in end-organ damage | 0.3 | n/a | 0.0 |
| Renal-artery re-intervention | 0.6 | n/a | 0.0 |
| Vascular complication requiring treatment | 0.3 | n/a | 0.0 |
| Hypertensive crisis or emergency | 4.8 | n/a | 5.5 |

*Safety from time of crossover procedure.

As such, renal denervation as demonstrated in the present blinded controlled study (e.g., up to 6 months post-procedure) and in long-term follow-up (e.g., 1 year post-procedure) yielded no long-term safety concerns.

Figure 19:
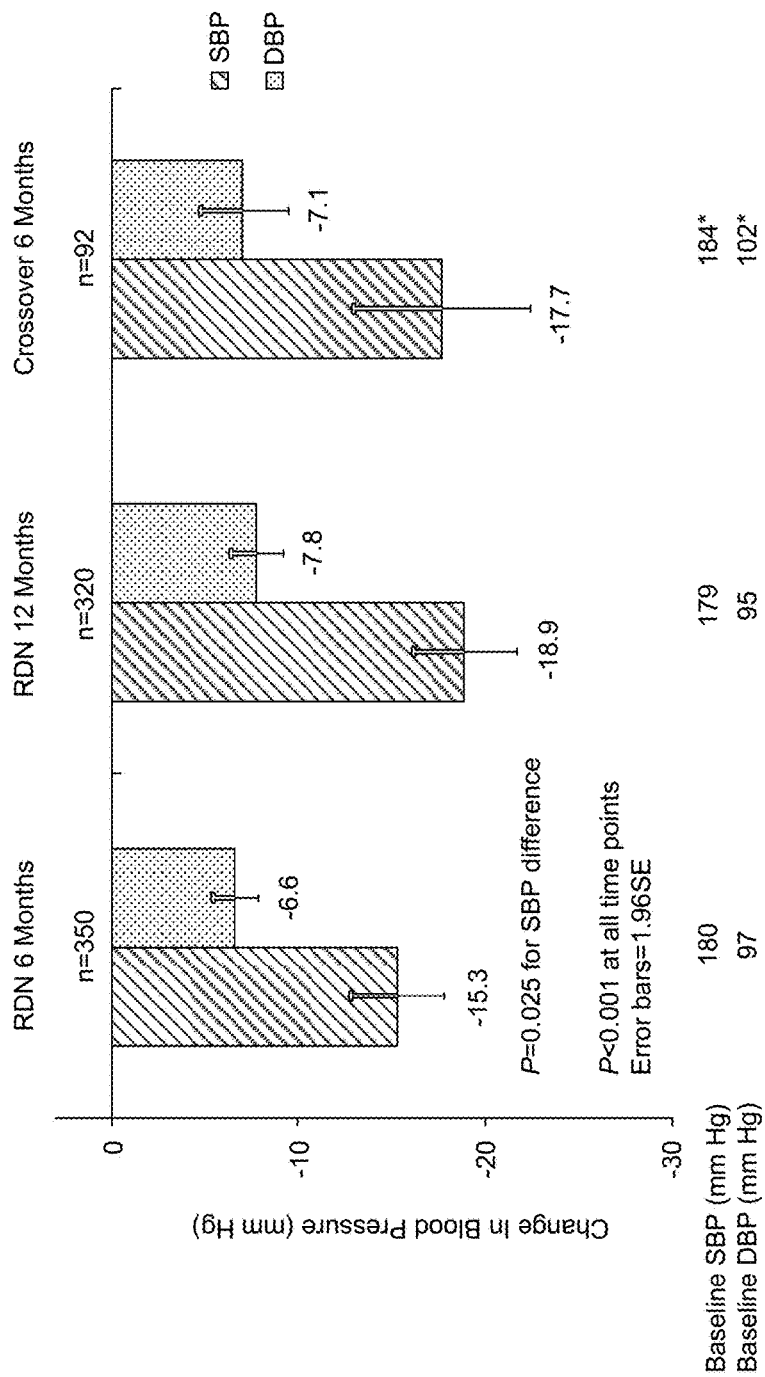
Figure 20:
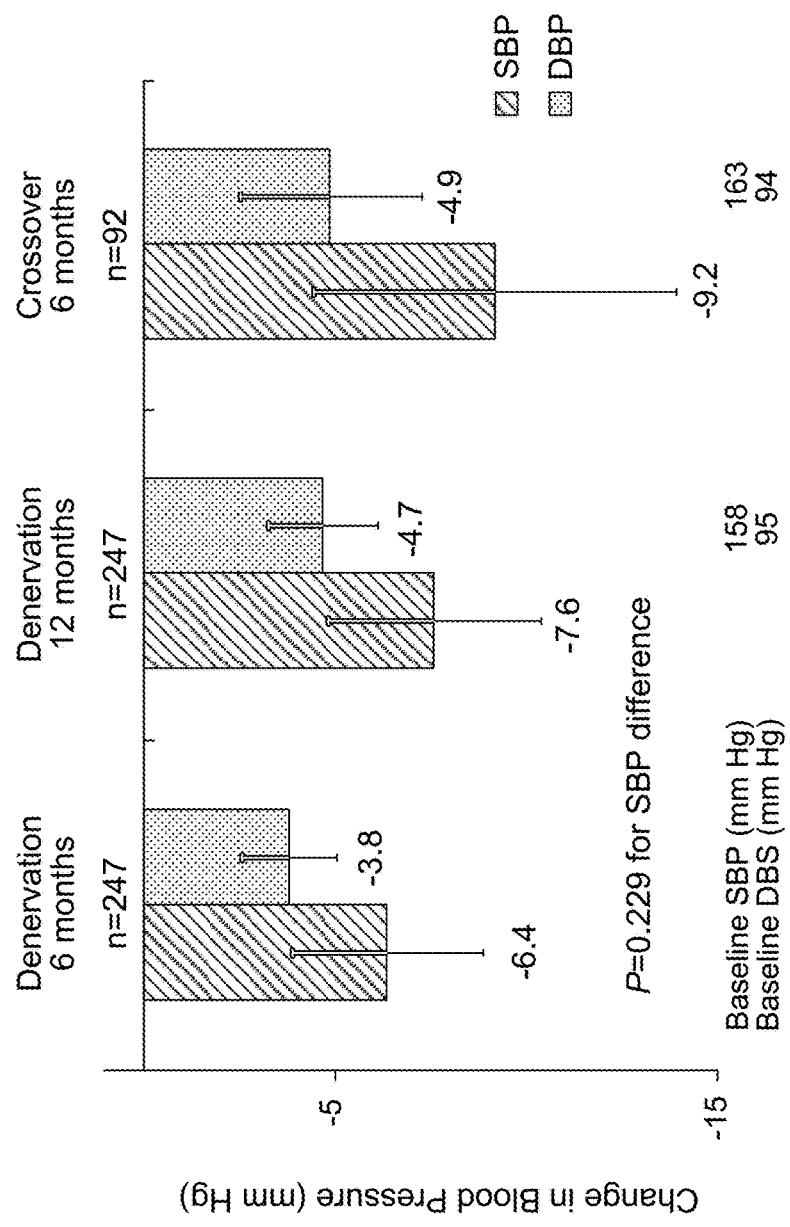

FIG. 19 is a display chart illustrating the change in office systolic and diastolic blood pressure readings among patients in the renal denervation group between baseline and 6 months and between baseline and 12 months post-procedure. FIG. 19 also illustrates the change in office systolic and diastolic blood pressure readings among crossover patients between the patient's baseline and at 6 months post-crossover procedure (12 months post sham procedure). As illustrated, the significant change from baseline to 6 months (−15.3 mm Hg SBP; −6.6 mm Hg DSB) in office systolic blood pressure was maintained and improved at 12 months (−18.9 mm Hg SBP; −7.8 mm Hg DSB). Office blood pressure readings of crossover patients demonstrated a −17.7 mm Hg reduction from original baseline office systolic blood pressure and a −7.1 mm Hg reduction from original baseline office diastolic blood pressure. FIG. 20 is display chart illustrating the change in 24-hour ambulatory systolic and diastolic blood pressure readings among patients in the renal denervation group between baseline and 6 months and between baseline and 12 months post-procedure. In the denervation group, the change in ambulatory blood pressure at 6 months was −6.4 mm Hg SBP and −3.8 DBP, and at 12 months was −7.6 mm Hg SBP and −4.7 mm Hg DBP. FIG. 20 also illustrates the change (−9.2 mm Hg SBP; −4.9 mm Hg DBP) in 24-hour ambulatory blood pressure readings for crossover patients between the patient's baseline blood pressure readings and at 6 months post-crossover procedure (12 months post sham procedure).

Example 2: Effect of Renal Denervation in a Real World Population of Patients with Uncontrolled Hypertension FIGS. 21A-24 and Tables 16-21 show results from a study to determine the effects of RDN in a real world population of 1000 patients with uncontrolled hypertension. As outlined below, this study demonstrated that RDN was followed by a significant reduction of office BP, which was closely related to baseline BP values, i.e., there was greater office SBP reduction in patients with higher baseline office SBP values. There was a reduction in ABP as well; however, the ABP drop was less pronounced than that of the office SBP reduction. There was, however, a close relationship between the extent of BP reduction and the baseline ambulatory SBP values. The study data further shows that the extent of BP reduction was not related to underlying cardiovascular comorbidities, that there were small reductions in antihypertensive medication use, and that the procedure was safe with low numbers of cardiovascular, renal or periprocedural complications. As such, renal denervation in a large real world population resulted in significant blood pressure reductions (e.g., 1 year post-procedure) with no long-term safety concerns.

For purpose of this study, these patients were stratified according to SBP at baseline of <140 mm Hg, 140-159 mm Hg, and ≥160 mm Hg. Additionally, patients were stratified according to baseline 24-hour ambulatory SBP (<135 mm Hg, 135-149 mm Hg, and ≥150 mm Hg) for assessment of ABP. True hypertension was defined as 24-hour ambulatory SBP ≥130 mm Hg or daytime ambulatory SBP ≥135 mm Hg and office SBP ≥140 mm Hg. Pseudo-hypertension was defined as ambulatory SBP <130 mm Hg and daytime ambulatory SBP <135 mm Hg and office SBP ≥140 mm Hg. Masked hypertension was defined as ambulatory SBP ≥130 mm Hg or daytime ambulatory SBP ≥135 mm Hg and office SBP <140 mm Hg.

RDN was performed using the Symplicity™ renal denervation system and the techniques described above with respect to Example 1. After the RDN treatment, office BP and 24 hour ABP were measured at 3 months, 6 months and 12 months follow-up visits. ABP captures and averages many values over 24 hours, and may thereby provide a more accurate assessment of blood pressure than office blood pressure measurements. Furthermore, it is believed that 24 hour average ABP are more closely related to end organ damage as well as a more sensitive predictor of morbidity and mortality. Protocol-defined safety events potentially related to RDN were documented at all visits. Patient follow-up is planned at 2 years and annually for up to 5 years. At six months, safety data were available for 913 patients and office BP data were available for 760 patients out of the 1000 consecutively enrolled patients. At 12 months, safety, office BP and 24 hour ABP data were available for 740 patients of the original 1000 consecutively enrolled patients.

Figure 21A:
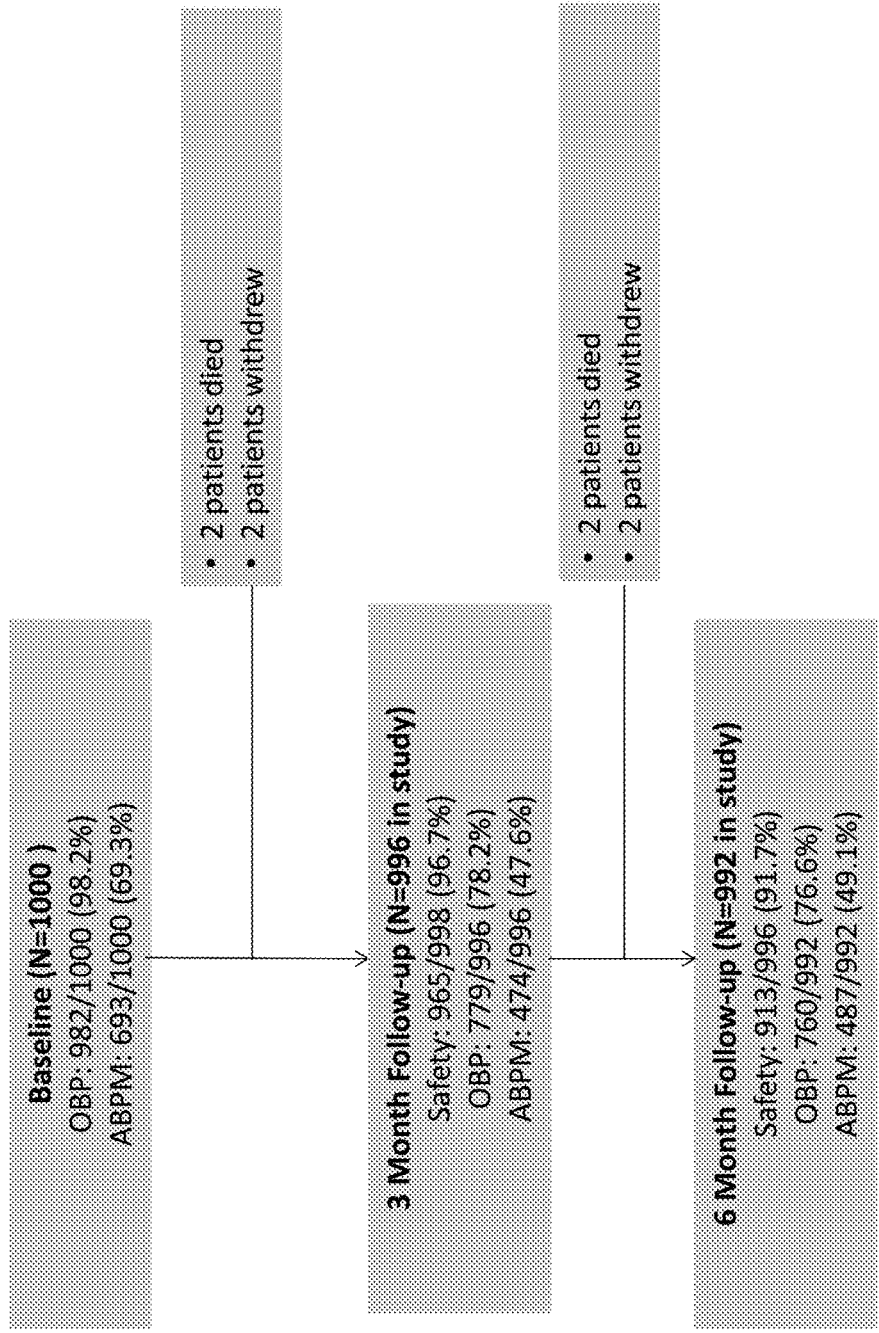

Table 16 and FIGS. 21A-21C summarize baseline characteristics of all enrolled patients, FIG. 21D summarizes corresponding procedural data, and FIG. 21E summarizes post-treatment safety data. Table 16, for example provides baseline characteristics for all patients stratified into subgroups according to their baseline office SBP. Overall mean age was approximately 61 years; 61% were males. A small proportion of patients had a baseline office SBP <140 mm Hg (12·4%) while 58.8% of patients had a SBP ≥160 mm Hg (Table 16). Of the 122 patients with a baseline office SBP<140 mm Hg there were 82 patients with masked hypertension (elevated ABP), 38 patients had a documented history of hypertension and at least one other comorbidity associated with sympathetic overdrive, and 4 patients who did not have hypertension had heart failure with an ejection fraction <35%.

Patients in the study had a high number of comorbidities; approximately 30% of patients had one, two or three comorbidities, and the comorbidities were similarly distributed over the different levels of baseline blood pressure. For example, 41.9% had diabetes, 23.4% had renal impairment (eGFR <60 ml/min/1·73 $m^2$), 4·2% had obstructive sleep apnea, 50·5% had a history of cardiac disease and 9·2% had diagnosed heart failure. Patients were prescribed intensive treatment with multiple antihypertensive medications (4·5±1·3) including diuretics, angiotensin converting-enzyme inhibitors or angiotensin receptor blockers, beta-blockers and calcium channel blockers. Aldosterone receptor antagonists were prescribed in 21% (Table 16). The distribution of most comorbidities was similar across the subgroups except for a higher rate of renal impairment in the <140 mm Hg group (Table 16).

TABLE 16

Baseline characteristics for all patients and according to baseline office systolic blood pressure

|  | All patients n = 1000 | <140 mm Hg n = 122 | 140-159 mm Hg n = 283 | ≥160 mm Hg n = 577 | P value* |
|---|---|---|---|---|---|
| Gender, (% male) | 61.2% | 54.9% | 61.5% | 62.7% | 0.27 |
| Age (years) | 60.7 (12.0) | 61.3 (10.8) | 60.9 (12.5) | 60.4 (12.1) | 0.72 |
| BMI kg/$m^2$ | 30.5 (5.5) | 30.6 (5.9) | 30.4 (4.9) | 30.5 (5.8) | 0.92 |
| Current smoking | 10.0% | 10.7% | 8.9% | 10.3% |  |
| History of cardiac disease | 50.5% (499/989) | 56.7% (68/120) | 52.3% (147/281) | 48.5% (277/571) | 0.21 |
| Hypertension | 99.4% (987/993) | 95.9% (116/121) | 99.6% (280/281) | 100% (574/574) | <0.0001 |
| Sleep apnea (AHI ≥ 5) | 4.2% (39/934) | 4.6% (5/109) | 3.8% (10/264) | 4.4% (24/545) | 0.90 |
| Diabetes | 41.9% (416/993) | 33.1% (40/121) | 45.9% (129/281) | 41.5% (238/574) | 0.06 |
| Type 1 | 3.2% (32/993) | 3.3% (4/121) | 5.0% (14/281) | 2.3% (13/574) | 0.10 |

TABLE 16-continued

Baseline characteristics for all patients and according to baseline office systolic blood pressure

| | All patients<br>n = 1000 | <140 mm Hg<br>n = 122 | 140-159 mm Hg<br>n = 283 | ≥160 mm Hg<br>n = 577 | P value* |
|---|---|---|---|---|---|
| Type 2 | 38.5%<br>(382/993) | 29.8%<br>(36/121) | 40.9%<br>(115/281) | 39.0%<br>(224/574) | 0.10 |
| Renal impairment<br>(eGFR <60<br>ml/min/1.73 m²) | 23.4%<br>(232/993) | 33.1%<br>(40/121) | 21.4%<br>(60/281) | 22.7%<br>(130/574) | <0.05 |
| Atrial fibrillation | 12.7%<br>(126/990) | 19.0%<br>(23/121) | 11.4%<br>(32/282) | 12.1%<br>(69/570) | 0.08 |
| Ventricular<br>tachycardia | 0.6%<br>(6/987) | 0.8%<br>(1/120) | 0.4%<br>(1/281) | 0.5%<br>(3/569) | 0.83 |
| Heart failure | 9.2%<br>(91/989) | 12.5%<br>(15/120) | 10.3%<br>(29/281) | 7.9%<br>(45/571) | 0.20 |
| Left ventricular<br>hypertrophy | 15.7%<br>(155/989) | 20.8%<br>(25/120) | 16.7%<br>(47/281) | 14.4%<br>(82/571) | 0.19 |
| 1 co-morbidity | 39.7%<br>(395/995) | 39.7%<br>(48/121) | 36.2%<br>(102/282) | 41.4%<br>(238/575) | 0.34 |
| 2 co-morbidities | 35.5%<br>(353/995) | 31.4%<br>(38/121) | 39.7%<br>(112/282) | 34.6%<br>(199/575) | 0.20 |
| 3+ co-morbidities | 24.6%<br>(245/995) | 28.9%<br>(35/121) | 23.8%<br>(67/282) | 19.7%<br>(113/575) | 0.47 |
| Number of renal<br>arteries | 2.2 (SD 0.5) | 2.2 (SD 0.6) | 2.1 (SD 04) | 2.2 (SD 0.6) | 0.62 |
| Renal artery length,<br>mm | 41.5 (SD 13.1) | 39.6 (SD 9.5) | 42.8 (SD 14.6) | 41.3 (SD 13.0) | 0.34 |
| Right renal artery<br>diameter, mm | 5.7 (SD 1.2) | 5.3 (SD 1.1) | 5.8 (SD 1.2) | 5.7 (SD 1.2) | <0.05 |
| Left renal artery<br>diameter, mm | 5.7 (SD 1.2) | 5.4 (SD 1.2) | 5.7 (SD 1.3) | 5.7 (SD 1.1) | 0.20 |
| Total # ablations | 13.5 (SD 4.1) | 13.8 (SD 3.5) | 13.2 (SD 3.8) | 13.6 (SD 4.4) | 0.28 |
| Total # 120 sec<br>ablations | 11.3 (SD 3.4) | 11.7 (SD 3.0) | 11.1 (SD 2.9) | 11.3 (SD 3.7) | 0.17 |
| Heart rate | 69.3 (SD 12.8) | 66.9 (SD 12.1) | 69.2 (SD 12.8) | 70.0 (SD 12.9) | <0.05 |
| Antihypertensive<br>medication classes | 4.5 (SD 1.3) | 4.6 (SD 1.4) | 4.5 (SD 1.3) | 4.40 (SD 1.34) | 0.13 |
| Medication use | | | | | |
| Beta-blockers | 78.9% | 78.3% | 78.9% | 79.2% | 0.98 |
| ACE inhibitors | 33.8% | 43.3% | 31.8% | 33.0% | 0.06 |
| ARB | 67.3% | 56.7% | 69.6% | 68.4% | <0.05 |
| CCB | 76.3% | 75.0% | 78.2% | 75.5% | 0.64 |
| Diuretic | 78.2% | 77.5% | 82.9% | 76.0% | 0.08 |
| Aldosterone<br>antagonists | 21.1% | 30.0% | 22.5% | 18.1% | <0.05 |
| Spironolactone | 18.6% | 29.2% | 21.1% | 14.9% | <0.001 |
| Alpha adrenergic<br>blocker | 35.2% | 34.2% | 34.3% | 35.7% | 0.90 |
| Direct-acting<br>vasodilator | 15.1% | 19.2% | 13.2% | 14.9% | 0.31 |
| Centrally acting<br>sympatholytics | 33.2% | 39.2% | 33.9% | 31.6% | 0.27 |
| Direct renin inhibitor | 7.4% | 6.7% | 7.5% | 7.6% | 0.93 |

Values are % (n/N) or mean (SD).
*P value for comparison across the 3 subgroups of patients shown. There were 18 patients without baseline blood pressure recorded who are not included in the subgroups.

Figure 22A:
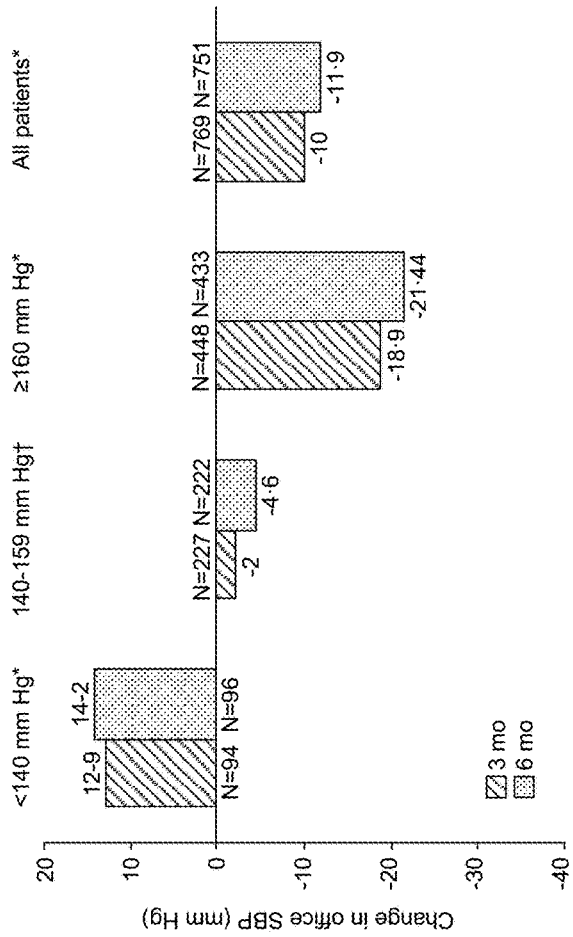
Figure 22B:
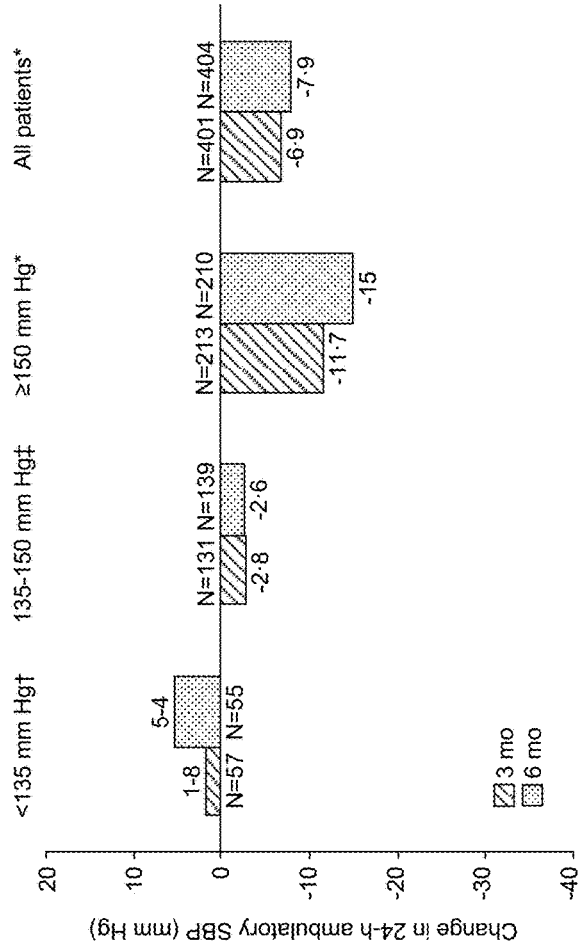

FIGS. 22A and 22B show the effect of renal denervation on office and ambulatory blood pressure at 6 months. In particular, FIG. 22A shows the change in office SBP according to baseline office SBP in patients at 6 months post-RDN, and FIG. 22B shows the change in ambulatory SBP according to baseline ambulatory SBP in patients at 6 months post-RDN. Referring first to FIG. 22A, baseline office SBP was 164.5 (SD 23.6) mm Hg (n=982) and baseline 24-hour ambulatory SBP was 153.9 (SD 18.1) mm Hg (n=693). From baseline, the office SBP was reduced by 10.0 (SD 24.6) mm Hg and 11.9 (SD 24.5) mm Hg at 3 and 6 months, respectively. In 740 patients evaluated at 1 year post-RDN, the office systolic BP was reduced by 13.0 (SD 26.3; p<0.001) mm Hg (not shown). Among 231 patients with baseline renal dysfunction, the office SBP was reduced by 10.6 (SD 26.8; p<0.001) mm Hg at 1 year post RDN (not shown). When patients were stratified according to baseline SBP, a greater reduction of office SBP was observed in those patients with a higher baseline SBP. For example, in patients with more severe hypertension (e.g., baseline office SBP ≥160 mm Hg with an ambulatory 24-hour SBP ≥135 mm Hg and while taking at least 3 antihypertensive medications) the office SBP was reduced by 21.5 (SD 25.6; p<0.001) mm Hg at 12 months post-RDN.

Referring next to FIG. 22B, the ABP reduction was 6.9 (SD 15.2) mm Hg and 7.9 (SD 17.7) mm Hg at 3, and 6 months, respectively, in the overall group. In 390 patients evaluated at 1 year post-RDN, the 24-hour ambulatory SBP was reduced by 8.3 (SD 17.8; p<0.001) mm Hg (not shown). Among 99 patients with baseline renal dysfunction, the ambulatory 24-hour SBP was reduced by 9.7 (SD 20.1; p<0.001) mm Hg at 1 year post RDN (not shown). When analyzed according to baseline 24-hour ambulatory SBP values, there was again an increasing response related to the baseline SBP, with a drop of 15·0 (SD 17·9) mm Hg at 6 months in patients with a baseline 24-hour ambulatory SBP ≥150 mm Hg. At 1 year, patients with more severe hypertension (e.g., baseline office SBP ≥160 mm Hg with an ambulatory 24-hour SBP ≥135 mm Hg and while taking at least 3 antihypertensive medications) demonstrated a 24-hr SBP reduction of 11·4 (SD 17·9; p<0.001) mm Hg.

As set forth in Table 17 below, office and ambulatory BP values for all patients and the subgroups with baseline office SBP above 140 mm Hg uniformly demonstrated a drop in systolic and diastolic BP measurements. The patients in the SBP<140 mm Hg subgroup had a 6-month increase from baseline in office BP but a decrease in ABP.

TABLE 17

Office and ambulatory blood pressure according to baseline systolic blood pressure

|  | All patients | Office SBP <140 mm Hg | Office SBP 140-159 mm Hg | Office SBP ≥160 mm Hg |
|---|---|---|---|---|
| Baseline office BP | n = 982 | n = 122 | n = 283 | n = 577 |
| SBP | 164.5 (SD 23.6) | 127.4 (SD 10.4) | 150.3 (SD 5.7) | 179.3 (SD 17.3) |
| DBP | 89.2 (SD 16.3) | 74.3 (SD 10.6) | 83.6 (SD 12.5) | 95.1 (SD 16.0) |
| 6 Month office BP | n = 760 | n = 96 | n = 222 | n = 433 |
| SBP | 151.4 (SD 21.6) | 141.4 (SD 19.4) | 145.6 (SD 18.4) | 156.6 (SD 22.2) |
| DBP | 84.6 (SD 14.6) | 79.5 (SD 11.8) | 81.6 (SD 14.4) | 87.5 (SD 14.8) |
|  | All patients | Ambulatory SBP <135 mm Hg | Ambulatory SBP 135-149 mm Hg | Ambulatory SBP ≥150 mm Hg |
| Baseline ABP | n = 693 | n = 89 | n = 216 | n = 388 |
| SBP | 153.9 (SD 18.1) | 128.0 (SD 4.7) | 142.6 (SD 4.0) | 166.2 (SD 14.0) |
| DBP | 86.1 (SD 14.1) | 72.9 (SD 9.4) | 81.2 (SD 10.0) | 91.9 (SD 13.9) |
| 6 Month ABP | n = 487 | n = 55 | n = 139 | n = 210 |
| SBP | 143.6 (SD 16.9) | 132.6 (SD 12.3) | 140.4 (SD 13.5) | 149.4 (SD 18.3) |
| DBP | 81.3 (SD 12.8) | 75.3 (SD 10.5) | 81.0 (SD 12.2) | 83.4 (SD 13.7) |

Referring next to Table 18 below, according to baseline ABP and office BP, some patients were stratified as pseudo-resistant (e.g. white-coat) hypertension (i.e., high office BP and normal ABP, n=30), masked hypertension (i.e., high ABP and normal office BP, n=82), and true resistant hypertension (i.e., high office BP and high ABP, n=569). Ambulatory SBP was significantly reduced in patients with masked hypertension, while those with pseudo-hypertension showed an increased ABP following renal denervation. Patients with true hypertension exhibited a significant reduction in both office BP and ABP measurements.

TABLE 18

Office and ambulatory blood pressure according to baseline systolic blood pressure

|  | True resistant hypertension (n = 569) | p-value | Pseudo-resistant hypertension (n = 30) | p-value | Masked hypertension (n = 101) | p-value |
|---|---|---|---|---|---|---|
| | | | Baseline SBP | | | |
| office SBP | 170.1 (SD 20.3) | | 156.3 (SD 12.6) | | 128.6 (SD 8.8) | |
| 24 h ABP SBP | 156.9 (SD 17.3) | | 125.6 (SD 3.3) | | 149.5 (SD 13.3) | |
| daytime ABP SBP | 160.0 (SD 17.7) | | 127.7 (SD 4.5) | | 151.5 (SD 13.7) | |
| | | | 3 months change | | | |
| office SBP | −10.8 (SD 23.2) | <0.0001 | −13.3 (SD 21.5) | 0.010 | 16.7 (SD 19.1) | <0.0001 |
| 24 h ABP SBP | −7.5 (SD 15.1) | <0.0001 | 3.1 (SD 10.3) | 0.22 | −8.6 (SD 17.5) | <0.01 |
| daytime ABP SBP | −8.0 (SD 16.3) | <0.0001 | 1.8 (SD 10.5) | 0.48 | −9.0 (SD 18.8) | <0.01 |
| | | | 6 month change | | | |
| office SBP | −14.6 (SD 23.0) | <0.0001 | −9.0 (SD 22.4) | 0.09 | 15.1 (SD 19.5) | <0.0001 |
| 24 h ABP SBP | −8.9 (SD 17.4) | <0.0001 | 5.5 (SD 13.7) | 0.10 | −9.3 (SD 18.5) | <0.001 |
| daytime ABP SBP | −9.6 (SD 17.8) | <0.0001 | 5.2 (SD 13.4) | 0.10 | −9.2 (SD 18.3) | <0.001 |
| | | | Baseline DBP | | | |
| office DBP | 91.2 (SD 16.1) | | 82.7 (SD 11.3) | | 74.4 (SD 9.8) | |
| 24 h ABP DBP | 87.6 (SD 14.0) | | 69.1 (SD 11.2) | | 84.6 (SD 11.6) | |
| daytime ABP DBP | 89.9 (SD 14.4) | | 71.5 (SD 11.0) | | 86.7 (SD 11.6) | |

TABLE 18-continued

Office and ambulatory blood pressure according to baseline systolic blood pressure

|  | True resistant hypertension (n = 569) | p-value | Pseudo-resistant hypertension (n = 30) | p-value | Masked hypertension (n = 101) | p-value |
|---|---|---|---|---|---|---|
| | | | 3 months change | | | |
| office SBP | −4.1 (SD 13.8) | <0.0001 | −2.4 (SD 16.4) | 0.51 | 6.6 (SD 12.1) | <0.0001 |
| 24 h ABP DBP | −3.8 (SD 9.4) | <0.0001 | 2.1 (SD 8.8) | 0.33 | −4.9 (SD 11.2) | 0.01 |
| daytime ABP DBP | −3.8 (SD 10.2) | <0.0001 | 1.7 (SD 8.6) | 0.42 | −5.5 (SD 11.5) | <0.01 |
| | | | 6 month change | | | |
| office DBP | −5.0 (SD 13.3) | <0.0001 | −6.1 (SD 14.6) | 0.08 | 4.5 (SD 11.3) | <0.01 |
| 24 h ABP DBP | −4.6 (SD 10.6) | <0.0001 | 2.8 (SD 9.4) | 0.21 | −4.7 (SD 11.3) | <0.01 |
| daytime ABP DBP | −4.9 (SD 10.1) | <0.0001 | 4.7 (SD 12.5) | 0.11 | −4.3 (SD 10.9) | <0.01 |

Figure 23:
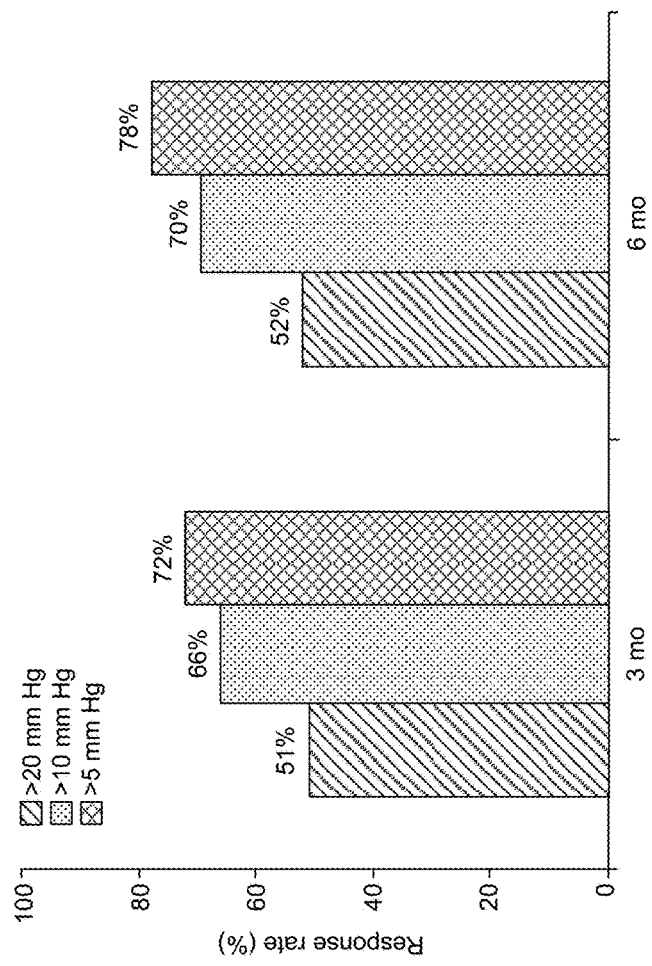
Figure 24:
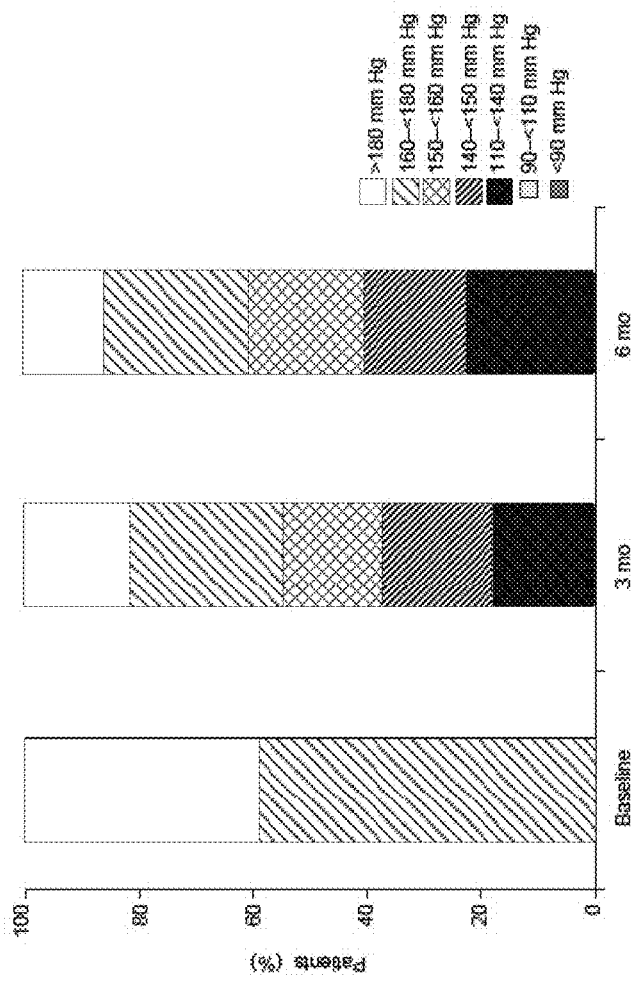

FIG. 23 depicts patient response rates based on reductions in office SBP by 5, 10, or 20 mm Hg for patients with a baseline SBP ≥160 mm Hg. At 6 months, for example, response rates ranged from 52% with a >20 mm Hg reduction to 78% with a >5 mm Hg reduction in SBP. As shown in FIG. 24, the proportion of patients with a baseline SBP ≥160 mm Hg who were controlled (SBP<140 mm Hg) 6 months after RDN was 22.4%. One patient in this group had a SBP reduction to <110 mm Hg at 6 months; however, no events were reported in association with this measurement.

The inclusion criteria were different in the present study than previous Symplicity trials (i.e., Symplicity HTN-1 and Symplicity HTN-2). Most importantly, office SBP at baseline was lower in the present example (164 mm Hg) compared with the Symplicity HTN-1 (175 mm Hg) and Symplicity HTN-2 (178 mm Hg) trials. As a result, a corresponding lower drop in blood pressure was observed. In particular, blood pressure reduction was 22 mm Hg in Symplicity HTN-1 and 32 mm Hg in Symplicity HTN-2 compared with approximately 12 mm Hg in the patients of the present study at 6 months.

Patients received an average of 4.5 (SD 1.3) blood pressure medication classes at baseline. The number of blood pressure medications used was similarly distributed across the different blood pressure groups with the exception of angiotensin receptor blockers and aldosterone antagonists (Table 16). As outlined below in Table 19, similar results were obtained for pharmacologic treatment according to comorbidities: sleep apnea, diabetes, chronic kidney disease, atrial fibrillation, and heart failure.

TABLE 19

Office and ambulatory blood pressure change at 6 months with baseline antihypertensive medication use by co-morbidity

|  | Sleep apnea | Diabetes | Chronic kidney disease | Atrial fibrillation | Heart Failure |
|---|---|---|---|---|---|
| Change from baseline in office SBP at 6 months | −10.4 (SD 29.0) | −12.9 (SD 23.7) | −11.6 (SD 25.8) | −10.1 (SD 25.6) | −13.7 (SD 25.4) |
| Change from baseline in ABP at 6 months | −5.8 (SD 15.2) | −9.5 (SD 17.6) | −7.1 (SD 20.5) | −10.9 (SD 17.0) | −6.7 (SD 15.8) |
| Antihypertensive medication classes | 4.9 (SD 1.7) | 4.6 (SD 1.3) | 4.8 (SD 1.2) | 4.4 (SD 1.2) | 4.5 (SD 1.3) |
| Drug classes: | | | | | |
| Beta-blockers | 71.1% | 82.0% | 82.2% | 75.4% | 88.8% |
| ACE inhibitors | 31.6% | 34.7% | 42.2% | 38.9% | 38.2% |
| ARB | 68.4% | 69.4% | 60.9% | 61.9% | 60.7% |
| CCB | 81.6% | 79.4% | 80.4% | 68.3% | 71.9% |
| Diuretic | 79.0% | 80.3% | 81.7% | 80.2% | 76.4% |
| Aldosterone antagonists | 31.6% | 22.3% | 23.0% | 21.4% | 31.5% |
| Spironolactone | 29.0% | 19.9% | 21.3% | 18.3% | 28.1% |
| Alpha adrenergic blocker | 36.8% | 37.4% | 44.8% | 44.4% | 24.7% |
| Direct-acting vasodilator | 23.7% | 17.7% | 20.0% | 14.3% | 14.6% |
| Centrally-acting sympatholytics | 47.4% | 34.0% | 42.6% | 34.1% | 33.7% |
| Direct renin inhibitor | 18.4% | 4.6% | 6.1% | 3.2% | 4.5% |

Following RDN there was a statistically significant reduction in the number of antihypertensive medications (4.3 (SD 1.4), p<0.0001). Referring to Table 20 below, for example, changes in antihypertensive therapy were primarily related to reduction of a-adrenergic blocker, centrally acting sympatholytic, beta blocker, angiotensin-converting-enzyme inhibitor and direct renin inhibitor use. The proportion of patients who decreased their drug class use was greater than the proportion of patients with increased drug class use at the 6 month follow-up period.

TABLE 20

Medication use over time

| | Baseline | 3 months | 6 months | P-value |
|---|---|---|---|---|
| Antihypertensive medication classes | 4.5 (SD 1.3) | 4.4 (SD 1.4) | 4.3 (SD 1.4) | <0.0001 |
| Drug classes: | n = 978 | n = 988 | n = 992 | |
| Beta-blockers | 78.9% (772) | 76.6% (757) | 76.5% (759) | <0.01 |
| ACE inhibitors | 33.8% (331) | 31.9% (315) | 31.4% (311) | <0.001 |
| ARB | 67.3% (658) | 67.2% (664) | 66.8% (663) | 0.58 |
| CCB | 76.3% (746) | 76.1% (752) | 75.7% (751) | 0.87 |
| Diuretic | 78.2% (765) | 77.2% (763) | 76.5% (759) | 0.23 |
| Aldosterone antagonists | 21.1% (206) | 22.0% (217) | 22.6% (224) | 0.04 |
| Spironolactone | 18.6% (182) | 19.2% (190) | 19.8% (196) | 0.13 |
| Alpha adrenergic blocker | 35.2% (344) | 32.6% (322) | 31.3% (310) | <0.0001 |
| Direct-acting vasodilator | 15.1% (148) | 14.4% (142) | 14.2% (141) | 0.39 |
| Centrally-acting sympatholytics | 33.2% (325) | 31.5% (311) | 31.0% (307) | <0.01 |
| Direct renin inhibitor | 7.4% (72) | 7.0% (69) | 6.0% (59) | <0.01 |

Referring next to Table 21, the RDN procedure was associated with minimal complications (1 month and 6 month post RDN data shown). Periprocedurally, for example, there was 1 (0.09%) renal artery re-intervention after a dissection, 3 pseudoaneurysms (0.34%) and 1 hematoma (0.09%). Following the procedure through 6 months, there were 4 deaths (2 cardiovascular), and 9 cases of hospitalization for hypertensive emergency (Table 18). All events to 6 months occurred at a frequency of <1%.

TABLE 21

Safety at 1 and 6 months

| | 1 month n = 967 | 6 month n = 913 |
|---|---|---|
| Major Adverse Events* | 0.83% (8) | |
| Cardiovascular events | | |
| Cardiovascular death | 0.00% (0) | 0.22% (2) |
| Stroke | 0.21% (2) | 0.88% (8) |
| Hospitalization for new onset heart failure | 0.31% (3) | 0.66% (6) |
| Hospitalization for atrial fibrillation | 0.10% (1) | 0.88% (8) |
| Hospitalization for hypertensive crisis/hypertensive emergency | 0.21% (2) | 0.99% (9) |
| Spontaneous MI | 0.00% (0) | 0.55% (5) |
| Renal events | | |
| New onset end stage renal disease | 0.10% (1) | 0.22% (2) |
| Serum creatinine elevation > 50% | 0.10% (1) | 0.22% (2) |
| New renal artery stenosis > 70% | | 0.00% (0) |
| Post-procedural events | | |
| Non-cardiovascular death | 0.00% (0) | 0.22% (2) |
| Renal artery re-intervention | 0.10% (1) | 0.22% (2) |
| Vascular complication | 0.41% (4) | 0.44% (4) |

*Based on 1 month rates of death new onset renal disease, renal artery re-intervention, vascular complications, hospitalization for hypertensive crisis/emergency and new renal artery stenosis at 6 months Renal function was also assessed throughout the study. For example, from baseline to 3 and 6 months of follow-up, there was no change in eGFR. Two patients developed end-stage renal disease by 6 months (one occurred following a suicide attempt and the other patient was treated with RDN despite a baseline eGFR of 18.8 ml/min/1.73 m2) and 3 patients developed end-stage renal disease by 12 months following the procedure. However, mean eGFR of the total population decreased from 76.4 (SD 25.1) at baseline to 71.9 (SD 24.6) ml/min/1.73 m2 at 1 year post procedure. A subgroup of patients with chronic kidney disease (n=149) at baseline had a mean eGFR of 48.7 (SD 16.5) ml/min/1.73 m2 which declined slightly at 1 year to 45.7 (SD 17.4) ml/min/1.73 m2 in the group. At 6 months, two patients had a more than 50% elevation of serum creatinine from baseline; one with new end stage renal disease already described and the other in an elderly patient following hospitalization for hypertensive crisis, syncope and end organ damage who died shortly thereafter from her underlying disease. At 12 months post RDN, new renal artery stenosis >70% occurred in 2 patients. Otherwise, there was no evidence of renal injury related to the denervation procedure. At 1 year post procedure, the composite safety endpoint was 3.9% (34/862), comprising 0.8% cardiovascular death, 1.6% hospitalization for hypertensive crisis, 0.2% new renal artery stenosis, 0.4% renal artery re-intervention, and 0.4% new onset end stage renal disease.

VI. FURTHER EXAMPLES

Group A

1. In a female patient, a method for treating hypertension comprising:
   intravascularly placing an energy delivery element in a renal artery of the patient; and
   modulating a renal nerve along the renal artery by delivering energy from the energy delivery element to a wall of the renal artery,
   wherein the patient achieves a decrease in blood pressure of at least 6 mm Hg more than a blinded control group.

2. In a patient on an aldosterone antagonist, a method for treating hypertension comprising:
   intravascularly placing an energy delivery element in a renal artery of the patient; and
   modulating a real nerve along the renal artery by delivering energy from the energy delivery element to a wall of the renal artery,
   wherein the patient achieves a decrease in blood pressure of at least 7 mm Hg more than a blinded control group.

3. In a patient having an estimated glomerular filtration rate greater than 60, a method for treating hypertension comprising:
   intravascularly placing an energy delivery element in a renal artery of the patient; and
   modulating a real nerve along the renal artery by delivering energy from the energy delivery element to a wall of the renal artery,
   wherein the patient achieves a decrease in blood pressure of at least 5 mm Hg more than a blinded control group.

4. In a patient under 65 years of age, a method for treating hypertension comprising: intravascularly placing an energy delivery element in a renal artery of the patient; and
   modulating a real nerve along the renal artery by delivering energy from the energy delivery element to a wall of the renal artery,
   wherein the patient achieves a decrease in blood pressure of at least 5 mm Hg more than a blinded control group.

5. The method of any of examples 1-4 wherein the patient has a baseline blood pressure before treatment of at least approximately 160 mm Hg.

6. The method of any of examples 1-5 wherein the energy delivery element comprises a basket and a plurality of electrodes carried by the basket, wherein the electrodes are circumferentially spaced apart from each other such that each electrode is 90° apart from a neighboring electrode, and ablating the plurality of locations comprises positioning the basket at a distal portion of the renal artery, delivering electrical energy through each of the electrodes at the distal portion of the renal artery, moving the basket proximally within the renal artery to a more proximal portion of the renal artery, rotating the basket approximately 45°, and delivering electrical energy to each of the electrodes at the more proximal portion of the renal artery.

7. The method of any of examples 1-5 wherein the energy delivery element comprises a balloon and a plurality of bipolar electrodes carried by the balloon, and ablating the plurality of treatment locations comprises positioning the balloon at a distal portion of the renal artery, delivering electrical energy through each of the electrodes at the distal portion of the renal artery, moving the balloon proximally within the renal artery to a more proximal portion of the renal artery, and delivering energy to each of the electrodes at the more proximal portion of the renal artery.

8. The method of any of examples 1-5 wherein the energy delivery element comprises a single-electrode device, and ablating the plurality of locations comprises positioning the single electrode at a treatment site, delivering energy to the treatment site via the single electrode, moving the single electrode proximally to a subsequent treatment site and rotating the single electrode approximately 45°, delivering energy to the subsequent treatment site via the single electrode, and repeating the moving and delivering energy acts at additional treatment sites.

9. The method of any of examples 1-5 wherein the energy delivery element comprises an irrigated electrode.

10. The method of any of examples 1-9 wherein the renal artery has a diameter of not less than 4 mm.

11. The method of any of examples 1-10 wherein the patient is on a maximum tolerable dosage of one or more antihypertensive medications.

12. The method of any of examples 1-11, further comprising receiving a generator feedback message regarding ablation at a treatment location, and repeating ablation at the treatment location associated with the feedback message.

13. The method of any of examples 1-12 wherein the number of treatment locations is not less than 8.

14. The method of any of examples 1-4 wherein:
the energy delivery device has a plurality of electrodes arranged along an elongated member, and the elongated member is configured to be contained in a catheter in a low-profile configuration and to have a helical shape in a deployed configuration;
intravascularly placing the energy delivery element in the renal artery comprises moving the elongated member into the deployed configuration such that the electrodes contact a plurality of treatment locations arranged in a helical pattern; and
ablating the plurality of treatment locations comprises delivering electrical energy via the plurality of electrodes.

15. The method of example 14 wherein the patient is on a maximum tolerable dosage of one or more antihypertensive medications.

16. The method of any of examples 14-15, further comprising receiving a generator feedback message regarding ablation at a treatment location, and repeating ablation at the treatment location associated with the feedback message.

17. The method of any of examples 14-16 wherein the number of treatment locations is not less than 8.

18. A method of treating a female patient having hypertension, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly,
wherein the patient achieves a reduction in blood pressure of at least 6 mm Hg more than a blinded control group.

19. A method of treating a patient having hypertension on an aldosterone antagonist, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly,
wherein the patient achieves a reduction in blood pressure of at least 7 mm Hg more than a blinded control group.

20. A method of treating a patient having hypertension with an estimated glomerular filtration rate greater that about 60, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly,
wherein the patient achieves a reduction in blood pressure of at least 5 mm Hg more than a blinded control group.

21. A method of treating a patient having hypertension not more than 65 years of age, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly,
wherein the patient achieves a reduction in blood pressure of at least 5 mm Hg more than a blinded control group.

22. The method of any of examples 18-21 wherein the patient has a baseline blood pressure before treatment of at least 160 mm Hg.

23. The method of any of examples 18-22 wherein the neuromodulation assembly comprises an energy delivery element, and partially inhibiting sympathetic neural activity in the neural fibers comprises delivering energy from the energy delivery element to a wall of the renal artery.

24. The method of example 23 wherein the energy delivery element comprises a basket and a plurality of electrodes carried by the basket, wherein the electrodes are circumferentially spaced apart from each other such that each electrode is 90° apart from a neighboring electrode, and ablating the plurality of locations comprises positioning the basket at a distal portion of the renal artery, delivering electrical energy through each of the electrodes at the distal portion of the renal artery, moving the basket proximally within the renal artery to a more proximal portion of the renal artery, rotating the basket approximately 45°, and delivering electrical energy to each of the electrodes at the more proximal portion of the renal artery.

25. The method of example 23 wherein the energy delivery element comprises a balloon and a plurality of bipolar electrodes carried by the balloon, and ablating the plurality of treatment locations comprises positioning the balloon at a distal portion of the renal artery, delivering electrical energy through each of the electrodes at the distal portion of the renal artery, moving the balloon proximally within the renal artery to a more proximal portion of the renal artery, and delivering energy to each of the electrodes at the more proximal portion of the renal artery.

26. The method of example 23 wherein the energy delivery element comprises a single-electrode device, and ablating the plurality of locations comprises positioning the single electrode at a treatment site, delivering energy to the treatment site via the single electrode, moving the single-electrode proximally to a subsequent treatment site and rotating the single electrode approximately 45°, delivering energy to the subsequent treatment site via the single electrode, and repeating the moving and delivering energy acts at additional treatment sites.

27. The method of example 23 wherein the energy delivery element comprises an irrigated electrode.

28. The method of any of examples 18-27 wherein the renal artery has a diameter of not less than 4 mm.

29. The method of any of examples 18-28 wherein the patient is on a maximum tolerable dosage of one or more antihypertensive medications.

30. The method of any of examples 18-29, further comprising receiving a generator feedback message regarding ablation at a treatment location, and repeating ablation at the treatment location associated with the feedback message.

31. The method of any of examples 18-30 wherein the number of treatment locations is not less than 8.

32. The method of example 23 wherein:
the energy delivery device has a plurality of electrodes arranged along an elongated member, and the elongated member is configured to be contained in a catheter in a low-profile configuration and to have a helical shape in a deployed configuration;
intravascularly placing the energy delivery element in the renal artery comprises moving the elongated member into the deployed configuration such that the electrodes contact a plurality of treatment locations arranged in a helical pattern; and
ablating the plurality of treatment locations comprises delivering electrical energy via the plurality of electrodes.

33. The method of example 32 wherein the patient is on a maximum tolerable dosage of at least one antihypertensive medication.

34. The method of any of examples 32-33, further comprising receiving a generator feedback message regarding ablation at a treatment location, and repeating ablation at the treatment location associated with the feedback message.

35. The method of any of examples 32-34 wherein the number of treatment locations is not less than 8.

Group B

1. In a hypertensive patient population, a method of determining a patient subpopulation for treating with renal neuromodulation, the method comprising:
percutaneously introducing a distal portion of a neuromodulation assembly proximate to renal nerves of a plurality of patients diagnosed with hypertension;
partially disrupting function of the renal nerves in each individual patient by applying energy to the renal nerve via the neuromodulation assembly; and
identifying patient cohort criteria from a patient subpopulation having decrease in blood pressure of at least 5 mm Hg more than a blinded control group after partially disrupting the renal nerves.

2. The method of example 1 wherein identifying patient cohort criteria comprises patients not more than 65 years of age.

3. The method of example 1 wherein identifying patient cohort criteria comprises patients on an aldosterone antagonist.

4. The method example 1 wherein identifying patient cohort criteria comprises patients having an estimated glomerular filtration rate of at least 60.

5. The method of example 1 wherein identifying patient cohort criteria comprises female patients.

Group C

1. In a female patient, a method for treating hypertension comprising:
intravascularly placing an energy delivery element in a renal artery of the patient; and
modulating a renal nerve along the renal artery by delivering energy from the energy delivery element to a wall of the renal artery.

2. The method of example 1 wherein the patient achieves a decrease in blood pressure of at least 6 mm Hg more than a blinded control group.

3. In a patient on an aldosterone antagonist, a method for treating hypertension comprising:
intravascularly placing an energy delivery element in a renal artery of the patient; and
modulating a real nerve along the renal artery by delivering energy from the energy delivery element to a wall of the renal artery.

4. The method of example 3 wherein the patient achieves a decrease in blood pressure of at least 7 mm Hg more than a blinded control group.

5. In a patient having an estimated glomerular filtration rate greater than 60, a method for treating hypertension comprising:
intravascularly placing an energy delivery element in a renal artery of the patient; and
modulating a real nerve along the renal artery by delivering energy from the energy delivery element to a wall of the renal artery.

6. The method of example 5 wherein the patient achieves a decrease in blood pressure of at least 5 mm Hg more than a blinded control group.

7. In a patient under 65 years of age, a method for treating hypertension comprising:
intravascularly placing an energy delivery element in a renal artery of the patient; and
modulating a real nerve along the renal artery by delivering energy from the energy delivery element to a wall of the renal artery.

8. The method of example 7 wherein the patient achieves a decrease in blood pressure of at least 5 mm Hg more than a blinded control group.

9. The method of any of examples 1-8 wherein the patient has a baseline blood pressure before treatment of at least approximately 160 mm Hg.

10. The method of any of examples 1-9 wherein the energy delivery element comprises a basket and a plurality of electrodes carried by the basket, wherein the electrodes are circumferentially spaced apart from each other such that each electrode is 90° apart from a neighboring electrode, and ablating the plurality of locations comprises positioning the basket at a distal portion of the renal artery, delivering electrical energy through each of the electrodes at the distal portion of the renal artery, moving the basket proximally within the renal artery to a more proximal portion of the renal artery, rotating the basket approximately 45°, and delivering electrical energy to each of the electrodes at the more proximal portion of the renal artery.

11. The method of any of examples 1-9 wherein the energy delivery element comprises a balloon and a plurality of bipolar electrodes carried by the balloon, and ablating the plurality of treatment locations comprises positioning the balloon at a distal portion of the renal artery, delivering electrical energy through each of the electrodes at the distal portion of the renal artery, moving the balloon proximally within the renal artery to a more proximal portion of the renal artery, and delivering energy to each of the electrodes at the more proximal portion of the renal artery.

12. The method of any of examples 1-9 wherein the energy delivery element comprises a single-electrode device, and ablating the plurality of locations comprises positioning the single electrode at a treatment site, delivering energy to the treatment site via the single electrode, moving the single electrode proximally to a subsequent treatment site and rotating the single electrode approximately 45°, delivering energy to the subsequent treatment site via the single electrode, and repeating the moving and delivering energy acts at additional treatment sites.

13. The method of any of examples 1-9 wherein the energy delivery element comprises an irrigated electrode.

14. The method of any of examples 1-13 wherein the renal artery has a diameter of not less than 4 mm.

15. The method of any of examples 1-14 wherein the patient is on a maximum tolerable dosage of one or more antihypertensive medications.

16. The method of any of examples 1-15, further comprising receiving a generator feedback message regarding ablation at a treatment location, and repeating ablation at the treatment location associated with the feedback message.

17. The method of any of examples 1-16 wherein the number of treatment locations is not less than 8.

18. The method of any of examples 1-8 wherein:
the energy delivery device has a plurality of electrodes arranged along an elongated member, and the elongated member is configured to be contained in a catheter in a low-profile configuration and to have a helical shape in a deployed configuration;
intravascularly placing the energy delivery element in the renal artery comprises moving the elongated member into the deployed configuration such that the electrodes contact a plurality of treatment locations arranged in a helical pattern; and
ablating the plurality of treatment locations comprises delivering electrical energy via the plurality of electrodes.

19. The method of example 18 wherein the patient is on a maximum tolerable dosage of one or more antihypertensive medications.

20. The method of any of examples 18-19, further comprising receiving a generator feedback message regarding ablation at a treatment location, and repeating ablation at the treatment location associated with the feedback message.

21. The method of any of examples 18-20 wherein the number of treatment locations is not less than 8.

22. A method of treating a female patient having hypertension, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly.

23. The method of example 22 wherein the patient achieves a reduction in blood pressure of at least 6 mm Hg more than a blinded control group.

24. A method of treating a patient having hypertension on an aldosterone antagonist, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly.

25. The method of claim 24 wherein the patient achieves a reduction in blood pressure of at least 7 mm Hg more than a blinded control group.

26. A method of treating a patient having hypertension with an estimated glomerular filtration rate greater that about 60, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly.

27. The method of example 26 wherein the patient has a reduction in blood pressure of at least 5 mm Hg more than a blinded control group.

28. A method of treating a patient having hypertension not more than 65 years of age, the method comprising:
intravascularly positioning a neuromodulation assembly within a renal blood vessel of the subject and adjacent to neural fibers innervating a kidney of the subject; and
partially inhibiting sympathetic neural activity in the neural fibers of the subject via the neuromodulation assembly.

29. The method of example 28 wherein the patient achieves a reduction in blood pressure of at least 5 mm Hg more than a blinded control group.

30. The method of any of examples 22-29 wherein the patient has a baseline blood pressure before treatment of at least 160 mm Hg.

31. The method of any of examples 22-30 wherein the neuromodulation assembly comprises an energy delivery element, and partially inhibiting sympathetic neural activity in the neural fibers comprises delivering energy from the energy delivery element to a wall of the renal artery.

32. The method of example 31 wherein the energy delivery element comprises a basket and a plurality of electrodes carried by the basket, wherein the electrodes are circumferentially spaced apart from each other such that each electrode is 90° apart from a neighboring electrode, and ablating the plurality of locations comprises positioning the basket at a distal portion of the renal artery, delivering electrical energy through each of the electrodes at the distal portion of the renal artery, moving the basket proximally within the renal artery to a more proximal portion of the renal artery, rotating the basket approximately 45°, and delivering electrical energy to each of the electrodes at the more proximal portion of the renal artery.

33. The method of example 31 wherein the energy delivery element comprises a balloon and a plurality of bipolar electrodes carried by the balloon, and ablating the plurality of treatment locations comprises positioning the balloon at a distal portion of the renal artery, delivering electrical energy through each of the electrodes at the distal portion of the renal artery, moving the balloon proximally within the renal artery to a more proximal portion of the renal artery, and delivering energy to each of the electrodes at the more proximal portion of the renal artery.

34. The method of example 31 wherein the energy delivery element comprises a single-electrode device, and ablating the plurality of locations comprises positioning the single electrode at a treatment site, delivering energy to the treatment site via the single electrode, moving the single electrode proximally to a subsequent treatment site and rotating the single electrode approximately 45°, delivering energy to the subsequent treatment site via the single electrode, and repeating the moving and delivering energy acts at additional treatment sites.

35. The method of example 31 wherein the energy delivery element comprises an irrigated electrode.

36. The method of any of examples 22-35 wherein the renal artery has a diameter of not less than 4 mm.

37. The method of any of examples 22-36 wherein the patient is on a maximum tolerable dosage of one or more antihypertensive medications.

38. The method of any of examples 22-37, further comprising receiving a generator feedback message regarding ablation at a treatment location, and repeating ablation at the treatment location associated with the feedback message.

39. The method of any of examples 22-38 wherein the number of treatment locations is not less than 8.

40. The method of example 31 wherein:
   the energy delivery device has a plurality of electrodes arranged along an elongated member, and the elongated member is configured to be contained in a catheter in a low-profile configuration and to have a helical shape in a deployed configuration;
   intravascularly placing the energy delivery element in the renal artery comprises moving the elongated member into the deployed configuration such that the electrodes contact a plurality of treatment locations arranged in a helical pattern; and
   ablating the plurality of treatment locations comprises delivering electrical energy via the plurality of electrodes.

41. The method of example 40 wherein the patient is on a maximum tolerable dosage of one or more antihypertensive medications.

42. The method of any of examples 40-41, further comprising receiving a generator feedback message regarding ablation at a treatment location, and repeating ablation at the treatment location associated with the feedback message.

43. The method of any of examples 40-42 wherein the number of treatment locations is not less than 8.

Group D

1. A method of treating a human patient with hypertension who is taking a prescribed regimen of antihypertensive medications, the method comprising:
   intravascularly positioning a neuromodulation assembly within a renal blood vessel of the patient and adjacent to neural fibers innervating a kidney of the patient; and
   partially inhibiting sympathetic neural activity in the neural fibers of the patient via the neuromodulation assembly,
   wherein partially inhibiting sympathetic neural activity results in a reduction in blood pressure in the patient not less than a blinded control group.

2. The method of example 1 wherein the reduction in blood pressure in the patient after therapy further results in the patient reducing a dosage of one or more of the prescribed antihypertensive medications while maintaining the reduction in blood pressure.

3. The method of example 1 wherein the reduction in blood pressure in the patient after therapy further results in the patient exchanging one or more of the prescribed antihypertensive medications from the regimen with a different antihypertensive medication while maintaining the reduction in blood pressure.

4. The method of example 1 wherein the reduction in blood pressure in the patient after therapy further results in the patient eliminating one or more of the prescribed antihypertensive medications from the regimen while maintaining the reduction in blood pressure.

5. The method of example 1 wherein the reduction in blood pressure in the patient after therapy further results in the patient eliminating two or more of the prescribed antihypertensive medications from the regimen while maintaining the reduction in blood pressure.

6. The method of any one of examples 1-5 wherein partially inhibiting sympathetic neural activity results in a reduction in blood pressure in the patient of at least 2 mm Hg more than a blinded control group.

7. The method of any one of examples 1-5 wherein partially inhibiting sympathetic neural activity results in a reduction in blood pressure in the patient of at least 5 mm Hg more than a blinded control group.

Group E

1. In an African-American patient having a baseline office blood pressure of at least about 160 mm Hg, a method of treating hypertension comprising:
   providing a vasodilator drug to the patient;
   instructing the patient to take the vasodilator drugs at a maximum tolerated dose such that the vasodilator drugs cause a drop in office blood pressure of not less than about 17 mm Hg.

2. In a hypertensive African-American patient, a method of treating hypertension:
   determining a maximum tolerated dose of a plurality of vasodilator drugs for the patient;
   instructing the patient to take at least three vasodilator drugs at the maximum tolerated dosages; and
   causing a drop in office blood pressure of not less than about 17 mm Hg.

3. The methods of examples 1 and 2, further comprising:
   intravascularly placing an energy delivery element in a renal artery; and
   ablating a plurality of locations in the renal artery, wherein each of the locations are spaced apart from each other by not less than approximately 5 mm and arranged in a helical pattern around the wall of the renal artery at approximately 45° intervals from neighboring treatment locations.

4. The methods of examples 1 and 2, further comprising:
   intravascularly placing an energy delivery element in a renal artery; and
   modulating a renal nerve along the renal artery by delivering energy from the energy delivery element to a wall of the renal artery.

5. The methods of examples 3 and 4 wherein the patient is under 65 years of age.

6. The methods of examples 3-5 wherein the patient is taking an aldosterone antagonist.

7. The methods of examples 3-5 wherein the renal artery has a diameter not less than about 4 mm.

8. In a Non-African-American patient with resistant hypertension having a baseline office blood pressure of at least about 160 mm Hg, a method of treating hypertension, comprising:

intravascularly placing an energy delivery element in a renal artery; and ablating a plurality of treatment locations in the renal artery, wherein the treatment locations are spaced apart from each other by not less than approximately 5 mm and arranged in a helical pattern around a wall of the renal artery at approximately 45° intervals from neighboring treatment locations such that ablating the plurality of treatment location causes a drop in office blood pressure of not less than about 15 mm Hg.

9. In a Non-African American drug-resistant hypertensive patient, a method of treating hypertension comprising:

intravascularly placing an energy delivery element in a renal artery; and modulating a renal nerve along the renal artery by delivering energy from the energy delivery element to a wall of the renal artery, wherein the patient has a decrease in blood pressure of at least about 6 mm Hg more than a blinded control group.

10. The method of example 9 wherein the patient has a baseline blood pressure before treatment of at least about 160 mm Hg.

11. The method of any of examples 8-10 wherein the energy delivery element comprises a basket and a plurality of electrodes carried by the basket, wherein the electrodes are circumferentially spaced apart from each other such that each electrode is 90° apart from a neighboring electrode, and ablating the plurality of locations comprises positioning the basket at a distal portion of the renal artery, delivering electrical energy through each of the electrodes at the distal portion of the renal artery, moving the basket proximally within the renal artery to a more proximal portion of the renal artery, rotating the basket approximately 45°, and delivering electrical energy to each of the electrodes at the more proximal portion of the renal artery.

12. The method of any of examples 8-10 wherein the energy delivery element comprises a balloon and a plurality of bipolar electrodes carried by the balloon, and ablating the plurality of treatment locations comprises positioning the balloon at a distal portion of the renal artery, delivering electrical energy through each of the electrodes at the distal portion of the renal artery, moving the balloon proximally within the renal artery to a more proximal portion of the renal artery, and delivering energy to each of the electrodes at the more proximal portion of the renal artery.

13. The method of any of examples 8-10 wherein the energy delivery element comprises a single-electrode device, and ablating the plurality of locations comprises positioning the single electrode at a treatment site, delivering energy to the treatment site via the single electrode, moving the single electrode proximally to a subsequent treatment site and rotating the single electrode approximately 45°, delivering energy to the subsequent treatment site via the single electrode, and repeating the moving and delivering energy acts at additional treatment sites.

14. The method of any of examples 8-10 wherein the energy delivery element comprises an irrigated electrode.

15. The method of any of examples 8-14 wherein the renal artery has a diameter of not less than about 4 mm.

16. The method of any of examples 8-15 wherein the patient is on a maximum tolerable dosage of one or more antihypertensive drugs.

17. The method of any of examples 8-16, further comprising receiving an error message regarding ablation at a treatment location, and repeating ablation at the treatment location associated with the error message.

18. The method of any of examples 8-17 wherein the number of treatment locations is not less than 8.

19. The method of any of examples 8-9 wherein:

the energy delivery device has a plurality of electrodes arranged along an elongated member, and the elongated member is configured to be contained in a catheter in a low-profile configuration and to have a helical shape in a deployed configuration;

intravascularly placing the energy delivery element in the renal artery comprises moving the elongated member into the deployed configuration such that the electrodes contact a plurality of treatment locations arranged in a helical pattern; and ablating the plurality of treatment locations comprises delivering electrical energy via the plurality of electrodes.

20. The method of example 19 wherein the patient is on a maximum tolerable dosage of one or more antihypertensive medications.

21. The method of any of examples 19-20, further comprising receiving an error message regarding ablation at a treatment location, and repeating ablation at the treatment location associated with the error message.

22. The method of any of examples 19-21 wherein the number of treatment locations is not less than 8.

23. The method of example 1 wherein providing a vasodilator drugs to the patient comprises providing a combination of two or more vasodilator drugs to the patient.

Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for treating hypertension, the method comprising:
    selecting a female human patient having a baseline blood pressure of at least 160 mm Hg;
    intravascularly delivering an energy delivery element to a renal artery of the selected patient; and
    modulating a renal nerve along the renal artery by delivering energy from the energy delivery element to a plurality of treatment locations along a wall of the renal artery,
    wherein the treatment locations are arranged in a helical pattern along the renal artery, and wherein the helical pattern includes at least one treatment location in each of the inferior, anterior, superior and posterior positions around the wall of the renal artery,
    wherein the selected patient achieves a decrease in blood pressure of at least 6 mm Hg more than a resistant hypertensive, female control group patient, and
    wherein the female control group patient having an average baseline blood pressure of at least 160 mm Hg, is younger than 68 years of age, takes three or more anti-hypertensive medications at maximally tolerated doses, and underwent a sham procedure instead of the modulation treatment.

2. The method of claim 1 whereby the selected patient achieves a decrease in office blood pressure of not less than 14 mm Hg.

3. The method of claim 1 wherein the selected patient is on a maximum tolerable dosage of one or more antihypertensive medications.

4. The method of claim 1 wherein the number of treatment locations is at least 8.

5. The method of claim 1 wherein the patient achieves the decrease in office blood pressure by six months after modulation of the renal nerve.

6. A method for treating hypertension, the method comprising:
    selecting a human patient having a baseline blood pressure of at least 160 mm Hg and on an aldosterone antagonist;
    intravascularly positioning an energy delivery element within a renal artery of the selected patient; and
    modulating a renal nerve along the renal artery via energy from the energy delivery element at a plurality of locations along a wall of the renal artery, wherein the selected patient achieves a decrease in blood pressure of at least 7 mm Hg more than a resistant hypertensive control group patient, and
    wherein the control group patient has an average baseline blood pressure of at least 160 mm Hg, is younger than 68 years of age, is on an aldosterone antagonist, and underwent a sham procedure instead of the modulation treatment.

7. The method of claim 6 wherein the selected patient has a decrease in blood pressure of at least 4 mm Hg more than a comparable patient having a baseline office blood pressure of at least 160 mm Hg, and wherein the comparable patient is not taking an aldosterone antagonist, and wherein the comparable patient underwent method steps comprising:
    intravascularly positioning an energy delivery element within a renal artery of the comparable patient; and
    modulating a renal nerve along the renal artery of the comparable patient via energy from the energy delivery element at a plurality of treatment locations along a wall of the renal artery.

8. The method of claim 6 wherein the selected patient achieves a decrease in office blood pressure of not less than 14 mm Hg.

9. The method of claim 6 wherein the selected patient achieves a decrease in office blood pressure of not less than 20 mm Hg.

10. The method of claim 6 wherein the patient achieves the decrease in office blood pressure by six months after modulation of the renal nerve.

11. A method for treating hypertension, the method comprising:
    selecting a human patient under 65 years of age and having a baseline blood pressure of at least 160 mm Hg;
    intravascularly delivering an energy delivery element to a renal artery of the selected patient; and
    modulating a renal nerve along the renal artery via energy from the energy delivery element at a plurality of treatment locations along a wall of the renal artery,
    wherein the treatment locations are spaced apart from each other and arranged in a helical pattern about the wall of the renal artery, and wherein the helical pattern includes at least one treatment location in each of an inferior, anterior, superior and posterior position around the wall,
    wherein the selected patient achieves a decrease in blood pressure of at least 5 mm Hg more than a resistant hypertensive control group patient, and
    wherein the control group patient is under 65 years of age, has a baseline blood pressure of at least 160 mm Hg, takes one or more anti-hypertensive medication at maximally tolerated doses, and underwent a sham procedure instead of the modulation treatment.

12. The method of claim 11 wherein the selected patient achieves a decrease in office blood pressure of not less than 14 mm Hg.

13. The method of claim 11, further comprising receiving a generator feedback message regarding energy delivery at a particular treatment location, and wherein the method further comprises repeating energy delivery at the particular treatment location associated with the feedback message.

14. The method of claim 11 wherein modulating the renal nerve further causes a decrease in ambulatory peak nocturnal blood pressure of at least 5 mm Hg more than the control group patient.

15. The method of claim 11 wherein modulating the renal nerve further causes a decrease in ambulatory average morning blood pressure of at least 4 mm Hg more than the control group patient.

* * * * *